(12) United States Patent
Medoff et al.

(10) Patent No.: US 10,131,894 B2
(45) Date of Patent: Nov. 20, 2018

(54) AGLYCOSYLATED ENZYME AND USES THEREOF

(71) Applicant: XYLECO, INC., Woburn, MA (US)

(72) Inventors: Marshall Medoff, Wakefield, MA (US);
Natasha Kreder, Wakefield, MA (US);
James J. Lynch, Woburn, MA (US);
Sean Landry, Essex, MA (US);
Aiichiro Yoshida, Canton, MA (US);
Desiree Pangilinan, Waltham, MA (US); Thomas Craig Masterman, Rockport, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 14/768,126

(22) PCT Filed: Aug. 7, 2015

(86) PCT No.: PCT/US2015/044136
§ 371 (c)(1),
(2) Date: Aug. 14, 2015

(87) PCT Pub. No.: WO2016/022878
PCT Pub. Date: Feb. 11, 2016

(65) Prior Publication Data
US 2017/0137797 A1    May 18, 2017

Related U.S. Application Data

(60) Provisional application No. 62/035,346, filed on Aug. 8, 2014.

(51) Int. Cl.
| | |
|---|---|
| *C12N 9/42* | (2006.01) |
| *C12P 19/02* | (2006.01) |
| *C12P 19/14* | (2006.01) |

(52) U.S. Cl.
CPC ............ *C12N 9/2445* (2013.01); *C12P 19/02* (2013.01); *C12P 19/14* (2013.01); *C12Y 302/01021* (2013.01)

(58) Field of Classification Search
None
See application file for complete search history.

(56) References Cited

U.S. PATENT DOCUMENTS

| 3,844,890 A | 10/1974 | Horikoshi et al. |
| 5,997,913 A * | 12/1999 | Fowler ............... C12G 1/00 426/15 |

(Continued)

FOREIGN PATENT DOCUMENTS

| WO | 01/36586 A2 | 5/2001 |
| WO | 2008011598 A2 | 1/2008 |

(Continued)

OTHER PUBLICATIONS

International Search Report and Written Opinion from corresponding International Application No. PCT/US2015/044136 dated Nov. 23, 2015.

(Continued)

*Primary Examiner* — Richard C Ekstrom
(74) *Attorney, Agent, or Firm* — Lando & Anastasi, LLP

(57) ABSTRACT

The present invention relates to compositions comprising an aglycosylated polypeptide having cellobiase activity, and methods for producing and using the same.

16 Claims, 10 Drawing Sheets
Specification includes a Sequence Listing.

(56) References Cited

U.S. PATENT DOCUMENTS

| | | | |
|---|---|---|---|
| 2002/0148009 A1 | 10/2002 | Khowala et al. | |
| 2009/0042266 A1* | 2/2009 | Vehmaanpera | C12P 7/10 435/165 |
| 2009/0298126 A1 | 12/2009 | Merino | |
| 2010/0216163 A1 | 8/2010 | Kuballa et al. | |
| 2011/0171674 A1* | 7/2011 | Lopes-Ferreira | C12P 7/04 435/18 |
| 2012/0052536 A1 | 3/2012 | Medoff et al. | |
| 2012/0100577 A1 | 4/2012 | Medoff et al. | |
| 2014/0011258 A1 | 1/2014 | Medoff et al. | |

FOREIGN PATENT DOCUMENTS

| | | | |
|---|---|---|---|
| WO | 2010135380 | A1 | 11/2010 |
| WO | 2011/063308 | A2 | 5/2011 |
| WO | 2012/1259521 | A1 | 9/2012 |
| WO | 2014037667 | A1 | 3/2014 |
| WO | 2014/086706 | A1 | 6/2014 |
| WO | 2016022878 | A1 | 2/2016 |

OTHER PUBLICATIONS

Dashtban et al. "Overexpression of an exotic thermotolerant ?-glucosidase in trichoderma reesei and its significant increase in cellulolytic activity and saccharification of barley straw," Microbial Cell Factories, May 20, 2012 (May 20, 2012), vol. 11, No. 63, pp. 1-15. entire document.

Van Zyl et al. "Over-expression of native *Saccharomyces cerevisiae* exocytic SNARE genes increased heterologous cellulase secretion," Appl Microbial Biotechnol, Mar. 18, 2014(Mar. 18, 2014), vol. 98, No. 12, pp. 5567-5578. entire document.

Chen et al. "Expression of a secretory ?-glucosidase from Trichoderma reesei in Pichia pastoris and its characterization," Biotechnol Lett, Aug. 9, 2011, 33:2475-2479.

Hilippidis, G. P., "Cellulose Bioconversion Technology", Handbook on Bioethanol: Production and Utilization, pp. 179-212, 1996.

Database Accession No. AZJ23300 "Hypocrea jecorina beta-glucosidase 1 (BGL1) mature mutant protein #41" dated Aug. 4, 2011.

Database Accession No. AZJ23304 "Hypocrea jecorina beta-glucosidase 1 (BGL1) mature mutant protein #45" dated Aug. 4, 2011.

Database Accession No. AZJ24531 "Hypocrea jecorina beta-glucosidase 1 (BGL1) mature mutant protein #1272" dated Aug. 4, 2011.

Seiboth et al. "Lactose metabolism and cellulase production in Hypocrea jecorina: the gal7 gene, encoding galactose-1-phosphate uridylyltransferase, is essential for growth on galactose but not for cellulase induction," Mol Genet Genomics, 2002, vol. 267, pp. 124-132.

Extended European Search Report from Application EP 15829718.4 dated Mar. 5, 2018.

Written Opinion from Application SG 11201610894U dated Jan. 29, 2018.

\* cited by examiner

```
                        SEQUENCE LISTING

<160> NUMBER OF SEQ ID NOS: 23

<210> SEQ ID NO 1
<211> LENGTH: 731
<212> TYPE: PRT
<213> ORGANISM: Trichoderma reesei

<400> SEQUENCE: 1

Met Gly Asp Ser His Ser Thr Ser Gly Ala Ser Ala Glu Ala Val Val
1               5                   10                  15

Pro Pro Ala Gly Thr Pro Trp Gly Thr Ala Tyr Asp Lys Ala Lys Ala
            20                  25                  30

Ala Leu Ala Lys Leu Asn Leu Gln Asp Lys Val Gly Ile Val Ser Gly
        35                  40                  45

Val Gly Trp Asn Gly Gly Pro Cys Val Gly Asn Thr Ser Pro Ala Ser
    50                  55                  60

Lys Ile Ser Tyr Pro Ser Leu Cys Leu Gln Asp Gly Pro Leu Gly Val
65                  70                  75                  80

Arg Tyr Ser Thr Gly Ser Thr Ala Phe Thr Pro Gly Val Gln Ala Ala
                85                  90                  95

Ser Thr Trp Asp Val Asn Leu Ile Arg Glu Arg Gly Gln Phe Ile Gly
            100                 105                 110

Glu Glu Val Lys Ala Ser Gly Ile His Val Ile Leu Gly Pro Val Ala
        115                 120                 125

Gly Pro Leu Gly Lys Thr Pro Gln Gly Gly Arg Asn Trp Glu Gly Phe
    130                 135                 140

Gly Val Asp Pro Tyr Leu Thr Gly Ile Ala Met Gly Gln Thr Ile Asn
145                 150                 155                 160

Gly Ile Gln Ser Val Gly Val Gln Ala Thr Ala Lys His Tyr Ile Leu
                165                 170                 175

Asn Glu Gln Glu Leu Asn Arg Glu Thr Ile Ser Ser Asn Pro Asp Asp
            180                 185                 190

Arg Thr Leu His Glu Leu Tyr Thr Trp Pro Phe Ala Asp Ala Val Gln
        195                 200                 205

Ala Asn Val Ala Ser Val Met Cys Ser Tyr Asn Lys Val Asn Thr Thr
    210                 215                 220

Trp Ala Cys Glu Asp Gln Tyr Thr Leu Gln Thr Val Leu Lys Asp Gln
225                 230                 235                 240

Leu Gly Phe Pro Gly Tyr Val Met Thr Asp Trp Asn Ala Gln His Thr
                245                 250                 255

Thr Val Gln Ser Ala Asn Ser Gly Leu Asp Met Ser Met Pro Gly Thr
            260                 265                 270

Asp Phe Asn Gly Asn Asn Arg Leu Trp Gly Pro Ala Leu Thr Asn Ala
        275                 280                 285

Val Asn Ser Asn Gln Val Pro Thr Ser Arg Val Asp Asp Met Val Thr
    290                 295                 300

Arg Ile Leu Ala Ala Trp Tyr Leu Thr Gly Gln Asp Gln Ala Gly Tyr
305                 310                 315                 320

Pro Ser Phe Asn Ile Ser Arg Asn Val Gln Gly Asn His Lys Thr Asn
                325                 330                 335

Val Arg Ala Ile Ala Arg Asp Gly Ile Val Leu Leu Lys Asn Asp Ala
```

```
              340                 345                 350
Asn Ile Leu Pro Leu Lys Lys Pro Ala Ser Ile Ala Val Val Gly Ser
            355                 360                 365
Ala Ala Ile Ile Gly Asn His Ala Arg Asn Ser Pro Ser Cys Asn Asp
        370                 375                 380
Lys Gly Cys Asp Asp Gly Ala Leu Gly Met Gly Trp Gly Ser Gly Ala
385                 390                 395                 400
Val Asn Tyr Pro Tyr Phe Val Ala Pro Tyr Asp Ala Ile Asn Thr Arg
                405                 410                 415
Ala Ser Ser Gln Gly Thr Gln Val Thr Leu Ser Asn Thr Asp Asn Thr
            420                 425                 430
Ser Ser Gly Ala Ser Ala Arg Gly Lys Asp Val Ala Ile Val Phe
        435                 440                 445
Ile Thr Ala Asp Ser Gly Glu Gly Tyr Ile Thr Val Glu Gly Asn Ala
    450                 455                 460
Gly Asp Arg Asn Asn Leu Asp Pro Trp His Asn Gly Asn Ala Leu Val
465                 470                 475                 480
Gln Ala Val Ala Gly Ala Asn Ser Asn Val Ile Val Val His Ser
                485                 490                 495
Val Gly Ala Ile Ile Leu Glu Gln Ile Leu Ala Leu Pro Gln Val Lys
            500                 505                 510
Ala Val Val Trp Ala Gly Leu Pro Ser Gln Glu Ser Gly Asn Ala Leu
        515                 520                 525
Val Asp Val Leu Trp Gly Asp Val Ser Pro Ser Gly Lys Leu Val Tyr
    530                 535                 540
Thr Ile Ala Lys Ser Pro Asn Asp Tyr Asn Thr Arg Ile Val Ser Gly
545                 550                 555                 560
Gly Ser Asp Ser Phe Ser Glu Gly Leu Phe Ile Asp Tyr Lys His Phe
                565                 570                 575
Asp Asp Ala Asn Ile Thr Pro Arg Tyr Glu Phe Gly Tyr Gly Leu Ser
            580                 585                 590
Tyr Thr Lys Phe Asn Tyr Ser Arg Leu Ser Val Leu Ser Thr Ala Lys
        595                 600                 605
Ser Gly Pro Ala Thr Gly Ala Val Val Pro Gly Gly Pro Ser Asp Leu
    610                 615                 620
Phe Gln Asn Val Ala Thr Val Thr Val Asp Ile Ala Asn Ser Gly Gln
625                 630                 635                 640
Val Thr Gly Ala Glu Val Ala Gln Leu Tyr Ile Thr Tyr Pro Ser Ser
                645                 650                 655
Ala Pro Arg Thr Pro Pro Lys Gln Leu Arg Gly Phe Ala Lys Leu Asn
            660                 665                 670
Leu Thr Pro Gly Gln Ser Gly Thr Ala Thr Phe Asn Ile Arg Arg Arg
        675                 680                 685
Asp Leu Ser Tyr Trp Asp Thr Ala Ser Gln Lys Trp Val Val Pro Ser
    690                 695                 700
Gly Ser Phe Gly Ile Ser Val Gly Ala Ser Ser Arg Asp Ile Arg Leu
705                 710                 715                 720
Thr Ser Thr Leu Ser Val Ala Gly Ser Gly Ser
                725                 730

<210> SEQ ID NO 2
<211> LENGTH: 2232
<212> TYPE: DNA
<213> ORGANISM: Trichoderma reesei
```

<400> SEQUENCE: 2

```
atgcgttacc gaacagcagc tgcgctggca cttgccactg ggccctttgc tagggcagac      60
agtcactcaa catcggggc ctcggctgag gcagttgtac ctcctgcagg gactccatgg      120
ggaaccgcgt acgacaaggc gaaggccgca ttggcaaagc tcaatctcca agataaggtc      180
ggcatcgtga gcggtgtcgg ctggaacggc ggtccttgcg ttggaaacac atctccggcc      240
tccaagatca gctatccatc gctatgcctt caagacggac ccctcggtgt tcgatactcg      300
acaggcagca cagcctttac gccgggcgtt caagcggcct cgacgtggga tgtcaatttg      360
atccgcgaac gtggacagtt catcggtgag gaggtgaagg cctcggggat tcatgtcata      420
cttggtcctg tggctgggcc gctgggaaag actccgcagg gcggtcgcaa ctgggagggc      480
ttcggtgtcg atccatatct cacgggcatt gccatgggtc aaaccatcaa cggcatccag      540
tcggtaggcg tgcaggcgac agcgaagcac tatatcctca cgagcagga gctcaatcga      600
gaaaccattt cgagcaaccc agatgaccga actctccatg agctgtatac ttggccattt      660
gccgacgcgg ttcaggccaa tgtcgcttct gtcatgtgct cgtacaacaa ggtcaatacc      720
acctgggcct gcgaggatca gtacacgctg cagactgtgc tgaaagacca gctggggttc      780
ccaggctatg tcatgacgga ctggaacgca cagcacacga ctgtccaaag cgcgaattct      840
gggcttgaca tgtcaatgcc tggcacagac ttcaacggta acaatcggct ctggggtcca      900
gctctcacca atgcggtaaa tagcaatcag gtccccacga gcagagtcga cgatatggtg      960
actcgtatcc tcgccgcatg gtacttgaca ggccaggacc aggcaggcta tccgtcgttc     1020
aacatcagca gaaatgttca aggaaaccac aagaccaatg tcagggcaat tgccagggac     1080
ggcatcgttc tgctcaagaa tgacgccaac atcctgccgc tcaagaagcc cgctagcatt     1140
gccgtcgttg gatctgccgc aatcattggt aaccacgcca gaaactcgcc ctcgtgcaac     1200
gacaaaggct gcgacgacgg ggccttgggc atgggttggg gttccggcgc cgtcaactat     1260
ccgtacttcg tcgcgcccta cgatgccatc aataccagag cgtcttcgca gggcacccag     1320
gttaccttga gcaacaccga caacacgtcc tcaggcgcat ctgcagcaag aggaaaggac     1380
gtcgccatcg tcttcatcac cgccgactcg ggtgaaggct acatcaccgt ggagggcaac     1440
gcgggcgatc gcaacaacct ggatccgtgg cacaacggca atgccctggt ccaggcggtg     1500
gccggtgcca acagcaacgt cattgttgtt gtccactccg ttggcgccat cattctggag     1560
cagattcttg ctcttccgca ggtcaaggcc gttgtctggg cgggtcttcc ttctcaggag     1620
agcggcaatg cgctcgtcga cgtgctgtgg ggagatgtca gcccttctgg caagctggtg     1680
tacaccattg cgaagagccc caatgactat aacactcgca tcgtttccgg cggcagtgac     1740
agcttcagcg agggactgtt catcgactat aagcacttcg acgacgccaa tatcacgccg     1800
cggtacgagt tcggctatgg actgtcttac accaagttca actactcacg cctctccgtc     1860
ttgtcgaccg ccaagtctgg tcctgcgact ggggccgttg tgccgggagg cccgagtgat     1920
ctgttccaga atgtcgcgac agtcaccgtt gacatcgcaa actctggcca agtgactggt     1980
gccgaggtag cccagctgta catcacctac ccatcttcag cacccaggac ccctccgaag     2040
cagctgcgag gctttgccaa gctgaacctc acgcctggtc agagcggaac agcaacgttc     2100
aacatccgac gacgagatct cagctactgg gacacggctt cgcagaaatg ggtggtgccg     2160
tcggggtcgt ttggcatcag cgtgggagcg agcagccggg atatcaggct gacgagcact     2220
ctgtcggtag cg                                                         2232
```

<210> SEQ ID NO 3
<211> LENGTH: 2232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgcgttatc gtacagccgc agccctggca ctggccacag gtccgttcgc acgtgccgat      60
agtcacagta ccagcggtgc cagcgcagaa gccgtggttc gccggcagg cacaccgtgg     120
ggcacagcct atgataaagc caaagccgcc ctggccaagc tgaatctgca ggataaagtg     180
ggcatcgtga gtggcgtggg ctggaacggt ggtccgtgcg ttggcaacac cagcccggca     240
agcaagatca gctatccgag cttatgcctg caggatggtc cgctgggcgt gcgctatagc     300
accggtagta ccgcctttac acctggtgtg caggccgcca gtacctggga cgttaacctg     360
atccgcgaac gtgccaatt tatcggcgaa gaagttaaag ccagcggcat tcatgttatt     420
ctgggtccgg tggccggtcc tctgggtaaa accccgcagg gcggccgtaa ttgggaaggc     480
ttcggcgttg atccgtattt aaccggcatc gcaatgggcc agaccattaa tggcatccag     540
agcgtgggtg ttcaagccac cgccaaacac tacatattaa cgaacagga actgaatcgt     600
gaaaccatca gcagcaatcc ggatgatcgc accctgcatg agctgtatac atggcctttt     660
gccgacgcag ttcaggccaa cgtggcaagt gtgatgtgta gctataacaa ggtgaacacc     720
acctgggcct gcgaagacca gtacaccctg cagaccgttt taaaagacca actgggcttc     780
cctggttacg tgatgacaga ttggaatgcc agcacacaa ccgttcagag cgcaaacagt     840
ggcctggata tgagcatgcc gggcaccgac ttcaacggca ataatcgtct gtggggtccg     900
gcactgacca atgccgttaa cagcaaccag gtgccgacca gtcgtgtgga cgatatggtt     960
acccgtattc tggccgcctg gtacctgaca ggtcaagacc aggccggcta cccgagcttc    1020
aacatcagcc gcaacgtgca gggtaatcac aagaccaacg ttcgcgcaat cgcacgcgat    1080
ggtatcgtgc tgttaaagaa cgatgccaac attctgccgc tgaaaaaacc ggccagcatc    1140
gccgttgttg gtagcgcagc catcattggc aaccacgccc gtaacagtcc gagctgcaat    1200
gataaaggct gtgacgacgg tgccctgggc atgggttggg gtagtggtgc cgtgaactac    1260
ccgtatttcg tggccccgta cgacgccatt aacacccgtg caagtagcca gggtacccag    1320
gttaccctga gcaacaccga caacacaagc agcggtgcca gtgcagcacg tggtaaggat    1380
gtggccatcg tgttcatcac cgccgacagc ggcgaaggct acattaccgt ggagggtaat    1440
gccggtgatc gcaataatct ggacccgtgg cataacggca acgccctggt tcaggcagtg    1500
gcaggcgcaa atagcaacgt gatcgttgtg gtgcatagcg tgggtgccat cattctggag    1560
cagatcctgg ccctgccgca agttaaggca gttgtgtggg caggtctgcc gagccaagaa    1620
agtggcaatg ccctggtgga cgttctgtgg ggcgatgtta gtccgagcgg caagctggtg    1680
tatacaatcg ccaagagccc gaacgactat aacacccgca tcgttagcgg cggcagtgat    1740
agcttcagcg agggcctgtt tatcgactac aagcatttcg atgatgccaa tattaccccg    1800
cgctacgaat ttggttatgg cctgagctat accaagttca actacagccg cctgagcgtt    1860
ttaagtaccg ccaagagtgg tccggcaaca ggtgccgtgg ttcctggtgg tccgagtgat    1920
ctgtttcaga atgtggccac cgtgaccgtg gatatcgcca acagtggtca ggttaccggc    1980
gccgaagtgg cacagctgta catcacctat ccgagcagtg caccgcgcac cccgccgaaa    2040
```

```
cagctgcgtg gcttcgccaa attaaacctg accccgggcc agagcggtac agcaaccttc    2100
aatattcgcc gccgtgatct gagctattgg gacaccgcca gccaaaaatg ggtggtgccg    2160
agcggcagct ttggcattag tgtgggtgca agtagccgcg acattcgctt aacaagcacc    2220
ctgagtgttg cc                                                        2232
```

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catgccatgg gcgatagtca cagtaccagc                                      30

<210> SEQ ID NO 5
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtgggactc acaacggccg tcgccgtcgg tagtagtagt agtagtagta gtgattactt     60
tcgaaccc                                                              68

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 7

His His His His His His His His
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Ser
1
```

```
<210> SEQ ID NO 9
<211> LENGTH: 800
<212> TYPE: PRT
<213> ORGANISM: Podospora anserina

<400> SEQUENCE: 9

Met Lys Ser Ser Val Phe Trp Gly Ala Ser Leu Thr Ser Ala Val Val
1               5                   10                  15

Arg Ala Ile Asp Leu Pro Phe Gln Phe Tyr Pro Asn Cys Val Asp Asp
            20                  25                  30

Leu Leu Ser Thr Asn Gln Val Cys Asn Thr Thr Leu Ser Pro Pro Glu
        35                  40                  45

Arg Ala Ala Ala Leu Val Ala Ala Leu Thr Pro Glu Glu Lys Leu Gln
50                  55                  60

Asn Ile Val Ser Lys Ser Leu Gly Ala Pro Arg Ile Gly Leu Pro Ala
65                  70                  75                  80

Tyr Asn Trp Trp Ser Glu Ala Leu His Gly Val Ala Tyr Ala Pro Gly
                85                  90                  95

Thr Gln Phe Trp Gln Gly Asp Gly Pro Phe Asn Ser Ser Thr Ser Phe
            100                 105                 110

Pro Met Pro Leu Leu Met Ala Ala Thr Phe Asp Asp Glu Leu Leu Glu
        115                 120                 125

Lys Ile Ala Glu Val Ile Gly Ile Glu Gly Arg Ala Phe Gly Asn Ala
130                 135                 140

Gly Phe Ser Gly Leu Asp Tyr Trp Thr Pro Asn Val Asn Pro Phe Lys
145                 150                 155                 160

Asp Pro Arg Trp Gly Arg Gly Ser Glu Thr Pro Gly Glu Asp Val Leu
                165                 170                 175

Leu Val Lys Arg Tyr Ala Ala Ala Met Ile Lys Gly Leu Glu Gly Pro
            180                 185                 190

Val Pro Glu Lys Glu Arg Arg Val Val Ala Thr Cys Lys His Tyr Ala
        195                 200                 205

Ala Asn Asp Phe Glu Asp Trp Asn Gly Ala Thr Arg His Asn Phe Asn
210                 215                 220

Ala Lys Ile Ser Leu Gln Asp Met Ala Glu Tyr Tyr Phe Met Pro Phe
225                 230                 235                 240

Gln Gln Cys Val Arg Asp Ser Arg Val Gly Ser Ile Met Cys Ala Tyr
                245                 250                 255

Asn Ala Val Asn Gly Val Pro Ser Cys Ala Ser Pro Tyr Leu Leu Gln
            260                 265                 270

Thr Ile Leu Arg Glu His Trp Asn Trp Thr Glu His Asn Asn Tyr Ile
        275                 280                 285

Thr Ser Asp Cys Glu Ala Val Leu Asp Val Ser Leu Asn His Lys Tyr
290                 295                 300

Ala Ala Thr Asn Ala Glu Gly Thr Ala Ile Ser Phe Glu Ala Gly Met
305                 310                 315                 320

Asp Thr Ser Cys Glu Tyr Glu Gly Ser Ser Asp Ile Pro Gly Ala Trp
                325                 330                 335

Ser Gln Gly Leu Leu Lys Glu Ser Thr Val Asp Arg Ala Leu Leu Arg
            340                 345                 350

Leu Tyr Glu Gly Ile Val Arg Ala Gly Tyr Phe Asp Gly Lys Gln Ser
        355                 360                 365

Leu Tyr Ser Ser Leu Gly Trp Ala Asp Val Asn Lys Pro Ser Ala Gln
370                 375                 380
```

```
Lys Leu Ser Leu Gln Ala Val Asp Gly Thr Val Leu Leu Lys Asn
385                 390                 395                 400

Asp Gly Thr Leu Pro Leu Ser Asp Leu Leu Asp Lys Ser Arg Pro Lys
            405                 410                 415

Lys Val Ala Met Ile Gly Phe Trp Ser Asp Ala Lys Asp Lys Leu Arg
            420                 425                 430

Gly Gly Tyr Ser Gly Thr Ala Ala Tyr Leu His Thr Pro Ala Tyr Ala
            435                 440                 445

Ala Ser Gln Leu Gly Ile Pro Phe Ser Thr Ala Ser Gly Pro Ile Leu
    450                 455                 460

His Ser Asp Leu Ala Ser Asn Gln Ser Trp Thr Asp Asn Ala Met Ala
465                 470                 475                 480

Ala Ala Lys Asp Ala Asp Tyr Ile Leu Tyr Phe Gly Gly Ile Asp Thr
            485                 490                 495

Ser Ala Ala Gly Glu Thr Lys Asp Arg Tyr Asp Leu Asp Trp Pro Gly
            500                 505                 510

Ala Gln Leu Ser Leu Ile Asn Leu Leu Thr Thr Leu Ser Lys Pro Leu
    515                 520                 525

Ile Val Leu Gln Met Gly Asp Gln Leu Asp Asn Thr Pro Leu Leu Ser
    530                 535                 540

Asn Pro Lys Ile Asn Ala Ile Leu Trp Ala Asn Trp Pro Gly Gln Asp
545                 550                 555                 560

Gly Gly Thr Ala Val Met Glu Leu Val Thr Gly Leu Lys Ser Pro Ala
            565                 570                 575

Gly Arg Leu Pro Val Thr Gln Tyr Pro Ser Asn Phe Thr Glu Leu Val
            580                 585                 590

Pro Met Thr Asp Met Ala Leu Arg Pro Ser Ala Gly Asn Ser Gln Leu
            595                 600                 605

Gly Arg Thr Tyr Arg Trp Tyr Lys Thr Pro Val Gln Ala Phe Gly Phe
    610                 615                 620

Gly Leu His Tyr Thr Thr Phe Ser Pro Lys Phe Gly Lys Lys Phe Pro
625                 630                 635                 640

Ala Val Ile Asp Val Asp Glu Val Leu Glu Gly Cys Asp Asp Lys Tyr
            645                 650                 655

Leu Asp Thr Cys Pro Leu Pro Asp Leu Pro Val Val Glu Asn Arg
            660                 665                 670

Gly Asn Arg Thr Ser Asp Tyr Val Ala Leu Ala Phe Val Ser Ala Pro
            675                 680                 685

Gly Val Gly Pro Gly Pro Trp Pro Ile Lys Thr Leu Gly Ala Phe Thr
            690                 695                 700

Arg Leu Arg Gly Val Lys Gly Glu Lys Arg Glu Gly Gly Leu Lys
705                 710                 715                 720

Trp Asn Leu Gly Asn Leu Ala Arg His Asp Glu Gly Asn Thr Val
            725                 730                 735

Val Tyr Pro Gly Lys Tyr Glu Val Ser Leu Asp Glu Pro Lys Ala
            740                 745                 750

Arg Leu Arg Phe Glu Ile Val Arg Gly Gly Lys Gly Lys Gly Lys Val
            755                 760                 765

Lys Gly Lys Gly Lys Ala Ala Gln Lys Gly Gly Val Val Leu Asp Arg
    770                 775                 780

Trp Pro Lys Pro Pro Lys Gly Gln Glu Pro Pro Ala Ile Glu Arg Val
785                 790                 795                 800
```

```
<210> SEQ ID NO 10
<211> LENGTH: 316
<212> TYPE: PRT
<213> ORGANISM: Trichoderma reesei

<400> SEQUENCE: 10

Met Val Arg Arg Thr Ala Leu Leu Ala Leu Gly Ala Leu Ser Thr Leu
1               5                   10                  15

Ser Met Ala Gln Ile Ser Asp Asp Phe Glu Ser Gly Trp Asp Gln Thr
            20                  25                  30

Lys Trp Pro Ile Ser Ala Pro Asp Cys Asn Gln Gly Thr Val Ser
        35                  40                  45

Leu Asp Thr Thr Val Ala His Ser Gly Ser Asn Ser Met Lys Val Val
    50                  55                  60

Gly Gly Pro Asn Gly Tyr Cys Gly His Ile Phe Phe Gly Thr Thr Gln
65                  70                  75                  80

Val Pro Thr Gly Asp Val Tyr Val Arg Ala Trp Ile Arg Leu Gln Thr
                85                  90                  95

Ala Leu Gly Ser Asn His Val Thr Phe Ile Ile Met Pro Asp Thr Ala
            100                 105                 110

Gln Gly Gly Lys His Leu Arg Ile Gly Gly Gln Ser Gln Val Leu Asp
        115                 120                 125

Tyr Asn Arg Glu Ser Asp Asp Ala Thr Leu Pro Asp Leu Ser Pro Asn
    130                 135                 140

Gly Ile Ala Ser Thr Val Thr Leu Pro Thr Gly Ala Phe Gln Cys Phe
145                 150                 155                 160

Glu Tyr His Leu Gly Thr Asp Gly Thr Ile Glu Thr Trp Leu Asn Gly
                165                 170                 175

Ser Leu Ile Pro Gly Met Thr Val Gly Pro Gly Val Asp Asn Pro Asn
            180                 185                 190

Asp Ala Gly Trp Thr Arg Ala Ser Tyr Ile Pro Glu Ile Thr Gly Val
        195                 200                 205

Asn Phe Gly Trp Glu Ala Tyr Ser Gly Asp Val Asn Thr Val Trp Phe
    210                 215                 220

Asp Asp Ile Ser Ile Ala Ser Thr Arg Val Gly Cys Gly Pro Gly Ser
225                 230                 235                 240

Pro Gly Gly Pro Gly Ser Ser Thr Thr Gly Arg Ser Ser Thr Ser Gly
                245                 250                 255

Pro Thr Ser Thr Ser Arg Pro Ser Thr Thr Ile Pro Pro Pro Thr Ser
            260                 265                 270

Arg Thr Thr Thr Ala Thr Gly Pro Thr Gln Thr His Tyr Gly Gln Cys
        275                 280                 285

Gly Gly Ile Gly Tyr Ser Gly Pro Thr Val Cys Ala Ser Gly Thr Thr
    290                 295                 300

Cys Gln Val Leu Asn Pro Tyr Tyr Ser Gln Cys Leu
305                 310                 315

<210> SEQ ID NO 11
<211> LENGTH: 460
<212> TYPE: PRT
<213> ORGANISM: Trichoderma reesei

<400> SEQUENCE: 11

Met Ala Ser Arg Phe Phe Ala Leu Leu Leu Ala Ile Pro Ile Gln
1               5                   10                  15

Ala Gln Ser Pro Val Trp Gly Gln Cys Gly Gly Ile Gly Trp Ser Gly
```

```
                20                  25                  30
Pro Thr Thr Cys Val Gly Gly Ala Thr Cys Val Ser Tyr Asn Pro Tyr
            35                  40                  45

Tyr Ser Gln Cys Ile Pro Ser Thr Gln Ala Ser Ser Ile Ala Ser
        50                  55                  60

Thr Thr Leu Val Thr Ser Phe Thr Thr Thr Ala Thr Arg Thr Ser
65                  70                  75                  80

Ala Ser Thr Pro Pro Ala Ser Ser Thr Gly Ala Gly Ala Thr Cys
                85                  90                  95

Ser Ala Leu Pro Gly Ser Ile Thr Leu Arg Ser Asn Ala Lys Leu Asn
            100                 105                 110

Asp Leu Phe Thr Met Phe Asn Gly Asp Lys Val Thr Thr Lys Asp Lys
            115                 120                 125

Phe Ser Cys Arg Gln Ala Glu Met Ser Glu Leu Ile Gln Arg Tyr Glu
            130                 135                 140

Leu Gly Thr Leu Pro Gly Arg Pro Ser Thr Leu Thr Ala Ser Phe Ser
145                 150                 155                 160

Gly Asn Thr Leu Thr Ile Asn Cys Gly Glu Ala Gly Lys Ser Ile Ser
                165                 170                 175

Phe Thr Val Thr Ile Thr Tyr Pro Ser Ser Gly Thr Ala Pro Tyr Pro
            180                 185                 190

Ala Ile Ile Gly Tyr Gly Gly Ser Leu Pro Ala Pro Ala Gly Val
            195                 200                 205

Ala Met Ile Asn Phe Asn Asn Asp Asn Ile Ala Ala Gln Val Asn Thr
            210                 215                 220

Gly Ser Arg Gly Gln Gly Lys Phe Tyr Asp Leu Tyr Gly Ser Ser His
225                 230                 235                 240

Ser Ala Gly Ala Met Thr Ala Trp Ala Trp Gly Val Ser Arg Val Ile
                245                 250                 255

Asp Ala Leu Glu Leu Val Pro Gly Ala Arg Ile Asp Thr Thr Lys Ile
            260                 265                 270

Gly Val Thr Gly Cys Ser Arg Asn Gly Lys Gly Ala Met Val Ala Gly
            275                 280                 285

Ala Phe Glu Lys Arg Ile Val Leu Thr Leu Pro Gln Glu Ser Gly Ala
            290                 295                 300

Gly Gly Ser Ala Cys Trp Arg Ile Ser Asp Tyr Leu Lys Ser Gln Gly
305                 310                 315                 320

Ala Asn Ile Gln Thr Ala Ser Glu Ile Ile Gly Glu Asp Pro Trp Phe
                325                 330                 335

Ser Thr Thr Phe Asn Ser Tyr Val Asn Gln Val Pro Val Leu Pro Phe
            340                 345                 350

Asp His His Ser Leu Ala Ala Leu Ile Ala Pro Arg Gly Leu Phe Val
            355                 360                 365

Ile Asp Asn Asn Ile Asp Trp Leu Gly Pro Gln Ser Cys Phe Gly Cys
            370                 375                 380

Met Thr Ala Ala His Met Ala Trp Gln Ala Leu Gly Val Ser Asp His
385                 390                 395                 400

Met Gly Tyr Ser Gln Ile Gly Ala His Ala His Cys Ala Phe Pro Ser
                405                 410                 415

Asn Gln Gln Ser Gln Leu Thr Ala Phe Val Gln Lys Phe Leu Leu Gly
            420                 425                 430

Gln Ser Thr Asn Thr Ala Ile Phe Gln Ser Asp Phe Ser Ala Asn Gln
            435                 440                 445
```

```
Ser Gln Trp Ile Asp Trp Thr Thr Pro Thr Leu Ser
    450             455             460

<210> SEQ ID NO 12
<211> LENGTH: 466
<212> TYPE: PRT
<213> ORGANISM: Trichoderma reesei

<400> SEQUENCE: 12

Met Leu Pro Lys Asp Phe Gln Trp Gly Phe Ala Thr Ala Ala Tyr Gln
1               5                   10                  15

Ile Glu Gly Ala Val Asp Gln Asp Gly Arg Gly Pro Ser Ile Trp Asp
            20                  25                  30

Thr Phe Cys Ala Gln Pro Gly Lys Ile Ala Asp Gly Ser Ser Gly Val
        35                  40                  45

Thr Ala Cys Asp Ser Tyr Asn Arg Thr Ala Glu Asp Ile Ala Leu Leu
    50                  55                  60

Lys Ser Leu Gly Ala Lys Ser Tyr Arg Phe Ser Ile Ser Trp Ser Arg
65                  70                  75                  80

Ile Ile Pro Glu Gly Gly Arg Gly Asp Ala Val Asn Gln Ala Gly Ile
                85                  90                  95

Asp His Tyr Val Lys Phe Val Asp Asp Leu Leu Asp Ala Gly Ile Thr
            100                 105                 110

Pro Phe Ile Thr Leu Phe His Trp Asp Leu Pro Glu Gly Leu His Gln
        115                 120                 125

Arg Tyr Gly Gly Leu Leu Asn Arg Thr Glu Phe Pro Leu Asp Phe Glu
    130                 135                 140

Asn Tyr Ala Arg Val Met Phe Arg Ala Leu Pro Lys Val Arg Asn Trp
145                 150                 155                 160

Ile Thr Phe Asn Glu Pro Leu Cys Ser Ala Ile Pro Gly Tyr Gly Ser
                165                 170                 175

Gly Thr Phe Ala Pro Gly Arg Gln Ser Thr Ser Glu Pro Trp Thr Val
            180                 185                 190

Gly His Asn Ile Leu Val Ala His Gly Arg Ala Val Lys Ala Tyr Arg
        195                 200                 205

Asp Asp Phe Lys Pro Ala Ser Gly Asp Gly Gln Ile Gly Ile Val Leu
    210                 215                 220

Asn Gly Asp Phe Thr Tyr Pro Trp Asp Ala Ala Asp Pro Ala Asp Lys
225                 230                 235                 240

Glu Ala Ala Glu Arg Arg Leu Glu Phe Phe Thr Ala Trp Phe Ala Asp
                245                 250                 255

Pro Ile Tyr Leu Gly Asp Tyr Pro Ala Ser Met Arg Lys Gln Leu Gly
            260                 265                 270

Asp Arg Leu Pro Thr Phe Thr Pro Glu Glu Arg Ala Leu Val His Gly
        275                 280                 285

Ser Asn Asp Phe Tyr Gly Met Asn His Tyr Thr Ser Asn Tyr Ile Arg
    290                 295                 300

His Arg Ser Ser Pro Ala Ser Ala Asp Asp Thr Val Gly Asn Val Asp
305                 310                 315                 320

Val Leu Phe Thr Asn Lys Gln Gly Asn Cys Ile Gly Pro Glu Thr Gln
                325                 330                 335

Ser Pro Trp Leu Arg Pro Cys Ala Ala Gly Phe Arg Asp Phe Leu Val
            340                 345                 350

Trp Ile Ser Lys Arg Tyr Gly Tyr Pro Pro Ile Tyr Val Thr Glu Asn
```

```
                355                 360                 365
Gly Thr Ser Ile Lys Gly Glu Ser Asp Leu Pro Lys Glu Lys Ile Leu
    370                 375                 380

Glu Asp Asp Phe Arg Val Lys Tyr Tyr Asn Glu Tyr Ile Arg Ala Met
385                 390                 395                 400

Val Thr Ala Val Glu Leu Asp Gly Val Asn Val Lys Gly Tyr Phe Ala
                405                 410                 415

Trp Ser Leu Met Asp Asn Phe Glu Trp Ala Asp Gly Tyr Val Thr Arg
            420                 425                 430

Phe Gly Val Thr Tyr Val Asp Tyr Glu Asn Gly Gln Lys Arg Phe Pro
        435                 440                 445

Lys Lys Ser Ala Lys Ser Leu Lys Pro Leu Phe Asp Glu Leu Ile Ala
    450                 455                 460

Ala Ala
465

<210> SEQ ID NO 13
<211> LENGTH: 744
<212> TYPE: PRT
<213> ORGANISM: Trichoderma reesei

<400> SEQUENCE: 13

Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255
```

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His Is
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu

```
                    675                 680                 685
Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 14
<211> LENGTH: 418
<212> TYPE: PRT
<213> ORGANISM: Trichoderma reesei

<400> SEQUENCE: 14

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300
```

```
Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
            325                 330                 335

Thr Trp Leu Arg Gln Asn Asn Arg Gln Ala Ile Leu Thr Glu Thr Gly
        340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
        370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys

<210> SEQ ID NO 15
<211> LENGTH: 471
<212> TYPE: PRT
<213> ORGANISM: Trichoderma reesei

<400> SEQUENCE: 15

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Pro Gly
                85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255
```

-continued

```
Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
            275                 280                 285

Gly His Ala Gly Trp Leu Gly Trp Pro Ala Asn Gln Asp Pro Ala Ala
            290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                    325                 330                 335

Ser Pro Pro Ser Tyr Thr Gln Gly Asn Ala Val Tyr Asn Glu Lys Leu
                340                 345                 350

Tyr Ile His Ala Ile Gly Pro Leu Leu Ala Asn His Gly Trp Ser Asn
                355                 360                 365

Ala Phe Phe Ile Thr Asp Gln Gly Arg Ser Gly Lys Gln Pro Thr Gly
                370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                    405                 410                 415

Trp Val Lys Pro Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
                450                 455                 460

Asn Ala Asn Pro Ser Phe Leu
465                 470

<210> SEQ ID NO 16
<211> LENGTH: 514
<212> TYPE: PRT
<213> ORGANISM: Trichoderma reesei

<400> SEQUENCE: 16

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
            130                 135                 140

Ser Phe Asp Val Asp Val Ser Gln Leu Pro Cys Gly Leu Asn Gly Ala
145                 150                 155                 160
```

Leu Tyr Phe Val Ser Met Asp Ala Asp Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 17
<211> LENGTH: 459
<212> TYPE: PRT
<213> ORGANISM: Trichoderma reesei

<400> SEQUENCE: 17

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
            35                  40                  45

Ala Gln Asp Thr Ser Val Val Leu Asp Trp Asn Tyr Arg Trp Met His
50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
            165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
            210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
            245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
            275                 280                 285

Val Ser Ile Thr Arg Lys Tyr Gln Gln Asn Gly Val Asp Ile Pro Ser
            290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
            325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
            370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
            405                 410                 415

Thr Ser Ser Ser Pro Ser Cys Thr Gln Thr His Trp Gly Gln Cys Gly
            420                 425                 430

```
Gly Ile Gly Tyr Ser Gly Cys Lys Thr Cys Thr Ser Gly Thr Thr Cys
                435                 440                 445

Gln Tyr Ser Asn Asp Tyr Tyr Ser Gln Cys Leu
        450                 455

<210> SEQ ID NO 18
<211> LENGTH: 234
<212> TYPE: PRT
<213> ORGANISM: Trichoderma reesei

<400> SEQUENCE: 18

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230

<210> SEQ ID NO 19
<211> LENGTH: 242
<212> TYPE: PRT
<213> ORGANISM: Trichoderma reesei

<400> SEQUENCE: 19

Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60
```

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
            85                  90                  95

Ala Gly Gln Ser Ile Ile Val Met Val Thr Asn Leu Cys Pro Asn Asn
        100                 105                 110

Gly Asn Ala Gln Trp Cys Pro Val Val Gly Gly Thr Asn Gln Tyr Gly
    115                 120                 125

Tyr Ser Tyr His Phe Asp Ile Met Ala Gln Asn Glu Ile Phe Gly Asp
130                 135                 140

Asn Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Pro Gly Ser Ser
            180                 185                 190

Pro Pro Ala Thr Ser Ser Ser Pro Pro Ser Gly Gly Gln Gln Thr
        195                 200                 205

Leu Tyr Gly Gln Cys Gly Gly Ala Gly Trp Thr Gly Pro Thr Thr Cys
210                 215                 220

Gln Ala Pro Gly Thr Cys Lys Val Gln Asn Gln Trp Tyr Ser Gln Cys
225                 230                 235                 240

Leu Pro

<210> SEQ ID NO 20
<211> LENGTH: 838
<212> TYPE: PRT
<213> ORGANISM: Trichoderma reesei

<400> SEQUENCE: 20

Met Lys Val Ser Arg Val Leu Ala Leu Val Leu Gly Ala Val Ile Pro
1               5                   10                  15

Ala His Ala Ala Phe Ser Trp Lys Asn Val Lys Leu Gly Gly Gly Gly
            20                  25                  30

Gly Phe Val Pro Gly Ile Ile Phe His Pro Lys Thr Lys Gly Val Ala
        35                  40                  45

Tyr Ala Arg Thr Asp Ile Gly Gly Leu Tyr Arg Leu Asn Ala Asp Asp
50                  55                  60

Ser Trp Thr Ala Val Thr Asp Gly Ile Ala Asp Asn Ala Gly Trp His
65                  70                  75                  80

Asn Trp Gly Ile Asp Ala Val Ala Leu Asp Pro Gln Asp Asp Gln Lys
                85                  90                  95

Val Tyr Ala Ala Val Gly Met Tyr Thr Asn Ser Trp Asp Pro Ser Asn
            100                 105                 110

Gly Ala Ile Ile Arg Ser Ser Asp Arg Gly Ala Thr Trp Ser Phe Thr
        115                 120                 125

Asn Leu Pro Phe Lys Val Gly Gly Asn Met Pro Gly Arg Gly Ala Gly
    130                 135                 140

Glu Arg Leu Ala Val Asp Pro Ala Asn Ser Asn Ile Ile Tyr Phe Gly
145                 150                 155                 160

Ala Arg Ser Gly Asn Gly Leu Trp Lys Ser Thr Asp Gly Gly Val Thr
                165                 170                 175

Phe Ser Lys Val Ser Ser Phe Thr Ala Thr Gly Thr Tyr Ile Pro Asp
            180                 185                 190

-continued

Pro Ser Asp Ser Asn Gly Tyr Asn Ser Asp Lys Gln Gly Leu Met Trp
        195                 200                 205

Val Thr Phe Asp Ser Thr Ser Ser Thr Thr Gly Gly Ala Thr Ser Arg
    210                 215                 220

Ile Phe Val Gly Thr Ala Asp Asn Ile Thr Ala Ser Val Tyr Val Ser
225                 230                 235                 240

Thr Asn Ala Gly Ser Thr Trp Ser Ala Val Pro Gly Gln Pro Gly Lys
                245                 250                 255

Tyr Phe Pro His Lys Ala Lys Leu Gln Pro Ala Glu Lys Ala Leu Tyr
            260                 265                 270

Leu Thr Tyr Ser Asp Gly Thr Gly Pro Tyr Asp Gly Thr Leu Gly Ser
        275                 280                 285

Val Trp Arg Tyr Asp Ile Ala Gly Gly Thr Trp Lys Asp Ile Thr Pro
    290                 295                 300

Val Ser Gly Ser Asp Leu Tyr Phe Gly Phe Gly Leu Gly Leu Asp
305                 310                 315                 320

Leu Gln Lys Pro Gly Thr Leu Val Val Ala Ser Leu Asn Ser Trp Trp
                325                 330                 335

Pro Asp Ala Gln Leu Phe Arg Ser Thr Asp Ser Gly Thr Thr Trp Ser
            340                 345                 350

Pro Ile Trp Ala Trp Ala Ser Tyr Pro Thr Glu Thr Tyr Tyr Tyr Ser
        355                 360                 365

Ile Ser Thr Pro Lys Ala Pro Trp Ile Lys Asn Asn Phe Ile Asp Val
    370                 375                 380

Thr Ser Glu Ser Pro Ser Asp Gly Leu Ile Lys Arg Leu Gly Trp Met
385                 390                 395                 400

Ile Glu Ser Leu Glu Ile Asp Pro Thr Asp Ser Asn His Trp Leu Tyr
                405                 410                 415

Gly Thr Gly Met Thr Ile Phe Gly Gly His Asp Leu Thr Asn Trp Asp
            420                 425                 430

Thr Arg His Asn Val Ser Ile Gln Ser Leu Ala Asp Gly Ile Glu Glu
        435                 440                 445

Phe Ser Val Gln Asp Leu Ala Ser Ala Pro Gly Gly Ser Glu Leu Leu
    450                 455                 460

Ala Ala Val Gly Asp Asp Asn Gly Phe Thr Phe Ala Ser Arg Asn Asp
465                 470                 475                 480

Leu Gly Thr Ser Pro Gln Thr Val Trp Ala Thr Pro Trp Ala Thr
                485                 490                 495

Ser Thr Ser Val Asp Tyr Ala Gly Asn Ser Val Lys Ser Val Val Arg
            500                 505                 510

Val Gly Asn Thr Ala Gly Thr Gln Gln Val Ala Ile Ser Ser Asp Gly
        515                 520                 525

Gly Ala Thr Trp Ser Ile Asp Tyr Ala Ala Asp Thr Ser Met Asn Gly
    530                 535                 540

Gly Thr Val Ala Tyr Ser Ala Asp Gly Asp Thr Ile Leu Trp Ser Thr
545                 550                 555                 560

Ala Ser Ser Gly Val Gln Arg Ser Gln Phe Gln Gly Ser Phe Ala Ser
                565                 570                 575

Val Ser Ser Leu Pro Ala Gly Ala Val Ile Ala Ser Asp Lys Lys Thr
            580                 585                 590

Asn Ser Val Phe Tyr Ala Gly Ser Gly Ser Thr Phe Tyr Val Ser Lys
        595                 600                 605

Asp Thr Gly Ser Ser Phe Thr Arg Gly Pro Lys Leu Gly Ser Ala Gly

```
          610                 615                 620

Thr Ile Arg Asp Ile Ala Ala His Pro Thr Thr Ala Gly Thr Leu Tyr
625                 630                 635                 640

Val Ser Thr Asp Val Gly Ile Phe Arg Ser Thr Asp Ser Gly Thr Thr
                    645                 650                 655

Phe Gly Gln Val Ser Thr Ala Leu Thr Asn Thr Tyr Gln Ile Ala Leu
                660                 665                 670

Gly Val Gly Ser Gly Ser Asn Trp Asn Leu Tyr Ala Phe Gly Thr Gly
                675                 680                 685

Pro Ser Gly Ala Arg Leu Tyr Ala Ser Gly Asp Ser Gly Ala Ser Trp
690                 695                 700

Thr Asp Ile Gln Gly Ser Gln Gly Phe Gly Ser Ile Asp Ser Thr Lys
705                 710                 715                 720

Val Ala Gly Ser Gly Ser Thr Ala Gly Gln Val Tyr Val Gly Thr Asn
                725                 730                 735

Gly Arg Gly Val Phe Tyr Ala Gln Gly Thr Val Gly Gly Thr Gly
                740                 745                 750

Gly Thr Ser Ser Ser Thr Lys Gln Ser Ser Ser Thr Ser Ser Ala
                755                 760                 765

Ser Ser Ser Thr Thr Leu Arg Ser Ser Val Val Ser Thr Thr Arg Ala
770                 775                 780

Ser Thr Val Thr Ser Ser Arg Thr Ser Ser Ala Ala Gly Pro Thr Gly
785                 790                 795                 800

Ser Gly Val Ala Gly His Tyr Ala Gln Cys Gly Gly Ile Gly Trp Thr
                805                 810                 815

Gly Pro Thr Gln Cys Val Ala Pro Tyr Val Cys Gln Lys Gln Asn Asp
                820                 825                 830

Tyr Tyr Tyr Gln Cys Val
                835

<210> SEQ ID NO 21
<211> LENGTH: 373
<212> TYPE: PRT
<213> ORGANISM: Podospora anserina

<400> SEQUENCE: 21

Met Lys Gly Leu Phe Ala Phe Gly Leu Gly Leu Leu Ser Leu Val Asn
1               5                   10                  15

Ala Leu Pro Gln Ala Gln Gly Gly Ala Ala Ala Ser Ala Lys Val
                20                  25                  30

Ser Gly Thr Arg Phe Val Ile Asp Gly Lys Thr Gly Tyr Phe Ala Gly
            35                  40                  45

Thr Asn Ser Tyr Trp Ile Gly Phe Leu Thr Asn Asn Arg Asp Val Asp
        50                  55                  60

Thr Thr Leu Asp His Ile Ala Ser Ser Gly Leu Lys Ile Leu Arg Val
65                  70                  75                  80

Trp Gly Phe Asn Asp Val Asn Asn Gln Pro Ser Gly Asn Thr Val Trp
                85                  90                  95

Phe Gln Arg Leu Ala Ser Ser Gly Ser Gln Ile Asn Thr Gly Pro Asn
            100                 105                 110

Gly Leu Gln Arg Leu Asp Tyr Leu Val Arg Ser Ala Glu Thr Arg Gly
        115                 120                 125

Ile Lys Leu Ile Ile Ala Leu Val Asn Tyr Trp Asp Asp Phe Gly Gly
    130                 135                 140
```

Met Lys Ala Tyr Val Asn Ala Phe Gly Gly Thr Lys Glu Ser Trp Tyr
145                 150                 155                 160

Thr Asn Ala Arg Ala Gln Glu Gln Tyr Lys Arg Tyr Ile Gln Ala Val
            165                 170                 175

Val Ser Arg Tyr Val Asn Ser Pro Ala Ile Phe Ala Trp Glu Leu Ala
            180                 185                 190

Asn Glu Pro Arg Cys Lys Gly Cys Asn Thr Asn Val Ile Phe Asn Trp
            195                 200                 205

Ala Thr Gln Ile Ser Asp Tyr Ile Arg Ser Leu Asp Lys Asp His Leu
        210                 215                 220

Ile Thr Leu Gly Asp Glu Gly Phe Gly Leu Pro Gly Gln Thr Thr Tyr
225                 230                 235                 240

Pro Tyr Gln Tyr Gly Glu Gly Thr Asp Phe Val Lys Asn Leu Gln Ile
            245                 250                 255

Lys Asn Leu Asp Phe Gly Thr Phe His Met Tyr Pro Gly His Trp Gly
            260                 265                 270

Val Pro Thr Ser Phe Gly Pro Gly Trp Ile Lys Asp His Ala Ala Ala
            275                 280                 285

Cys Arg Ala Ala Gly Lys Pro Cys Leu Leu Glu Glu Tyr Gly Tyr Glu
290                 295                 300

Ser Asp Arg Cys Asn Val Gln Lys Gly Trp Gln Gln Ala Ser Arg Glu
305                 310                 315                 320

Leu Ser Arg Asp Gly Met Ser Gly Asp Leu Phe Trp Gln Trp Gly Asp
            325                 330                 335

Gln Leu Ser Thr Gly Gln Thr His Asn Asp Gly Phe Thr Ile Tyr Tyr
            340                 345                 350

Gly Ser Ser Leu Ala Thr Cys Leu Val Thr Asp His Val Arg Ala Ile
            355                 360                 365

Asn Ala Leu Pro Ala
        370

<210> SEQ ID NO 22
<211> LENGTH: 469
<212> TYPE: PRT
<213> ORGANISM: Podospora anserina

<400> SEQUENCE: 22

Met Val Lys Leu Leu Asp Ile Gly Leu Phe Ala Leu Ala Leu Ala Ser
1               5                   10                  15

Ser Ala Val Ala Lys Pro Cys Lys Pro Arg Asp Gly Pro Val Thr Tyr
            20                  25                  30

Glu Ala Glu Asp Ala Ile Leu Thr Gly Thr Thr Val Asp Thr Ala Gln
        35                  40                  45

Val Gly Tyr Thr Gly Arg Gly Tyr Val Thr Gly Phe Asp Glu Gly Ser
    50                  55                  60

Asp Lys Ile Thr Phe Gln Ile Ser Ser Ala Thr Thr Lys Leu Tyr Asp
65                  70                  75                  80

Leu Ser Ile Arg Tyr Ala Ala Ile Tyr Gly Asp Lys Arg Thr Asn Val
                85                  90                  95

Val Leu Asn Asn Gly Ala Val Ser Glu Val Phe Phe Pro Ala Gly Asp
            100                 105                 110

Ser Phe Thr Ser Val Ala Ala Gly Gln Val Leu Leu Asn Ala Gly Gln
        115                 120                 125

Asn Thr Ile Asp Ile Val Asn Asn Trp Gly Trp Tyr Leu Ile Asp Ser
    130                 135                 140

Ile Thr Leu Thr Pro Ser Ala Pro Arg Pro His Asp Ile Asn Pro
145                 150                 155                 160

Asn Leu Asn Asn Pro Asn Ala Asp Thr Asn Ala Lys Lys Leu Tyr Ser
            165                 170                 175

Tyr Leu Arg Ser Val Tyr Gly Asn Lys Ile Ile Ser Gly Gln Gln Glu
        180                 185                 190

Leu His His Ala Glu Trp Ile Arg Gln Gln Thr Gly Lys Thr Pro Ala
    195                 200                 205

Leu Val Ala Val Asp Leu Met Asp Tyr Ser Pro Ser Arg Val Glu Arg
210                 215                 220

Gly Thr Thr Ser His Ala Val Glu Asp Ala Ile Ala His His Asn Ala
225                 230                 235                 240

Gly Gly Ile Val Ser Val Leu Trp His Trp Asn Ala Pro Val Gly Leu
                245                 250                 255

Tyr Asp Thr Glu Glu Asn Lys Trp Trp Ser Gly Phe Tyr Thr Arg Ala
            260                 265                 270

Thr Asp Phe Asp Ile Ala Ala Thr Leu Ala Asn Pro Gln Gly Ala Asn
        275                 280                 285

Tyr Thr Leu Leu Ile Arg Asp Ile Asp Ala Ile Ala Val Gln Leu Lys
    290                 295                 300

Arg Leu Glu Ala Ala Gly Val Pro Val Leu Trp Arg Pro Leu His Glu
305                 310                 315                 320

Ala Glu Gly Gly Trp Phe Trp Trp Gly Ala Lys Gly Pro Glu Pro Ala
                325                 330                 335

Lys Gln Leu Trp Asp Ile Leu Tyr Glu Arg Leu Thr Val His His Gly
            340                 345                 350

Leu Asp Asn Leu Ile Trp Val Trp Asn Ser Ile Leu Glu Asp Trp Tyr
        355                 360                 365

Pro Gly Asp Asp Thr Val Asp Ile Leu Ser Ala Asp Val Tyr Ala Gln
    370                 375                 380

Gly Asn Gly Pro Met Ser Thr Gln Tyr Asn Glu Leu Ile Ala Leu Gly
385                 390                 395                 400

Arg Asp Lys Lys Met Ile Ala Ala Glu Val Gly Ala Ala Pro Leu
                405                 410                 415

Pro Gly Leu Leu Gln Ala Tyr Gln Ala Asn Trp Leu Trp Phe Ala Val
            420                 425                 430

Trp Gly Asp Asp Phe Ile Asn Asn Pro Ser Trp Asn Thr Val Ala Val
        435                 440                 445

Leu Asn Glu Ile Tyr Asn Ser Asp Tyr Val Leu Thr Leu Asp Glu Ile
    450                 455                 460

Gln Gly Trp Arg Ser
465

<210> SEQ ID NO 23
<211> LENGTH: 493
<212> TYPE: PRT
<213> ORGANISM: Trichoderma reesei

<400> SEQUENCE: 23

Met Ala Gly Lys Leu Ile Leu Val Ala Leu Ala Ser Leu Val Ser Leu
1               5                   10                  15

Ser Ile Gln Gln Asn Cys Ala Ala Leu Phe Gly Gln Cys Gly Gly Ile
            20                  25                  30

Gly Trp Ser Gly Thr Thr Cys Cys Val Ala Gly Ala Gln Cys Ser Phe

```
                  35                  40                  45
Val Asn Asp Trp Tyr Ser Gln Cys Leu Ala Ser Thr Gly Gly Asn Pro
 50                  55                  60
Pro Asn Gly Thr Thr Ser Ser Ser Leu Val Ser Arg Thr Ser Ser Ala
 65                  70                  75                  80
Ser Ser Ser Val Gly Ser Ser Ser Pro Gly Asn Ser Pro Thr Gly
                     85                  90                  95
Ser Ala Ser Thr Tyr Thr Thr Thr Asp Thr Ala Thr Val Ala Pro His
                    100                 105                 110
Ser Gln Ser Pro Tyr Pro Ser Ile Ala Ala Ser Ser Cys Gly Ser Trp
                    115                 120                 125
Thr Leu Val Asp Asn Val Cys Cys Pro Ser Tyr Cys Ala Asn Asp Asp
                    130                 135                 140
Thr Ser Glu Ser Cys Ser Gly Cys Gly Thr Cys Thr Thr Pro Pro Ser
145                 150                 155                 160
Ala Asp Cys Lys Ser Gly Thr Met Tyr Pro Glu Val His His Val Ser
                    165                 170                 175
Ser Asn Glu Ser Trp His Tyr Ser Arg Ser Thr His Phe Gly Leu Thr
                    180                 185                 190
Ser Gly Gly Ala Cys Gly Phe Gly Leu Tyr Gly Leu Cys Thr Lys Gly
                    195                 200                 205
Ser Val Thr Ala Ser Trp Thr Asp Pro Met Leu Gly Ala Thr Cys Asp
210                 215                 220
Ala Phe Cys Thr Ala Tyr Pro Leu Leu Cys Lys Asp Pro Thr Gly Thr
225                 230                 235                 240
Thr Leu Arg Gly Asn Phe Ala Ala Pro Asn Gly Asp Tyr Tyr Thr Gln
                    245                 250                 255
Phe Trp Ser Ser Leu Pro Gly Ala Leu Asp Asn Tyr Leu Ser Cys Gly
                    260                 265                 270
Glu Cys Ile Glu Leu Ile Gln Thr Lys Pro Asp Gly Thr Asp Tyr Ala
                    275                 280                 285
Val Gly Glu Ala Gly Tyr Thr Asp Pro Ile Thr Leu Glu Ile Val Asp
                    290                 295                 300
Ser Cys Pro Cys Ser Ala Asn Ser Lys Trp Cys Cys Gly Pro Gly Ala
305                 310                 315                 320
Asp His Cys Gly Glu Ile Asp Phe Lys Tyr Gly Cys Pro Leu Pro Ala
                    325                 330                 335
Asp Ser Ile His Leu Asp Leu Ser Asp Ile Ala Met Gly Arg Leu Gln
                    340                 345                 350
Gly Asn Gly Ser Leu Thr Asn Gly Val Ile Pro Thr Arg Tyr Arg Arg
                    355                 360                 365
Val Gln Cys Pro Lys Val Gly Asn Ala Tyr Ile Trp Leu Arg Asn Gly
                    370                 375                 380
Gly Gly Pro Tyr Tyr Phe Ala Leu Thr Ala Val Asn Thr Asn Gly Pro
385                 390                 395                 400
Gly Ser Val Thr Lys Ile Glu Ile Lys Gly Ala Asp Thr Asp Asn Trp
                    405                 410                 415
Val Ala Leu Val His Asp Pro Asn Tyr Thr Ser Ser Arg Pro Gln Glu
                    420                 425                 430
Arg Tyr Gly Ser Trp Val Ile Pro Gln Gly Ser Gly Pro Phe Asn Leu
                    435                 440                 445
Pro Val Gly Ile Arg Leu Thr Ser Pro Thr Gly Glu Gln Ile Val Asn
450                 455                 460
```

```
Glu Gln Ala Ile Lys Thr Phe Thr Pro Pro Ala Thr Gly Asp Pro Asn
465                 470                 475                 480

Phe Tyr Tyr Ile Asp Ile Gly Val Gln Phe Ser Gln Asn
                485             490
```

AGLYCOSYLATED ENZYME AND USES THEREOF

RELATED APPLICATIONS

This application is a national stage application under 35 U.S.C. § 371 of International Application No. PCT/US2015/044136, filed Aug. 7, 2015, which claims the benefit of U.S. Provisional Application No. 62/035,346, filed Aug. 8, 2014; the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Aug. 5, 2015, is named X2002-7000WO_SL.txt and is 76,949 bytes in size.

FIELD OF THE INVENTION

The present invention relates generally to compositions having cellobiase activity and methods for producing the compositions described herein. The present invention also provides methods for using such compositions, e.g., to process biomass materials.

BACKGROUND OF THE INVENTION

Biomass-degrading enzymes, such as cellulases, xylanases, and ligninases, are important for the degradation of biomass, such as feedstock. Cellulosic and lignocellulosic materials are produced, processed, and used in large quantities in a number of applications. Often such materials are used once, and then discarded as waste, or are simply considered to be wasted materials, e.g., sewage, bagasse, sawdust, and stover

SUMMARY OF THE INVENTION

The present invention is based, at least in part, on the surprising discovery that a cellobiase from *T. reesei* that was expressed in a non-fungal cell line and isolated from a host cell that does not significantly glycosylate the enzyme had higher specific activity on pure substrate than the endogenous cellobiase (glycosylated and secreted) from *T. reesei*. Furthermore, when the aglycosylated cellobiase was used in a saccharification reaction with an enzyme mixture containing other saccharifying enzymes, a substantial increase in yield of sugar products was observed compared to the reaction without the aglycosylated cellobiase. Therefore, provided herein are, an aglycosylated polypeptide having enzymatic activity, e.g., cellobiase activity, compositions comprising the aglycosylated polypeptide and methods for producing and using the compositions described herein.

Accordingly, in one aspect, the disclosure features an aglycosylated polypeptide having cellobiase activity. In one embodiment, the aglycosylated polypeptide has increased cellobiase activity as compared to glycosylated Cel3A enzyme from wild-type *T. reesei* or a mutant thereof, such as *T. reesei* RUTC30. For example, the aglycosylated polypeptide can have increased substrate recognition or a more active substrate recognition site as compared to glycosylated Cel3A enzyme from wild-type *T. reesei*. In one embodiment, the aglycosylated polypeptide has reduced steric hindrance as compared to glycosylated Cel3A enzyme from wild-type *T. reesei*.

In one embodiment, the aglycosylated polypeptide comprises at least 75%, 80%, 85%, 90%, 95%, 96%, 97%, 98%, 99% identity to SEQ ID NO: 1, or a functional fragment thereof. In one embodiment, the aglycosylated polypeptide comprises (e.g., consists of) the amino acid sequence SEQ ID NO: 1. In another embodiment, the aglycosylated polypeptide differs by no more than 1, 2, 3, 4, 5, 6, 7, 8, 9, 10, 15, or 20 amino acids from the amino acid sequence of SEQ ID NO: 1.

In one embodiment, the polypeptide comprises a Cel3A enzyme from wild-type *T. reesei*, or a mutant thereof, such as *T. reesei* RUTC30, or a functional variant or fragment thereof.

In one embodiment, the aglycosylated polypeptide is encoded by a nucleic acid sequence, wherein the nucleic acid sequence comprises (e.g., consists of) at least 75%, 80%, 85%, 90%, 95%, 96%, 97%, 98%, 99% identity to SEQ ID NO: 2 or SEQ ID NO: 3. In one embodiment, the aglycosylated polypeptide is encoded by a nucleic acid sequence comprising (e.g., consisting of) SEQ ID NO: 2 or SEQ ID NO: 3.

In one embodiment, the aglcyosylated polypeptide is expressed by a gene that comprises a mutation proximal to or a mutation at one or more glycosylation site, wherein the mutation prevents glycosylation at the glycosylation site. In one embodiment, the mutation is at one or more of the threonine at amino acid position 78, the threonine at amino acid position 241, the serine at amino acid position 343, the serine at amino acid position 450, the threonine at amino acid position 599, the serine at amino acid position 616, the threonine at amino acid position 691, the serine at amino acid position 21, the threonine at amino acid position 24, the serine at amino acid position 25, the serine at amino acid position 28, the threonine at amino acid position 38, the threonine at amino acid position 42, the threonine at amino acid position 303, the serine at amino acid position at 398, the at serine amino acid position 435, the serine at amino acid position 436, the threonine at amino acid position 439, threonine at amino acid position 442, the threonine at amino acid position 446, the serine at amino acid position 451, the serine at amino acid position 619, the serine at amino acid position 622, the threonine at amino acid position 623, the serine at amino acid position 626, or the threonine at amino acid position 630 of SEQ ID NO: 1. A mutation proximal to one or more glycosylation site can prevent glycosylation at that site, e.g., by changing the conformation of the polypeptide or changing the consensus site recognized by the glycosylating enzyme such that glycosylation would not occur at the glycosylation site.

In one embodiment, the aglycosylated polypeptide hydrolyzes a carbohydrate, such as a dimer, a trimer, a tetramer, a pentamer, a hexamer, a heptamer, an octamer, or an oligomer of glucose; or an oligomer of glucose and xylose, into one or more monosaccharide, e.g., glucose. In one embodiment, the cellobiase activity comprises hydrolysis of a beta 1,4 glycosidic linkage of cellobiose.

In another aspect, the disclosure features a nucleic acid sequence encoding an aglycosylated polypeptide described herein.

In one embodiment, the nucleic acid sequence encodes a Cel3A enzyme or functional fragment thereof, wherein the nucleic acid sequence comprises (e.g., consists of) at least 75%, 80%, 85%, 90%, 95%, 96%, 97%, 98%, 99% identity to SEQ ID NO: 2 or SEQ ID NO: 3. In one embodiment, the nucleic acid sequence encodes a Cel3A enzyme, wherein the nucleic acid sequence comprises (e.g., consists of) SEQ ID NO: 2 or SEQ ID NO: 3.

In one aspect, the disclosure features a nucleic acid molecule that includes a nucleic acid sequence described herein.

In one embodiment, the nucleic acid molecule further includes a promoter, e.g., a promoter for prokaryotic cell expression, e.g., bacterial cell expression, e.g., expression in *E. coli*. In one embodiment, the promoter sequence is a constitutive promoter sequence, inducible promoter sequence, or a repressible promoter sequence. In one embodiment, the promoter is a T7 promoter.

In one embodiment, the nucleic acid molecule further comprises a nucleic acid sequence encoding a tag, e.g., a tag for detection and/or purification and/or for linkage to another molecule, e.g., a His tag.

In one embodiment, the nucleic acid molecule further comprises a nucleic acid encoding one or more signal sequences, e.g., a secretion signal sequence.

In one aspect, the disclosure features an expression vector comprising the nucleic acid sequence described herein or a nucleic acid molecule described herein.

In one embodiment, the vector further comprises a nucleic acid sequence encoding a selection marker, e.g., a kanamycin or an ampicillin marker.

In one aspect, the disclosure features a cell comprising a vector described herein.

In one embodiment, the cell is a prokaryotic cell/bacterial cell, e.g., an *E. coli* cell, e.g., an Origami *E. coli* cell.

In one embodiment, the cell expresses an aglycosylated polypeptide described herein.

In one embodiment, the cell is impaired for glycosylation.

In one aspect, the disclosure features a method for producing the aglycosylated polypeptide described herein, comprising culturing a cell expressing a polypeptide described herein, under conditions suitable for the expression of the polypeptide, wherein the cell does not glycosylate the polypeptide, e.g., a bacterial cell, e.g., an *E. coli* cell, e.g., an origami *E. coli* cell.

In one aspect, the disclosure features a method for producing the aglycosylated polypeptide described herein, comprising treating a polypeptide comprising an amino acid sequence of SEQ ID NO:1, or an amino acid sequence with at least 75%, 80%, 85%, 90%, 95%, 96%, 97%, 98%, 99% identity to SEQ ID NO: 1 with a deglycosylating enzyme. For example, a deglycosylating enzyme can be PGNase or EndoH.

In one aspect, the disclosure features a method for producing the aglycosylated polypeptide described herein, comprising culturing a cell that comprises a nucleic acid sequence encoding a polypeptide having at least 75%, 80%, 85%, 90%, 95%, 96%, 97%, 98%, 99% identity to SEQ ID NO: 1, wherein the nucleic acid has one or more mutations which prevent glycosylation of the encoded polypeptide, and optionally obtaining the aglycosylated polypeptide from the culture.

In one aspect, the disclosure features a method for culturing a cell expressing the aglycosylated polypeptide described herein in the presence of a glycosylation inhibitor. For example, the glycosylation inhibitor is tunicamycin.

In one aspect, the disclosure features an enzyme mixture comprising an aglycosylated polypeptide described herein and one or more additional enzyme, such as one or more glycosylated enzymes, e.g., cellulases from fungal cells. In one embodiment, the enzyme mixture comprises a glycosylated polypeptide comprising an amino acid sequence with at least 75%, 80%, 95%, 90%, 95%, 96%, 97%, 98%, 99% identity to SEQ ID NO: 1 and an aglycosylated polypeptide described herein, wherein both of the glycosylated polypeptide and the aglycosylated peptide have cellobiase activity.

In one embodiment, the enzyme mixture comprises a glycosylated polypeptide and an aglycosylated polypeptide and both the glycosylated polypeptide and the aglycosylated polypeptide both comprise Cel3A enzyme from wild-type *T. reesei* or a mutant thereof, such as *T. reesei* RUTC30.

In one embodiment, the enzyme mixture further comprises at least one additional enzyme derived from a microorganism, wherein the additional enzyme has a biomass-degrading activity. In one embodiment, the additional enzyme is selected from a ligninase, an endoglucanase, a cellobiohydrolase, xylanase, and a cellobiase.

In one embodiment, the reaction mixture has a ratio between the aglycosylated polypeptide and the remaining enzymes of at least 1:32, e.g., 1:32 to 1:300. In one embodiment, the reaction mixture has a ratio of the aglycosylated polypeptide to a glycosylated polypeptide is at least 1:32, e.g., 1:32 to 1:300.

In one aspect, the disclosure features a method of producing a product (e.g., hydrogen, a sugar, an alcohol, etc.) from a biomass (or converting a biomass to a product) comprising contacting a biomass, e.g., a biomass that has been treated with radiation, e.g., radiation from an electron beam, with an aglycosylated polypeptide described herein, under conditions suitable for the production of a sugar product. In one embodiment, the method further comprises contacting the biomass with a microorganism that produces one or more biomass-degrading enzyme or an enzyme mixture comprising biomass-degrading enzymes, e.g., an enzyme mixture described herein.

In one aspect, the disclosure features a method of producing a product (e.g., hydrogen, sugar, alcohol, etc.) from a biomass (or converting a biomass to a product) comprising contacting a biomass with an enzyme mixture described herein under conditions suitable for the production of the product.

In one embodiment, the product is a sugar product, e.g., a sugar product described herein. In one embodiment, the sugar product is glucose and/or xylose, or other sugar products, such as fructose, arabinose, galactose, and cellobiose.

In one embodiment, the method further comprises isolating the sugar product. In one embodiment, the isolating of the sugar product comprises precipitation, crystallization, chromatography, centrifugation, and/or extraction.

In one embodiment, the enzyme mixture comprises at least two of the enzymes selected from B2AF03, CIP1, CIP2, Cel1a, Cel3a, Cel5a, Cel6a, Cel1a, Cel7b, Cel12a, Cel45a, Cel74a, paMan5a, paMan26a, Swollenin, or any of the enzymes listed in Table 1. In an embodiment, the enzymes listed above are isolated from a cell that expresses the enzyme heterologously or endogenously, e.g., *Trichoderma reesei* or *Podospora anserina*.

In one embodiment, the biomass comprises a starchy material or a starchy material that includes a cellulosic component. In some embodiments, the biomass comprises one or more of an agricultural product or waste, a paper product or waste, a forestry product, or a general waste, or any combination thereof; wherein: a) an agricultural product or waste comprises sugar cane jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof; b) a paper product or waste comprises paper, pigmented papers, loaded papers, coated papers, filled papers, magazines, printed matter, printer paper, polycoated paper, cardstock, cardboard, paperboard, or paper pulp, or a combination thereof; c) a forestry product comprises aspen wood, particle board, wood chips, or sawdust, or a combination thereof; and d) a general waste comprises manure, sewage, or offal, or a combination thereof. In one embodiment, the method further comprises a step of treating the biomass prior to introducing the microorganism or the enzyme mixture to reduce the recalcitrance of the biomass, e.g., by treating the biomass with bombardment with electrons, sonication, oxidation, pyrolysis, steam explosion, chemical treatment, mechanical treatment, and/or freeze grinding.

In one embodiment, the microorganism that produces a biomass-degrading enzyme is from species in the genera selected from *Bacillus, Coprinus, Myceliophthora, Cephalosporium, Scytalidium, Penicillium, Aspergillus, Pseudomonas, Humicola, Fusarium, Thielavia, Acremonium, Chrysosporium* or *Trichoderma*. In one embodiment, the microorganism that produces a biomass-degrading enzyme is selected from *Aspergillus, Humicola insolens* (*Scytalidium thermophilum*), *Coprinus cinereus, Fusarium oxysporum, Myceliophthora thermophila, Meripilus giganteus, Thielavia terrestris, Acremonium persicinum, Acremonium acremonium, Acremonium brachypenium, Acremonium dichromosporum, Acremonium obclavatum, Acremonium pinkertoniae, Acremonium roseogriseum, Acremonium incoloratum, Acremonium furatum, Chrysosporium lucknowense, Trichoderma viride, Trichoderma reesei,* or *Trichoderma koningii*.

In one embodiment, the microorganism has been induced to produce biomass-degrading enzymes by combining the microorganism with an induction biomass sample under conditions suitable for increasing production of biomass-degrading enzymes compared to an uninduced microorganism. In one embodiment, the induction biomass sample comprises paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, *miscanthus*, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, agricultural or industrial waste, arracacha, buckwheat, banana, barley, cassava, kudzu, oca, sago, sorghum, potato, sweet potato, taro, yams, beans, favas, lentils, peas, or any combination thereof.

BRIEF DESCRIPTION OF THE DRAWINGS

FIG. 6 is a graph showing a standard curve for cellobiase activity generated for a known concentration of Cel3a-N'His that can be used to determine the concentration of Cel3a of a sample with an unknown concentration of Cel3a.

DETAILED DESCRIPTION

Definitions

Figure 1:
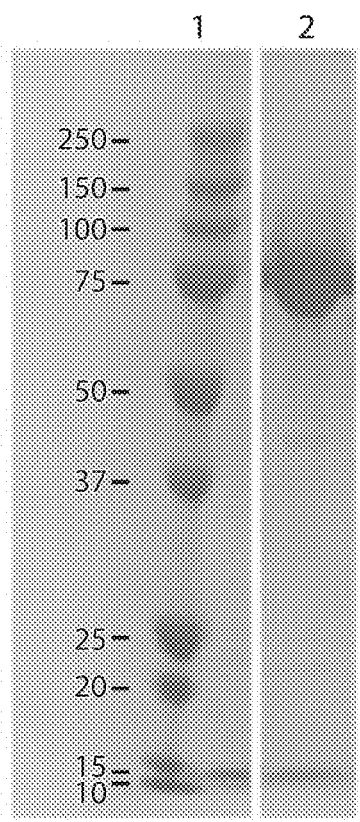
FIG. 1 is a picture of purified Cel3a that was expressed in *E. coli*. Lane 1 represents molecular weight marker (Precision Plus All Blue Protein marker, Biorad); lane 2 represents purified Cel3a-His protein.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "aglycosylated", as used herein, refers to a molecule, e.g., a polypeptide, that is not glycosylated (i.e., it comprises a hydroxyl group or other functional group that is not attached to a glycosylate group) at one or more sites which has a glycan attached when the molecule is produced in its native environment. For example, a Cel3A enzyme is aglycosylated when one or more site in the protein that normally has a glycan group attached to it when the Cel3A enzyme is produced in *T. reesei* does not have a glycan attached at that site. In some embodiments, the aglycosylated molecule does not have any attached glycans. In one embodiment, the molecule has been altered or mutated such that the molecule cannot be glycosylated, e.g., one or more glycosylation site is mutated such that a glycan cannot be attached to the glycosylation site. In another embodiment, an attached glycan can be removed from the molecule, e.g., by an enzymatic process, e.g., by incubating with enzymes that remove glycans or have deglycosylating activity. In yet another embodiment, glycosylation of the molecule can be inhibited, e.g., by use of a glycosylation inhibitor (that inhibits a glycosylating enzyme). In another embodiment, the molecule, e.g., the polypeptide, can be produced by a host cell that does not glycosylate, e.g., *E. coli*.

The term "biomass", as used herein, refers to any non-fossilized, organic matter. Biomass can be a starchy material and/or a cellulosic, hemicellulosic, or lignocellulosic material. For example, the biomass can be an agricultural product, a paper product, forestry product, or any intermediate, byproduct, residue or waste thereof, or a general waste. The biomass may be a combination of such materials. In an embodiment, the biomass is processed, e.g., by a saccharification and/or a fermentation reaction described herein, to produce products, such as sugars, alcohols, organic acids, or biofuels.

The term "biomass degrading enzymes", as used herein, refers to enzymes that break down components of the biomass matter described herein into intermediates or final products. For example, biomass-degrading enzymes include at least amylases, e.g., alpha, beta or gamma amylases, cellulases, hemicellulases, ligninases, endoglucancases, cellobiases, xylanases, and cellobiohydrolases. Biomass-degrading enzymes are produced by a wide variety of microorganisms, and can be isolated from the microorganisms, such as *T. reesei*. The biomass degrading enzyme can be endogenously expressed or heterologously expressed.

The term "cellobiase", as used herein, refers to an enzyme that catalyzes the hydrolysis of a dimer, trimer, tetramer, pentamer, hexamer, heptamer, octamer, or an oligomer of glucose, or an oligomer of glucose and xylose, to glucose and/or xylose. For example, the cellobiase is beta-glucosidase, which catalyzes beta-1,4 bonds in cellobiose to release two glucose molecules.

The term "cellobiase activity", as used herein, refers to activity of a category of cellulases that catalyze the hydrolysis of cellobiose to glucose, e.g., catalyzes the hydrolysis of beta-D-glucose residues to release beta-D-glucose. Cellobiase activity can be determined according to the assays described herein, e.g., in Example 6. One unit of cellobiase activity can be defined as [glucose] g/L/[Cel3a] g/L/30 minutes.

The term "cellobiohydrolase" as used herein, refers to an enzyme that hydrolyzes glycosidic bonds in cellulose. For example, the cellobiohydrolase is 1,4-beta-D-glucan cellobiohydrolase, which catalyzes the hydrolysis of 1,4-beta-D-glucosidic linkages in cellulose, cellooligosaccharides, or any beta-1,4-linked glucose containing polymer, releasing oligosaccharides from the polymer chain.

The term "endoglucanase" as used herein, refers to an enzyme that catalyzes the hydrolysis of internal β-1,4 glucosidic bonds of cellulose. For example, the endoglucanase is endo-1,4-(1,3;1,4)-beta-D-glucan 4-glucanohydrolase, which catalyses endohydrolysis of 1,4-beta-D-glycosidic linkages in cellulose, cellulose derivatives (such as carboxymethyl cellulose and hydroxyethyl cellulose), lichenan, beta-1,4 bonds in mixed beta-1,3 glucans such as cereal beta-D-glucans or xyloglucans, and other plant material containing cellulosic components.

The term "enzyme mixture" as used herein, refers to a combination of at least two different enzymes, or at least two different variants of an enzyme (e.g., a glycosylated and an aglycosylated version of an enzyme). The enzyme mixture referred to herein includes at least the aglycosylated polypeptide having cellobiase activity described herein. In one embodiment, the enzyme mixture includes one or more of a cellobiase, an endoglucanase, a cellobiohydrolase, a ligninase, and/or a xylanase. In some embodiments, the enzyme mixture includes a cell, e.g., a microorganism, which expresses and, e.g., secretes, one or more of the enzymes. For example, the enzyme mixture can include an aglycosylated polypeptide described herein and a cell, e.g., a microorganism, which expresses and, e.g., secretes, one or more additional enzymes and/or variants of the polypeptide.

The term "ligninase" as used herein, refers to an enzyme that catalyzes the breakdown of lignin, commonly found in the cell walls of plants, such as by an oxidation reaction.

The terms "nucleic acid" or "polynucleotide" are used interchangeable, and refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The term "operably linked", as used herein, refers to a configuration in which a control or regulatory sequence is placed at a position relative to a nucleic acid sequence that encodes a polypeptide, such that the control sequence influences the expression of a polypeptide (encoded by the DNA sequence). In an embodiment, the control or regulatory sequence is upstream of a nucleic acid sequence that encodes a polypeptide with cellobiase activity. In an embodiment, the control or regulatory sequence is downstream of a nucleic acid sequence that encodes a polypeptide with cellobiase activity.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter", as used herein, refers to a DNA sequence recognized by the synthetic machinery of the cell, or introduced synthetic machinery, required to initiate the specific transcription of a polynucleotide sequence.

The term "regulatory sequence" or "control sequence", as used interchangeably herein, refers to a nucleic acid sequence which is required for expression of a nucleic acid product. In some instances, this sequence may be a promoter sequence and in other instances, this sequence may also include an enhancer sequence and other regulatory elements which are required for expression of the gene product. The regulatory/control sequence may, for example, be one which expresses the nucleic acid product in a regulated manner, e.g., inducible manner.

The term "constitutive" promoter refers to a nucleotide sequence which, when operably linked with a polynucleotide which encodes a polypeptide, causes the polypeptide to be produced in a cell under most or all physiological conditions of the cell. In an embodiment, the polypeptide is a polypeptide having cellobiase activity.

The term "inducible" promoter refers to a nucleotide sequence which, when operably linked with a polynucleotide which encodes a polypeptide, causes the polypeptide to be produced in a cell substantially only when an inducer which corresponds to the promoter is present in the cell. In an embodiment, the polypeptide is a polypeptide having cellobiase activity.

The term "repressible" promoter refers to a nucleotide sequence, which when operably linked with a polynucleotide which encodes a polypeptide, causes the polypeptide to be produced in a cell substantially only until a repressor which corresponds to the promoter is present in the cell. In an embodiment, the polypeptide is a polypeptide having cellobiase activity.

The term "xylanase" as used herein, refers to enzymes that hydrolyze xylan-containing material. Xylan is polysaccharide comprising units of xylose. A xylanase can be an endoxylanase, a beta-xylosidase, an arabinofuranosidase, an alpha-glucuronidase, an acetylxylan esterase, a feruloyl esterase, or an alpha-glucuronyl esterase.

DESCRIPTION

Glycosylation is thought to play a critical role in enzyme structure and function, such as enzyme activity, solubility, stability, folding, and/or secretion. Accordingly, processes for converting biomass into biofuels and other products have focused on producing and utilizing glycosylated enzymes, e.g., cellobiases, for use in saccharification of cellulosic and/or lignocellulosic materials. Enzymes for use in saccharification are typically produced in eukaryote host cell lines that properly glycosylate, fold, and secrete the proteins, such as *Pichia pastoris*.

The present invention is based, at least in part, on the surprising discovery that a cellobiase from *T. reesei* that was expressed in a non-fungal cell line and isolated from a host cell that does not significantly glycosylate the enzyme had higher specific activity on pure substrate than the endogenous cellobiase (glycosylated and secreted) from *T. reesei*. Furthermore, when the aglycosylated cellobiase was used in a saccharification reaction with an enzyme mixture containing other saccharifying enzymes, a substantial increase in yield of sugar products was observed compared to the reaction without the aglycosylated cellobiase. Therefore, provided herein are, an aglycosylated polypeptide having enzymatic activity, e.g., cellobiase activity, compositions comprising the aglycosylated polypeptide and methods for producing and using the compositions described herein.
Polypeptides and Variants The present disclosure provides an aglycosylated polypeptide with cellobiase activity. In an embodiment, the aglycosylated polypeptide is a cellobiase. A cellobiase is an enzyme that hydrolyzes beta-1,4 bonds in its substrate, cellobiose, to release two glucose molecules. Cellobiose is a water soluble 1,4-linked dimer of glucose.

Cel3a (also known as BglI) is a cellobiase that was identified in *Trichoderma reesei*. The amino acid sequence for Cel3a (GenBank Accession No. NW_006711153) is provided below:

(SEQ ID NO: 1)
MGDSHSTSGASAEAVVPPAGTPWGTAYDKAKAALAKLNLQDKVGIVSGVG

WNGGPCVGNTSPASKISYPSLCLQDGPLGVRYSTGSTAFTPGVQAASTWD

VNLIRERGQFIGEEVKASGIHVILGPVAGPLGKTPQGGRNWEGFGVDPYL

TGIAMGQTINGIQSVGVQATAKHYILNEQELNRETISSNPDDRTLHELYT

WPFADAVQANVASVMCSYNKVNTTWACEDQYTLQTVLKDQLGFPGYVMTD

-continued
WNAQHTTVQSANSGLDMSMPGTDFNGNNRLWGPALTNAVNSNQVPTSRVD

DMVTRILAAWYLTGQDQAGYPSFNISRNVQGNHKTNVRAIARDGIVLLKN

DANILPLKKPASIAVVGSAAIIGNHARNSPSCNDKGCDDGALGMGWGSGA

VNYPYFVAPYDAINTRASSQGTQVTLSNTDNTSSGASAARGKDVAIVFIT

ADSGEGYITVEGNAGDRNNLDPWHNGNALVQAVAGANSNVIVVVHSVGAI

ILEQILALPQVKAVVWAGLPSQESGNALVDVLWGDVSPSGKLVYTIAKSP

NDYNTRIVSGGSDSFSEGLFIDYKHFDDANITPRYEFGYGLSYTKFNYSR

LSVLSTAKSGPATGAVVPGGPSDLFQNVATVTVDIANSGQVTGAEVAQLY

ITYPSSAPRTPPKQLRGFAKLNLTPGQSGTATFNIRRRDLSYWDTASQKW

VVPSGSFGISVGASSRDIRLTSTLSVAGSGS

The present disclosure also provides functional variants of an aglycosylated polypeptide having cellobiase activity described herein, e.g., Cel3a. In an embodiment, a functional variant has an amino acid sequence with at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to a Cel3a described herein, or a functional fragment thereof, e.g., at least 80%, at least 85%, at least 90%, at least 91%, at least 92%, at least 93%, at least 94%, at least 95%, at least 96%, at least 97%, at least 98%, or at least 99% identity to a Cel3a described herein, or a functional fragment thereof. In an embodiment, a functional variant has an amino acid sequence with at least 60%, at least 65%, at least 70%, at least 75%, at least 80%, at least 85%, at least 90%, at least 91% identity, at least 92%, at least 93%, at least 94%, at least 95%, at least 96%, at least 97%, at least 98%, or at least 99% identity to SEQ ID NO: 1, or a functional fragment thereof.

Percent identity in the context of two or more amino acid or nucleic acid sequences, refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides, 100 nucleotides, 150 nucleotides, in length. More preferably, the identity exists over a region that is at least about 200 or more amino acids, or at least about 500 or 1000 or more nucleotides, in length.

For sequence comparison, one sequence typically acts as a reference sequence, to which one or more test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

Functional variants may comprise one or more mutations, such that the variant retains cellobiase activity that is better, e.g., increased in comparison to, than the cellobiase activity of an enzyme of SEQ ID NO:1 produced by *T. reesei*. In an embodiment, the functional variant has at least 10%, at least 20%, at least 30%, at least 40%, at least 50%, at least 60%, at least 70%, at least 75%, at least 80%, at least 85%, at least 90%, at least 95%, or at least 99% (e.g., at least 80%, at least 85%, at least 90%, at least 95%, or at least 99%) of the cellobiase activity as an aglycosylated version of SEQ ID NO: 1 as produced by *E. coli*. Cellobiase activity can be tested using the functional assays described herein.

In another embodiment, the aglycosylated polypeptide differs by no more than 1, no more than 2, no more than 3, no more than 4, no more than 5, no more than 6, no more than 7, no more than 8, no more than 9, no more than 10, no more than 15, no more than 20, no more than 30, no more than 40, or no more than 50 amino acids from a reference amino acid sequence, e.g., the amino acid sequence of SEQ ID NO: 1.

The mutations present in a functional variant include amino acid substitutions, additions, and deletions. Mutations can be introduced by standard techniques known in the art, such as site-directed mutagenesis and PCR-mediated mutagenesis. The mutation may be a conservative amino acid substitution, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the polypeptide having cellobiase activity of the disclosure can be replaced with other amino acids from the same side chain family, and the resultant polypeptide retains cellobiase activity comparable (e.g., at least 80%, 85%, 90%, 95%, or 99% of the cellobiase activity) to that of the wild-type polypeptide. Alternatively, the mutation may be an amino acid substitution in which an amino acid residue is replaced with an amino acid residue having a different side chain.

Such mutations may alter or affect various enzymatic characteristics of the cellobiase. For example, such mutations may alter or affect the cellobiase activity, thermostability, optimal pH for reaction, enzyme kinetics, or substrate recognition of the cellobiase. In some embodiments, a mutation increases the cellobiase activity of the variant in comparison to the cellobiase produced by *T. reesei* and/or SEQ ID NO:1 produced in *E. coli*. In some embodiments, a mutation increases or decreases the thermostability of the variant in comparison to wild-type cellobiase and/or SEQ ID NO:1 produced in *E. coli*. In an embodiment, a mutation changes the pH range at which the variant optimally performs the cellobiase reaction in comparison to wild-type cellobiase and/or SEQ ID NO:1 produced in *E. coli*. In an embodiment, a mutation increases or decreases the kinetics of the cellobiase reaction (e.g., $k_{cat}$, $K_M$ or $K_D$) in comparison to wild-type cellobiase and/or SEQ ID NO:1 produced in *E. coli*. In an embodiment, a mutation increases or decreases the ability of the cellobiase to recognize or bind to the substrate (e.g., cellobiose) in comparison to wild-type cellobiase and/or SEQ ID NO:1 produced in *E. coli*.

The present invention also provides functional fragments of a polypeptide having cellobiase activity as described herein, e.g., Cel3a or SEQ ID NO: 1. One of ordinary skill in the art could readily envision that a fragment of a polypeptide having cellobiase activity as described herein that contains the functional domains responsible for enzymatic activity would retain functional activity, e.g., cellobiase activity, and therefore, such fragments are encompassed in the present invention. In an embodiment, the functional fragment is at least 700 amino acids, at least 650 amino acids, at least 600 amino acids, at least 550 amino acids, at least 500 amino acids, at least 450 amino acids, at least 400 amino acids, at least 350 amino acids, at least 300 amino acids, at least 250 amino acids, at least 200 amino acids, at least 150 amino acids, at least 100 amino acids, or at least 50 amino acids in length. In an embodiment, the functional fragment is 700 to 744 amino acids, 650 to 699 amino acids, 600 to 649 amino acids, 550 to 599 amino acids, 500 to 549 amino acids, 450 to 499 amino acids, 400 to 449 amino acids, 350 to 399 amino acids, 300 to 349 amino acids, 250 to 299 amino acids, 200 to 249 amino acids, 150 to 199 amino acids, 100 to 149 amino acids, or 50 to 99 amino acids. With regard to the ranges of amino acid length described above, the lowest and highest values of amino acid length are included within each disclosed range. In an embodiment, the functional fragment has at least 10%, at least 20%, at least 30%, at least 40%, at least 50%, at least 60%, at least 70%, at least 75%, at least 80%, at least 85%, at least 90%, at least 95%, or at least 99% of the cellobiase activity as wild-type Cel3a or the polypeptide comprising SEQ ID NO: 1 produced in *E. coli*.

Assays for detecting cellobiase activity are known in the art. For example, detection of the amount of glucose released from cellobiose can be determined by incubating purified cellobiase with substrate, e.g., cellobiose, D-(+)-cellobiose, and detecting the resultant amount of free glucose after completion of the reaction. The amount of free glucose can be determined using a variety of methods known in the art. For example, dilutions of purified cellobiase are prepared in a buffer containing 50 mM sodium citrate monobasic, pH 5.0 NaOH. The cellobiose substrate is added to the purified cellobiase in an amount such that the final concentration of cellobiose in the reaction mixture is 30 mM. The reaction mixture is incubated under conditions suitable for the reaction to occur, e.g., in a shaker (700 rpm) at 48° C. for 30 minutes. To stop the reaction, the reaction mixture is heated for 5 minutes at 100° C. The reaction mixture is filtered through a 0.45 µm filter and the filtrate is analyzed to quantify the amount of glucose and/or cellobiase. A YSI instrument that measures analytes such as glucose can be used to determine the concentration of glucose produced from the reaction. Alternatively, UPLC (Ultra Performance Liquid Chromatography) can be used to determine the concentration of glucose and cellobiose from the reaction. This assay can be formatted in a single reaction or in multiple reaction formats, e.g., 96 well format. In some embodiments, the multiple reaction format may be preferred to generate an activity curve representing cellobiase activity with respect to different concentrations of the purified cellobiase. The concentration of the purified cellobiase can be determined using a standard Bradford assay. Dilutions of the purified cellobiase assay are prepared, e.g., 2-fold dilutions, and are aliquoted into a 96 well plate, e.g., 12 wells of 2-fold dilutions. Cellobiose substrate is added as previously described, such that the final concentration of cellobiase in the reaction is 30 mM. The plate is sealed and treated under conditions sufficient for the cellobiase reaction to occur, and then under conditions to stop the reaction. The reaction is then filtered through a 96 well format 0.45 µm membrane (e.g., Durapore) and analyzed by YSI and/or HPLC methods, e.g., UPLC.

This activity assay can also be used to determine the concentration, or titer, of a Cel3a in a sample by generating a standard curve of activity of dilutions of a Cel3a sample with a known concentration. The activity of dilutions of the sample with unknown concentration is determined and compared with the standard curve to identify an approximate concentration based on the standard curve. This method is described in further detail in Example 6.

In other embodiments, a colorimetric/fluorometric assay can be used. The purified cellobiase is incubated with substrate cellobiose under conditions for the reaction to occur. Detection of the product glucose is as follows. Glucose oxidase is added to the mixture, which oxidizes glucose (the product) to gluconic acid and hydrogen peroxide. Peroxidase and o-dianisidine is then added. 0-dianisidine reacts with the hydrogen peroxide in the presence of peroxidase to form a colored product. Sulfuric acid is added, which reacts with the oxidized o-dianisidine reacts to form a more stable colored product. The intensity of the color when measured, e.g., by spectrophotometer or colorimeter, e.g., at 540 nm, is directly proportional to the glucose concentration. Such colorimetric/fluorometric glucose assays are commercially available, for example from Sigma Aldrich, Catalog No. GAGO-20.

For all of the polypeptides having cellobiase activity described above, the polypeptides are aglycosylated using the methods for producing aglycosylated polypeptides described herein.

Glycosylation is the enzymatic process by which a carbohydrate is attached to a glycosyl acceptor, e.g., the nitrogen of arginine or asparginine side chains or the hydroxyl oxygen of serine, threonine, or tyrosine side chains. There are two types of glycosylation: N-linked and O-linked glycosylation. N-linked glycosylation occurs at consensus site Asn-X-Ser/Thr, wherein the X can be any amino acid except a proline. O-linked glycosylation occurs at Ser/Thr residues. Glycosylation sites can be predicted using various algorithms known in the art, such as Prosite, publicly available by the Swiss Institute of Bioinformatics, and NetNGlyc 1.0 or NetOGlyc 4.0, publicly available by the Center for Biological Sequence Analysis.

In embodiments, the functional variant contains one or more mutations wherein one or more glycoslyation sites present in the Cel3a polypeptide expressed by a nucleic acid sequence described herein that has been mutated such that a glycan can no longer be attached or linked to the glycosylation site. In another embodiment, the functional variant contains one or more mutations proximal to one or more glycosylation sites present in the Cel3a polypeptide expressed by a nucleic acid sequence described herein that has been mutated such that a glycan can no longer be attached or linked to the glycosylation site. For example, the mutation proximal to a glycosylation site mutates the consensus motif recognized by the glycosylating enzyme, or changes the conformation of the polypeptide such that the polypeptide cannot be glycosylated, e.g., the glycoslation site is hidden or steric hindrance due to the new conformation prevents the glycosylating enzymes from accessing the glycosylation site. A mutation proximal to a glycosylation site in the Cel3a polypeptide is directly adjacent to, or at least 2, at least 3, at least 4, at least 5, at least 6, at least 7, at least 8, at least 9, at least 10, at least 15, at least 20, at least 30 or at least 40 amino acids from the glycosylation site that, as a result of the proximal mutation, will not be glycosylated.

In an embodiment, one or more of the following glycosylation sites of Cel3a, or SEQ ID NO: 1, are mutated: the threonine at amino acid position 78, the threonine at amino acid position 241, the serine at amino acid position 343, the serine at amino acid position 450, the threonine at amino acid position 599, the serine at amino acid position 616, the threonine at amino acid position 691, the serine at amino acid position 21, the threonine at amino acid position 24, the serine at amino acid position 25, the serine at amino acid position 28, the threonine at amino acid position 38, the threonine at amino acid position 42, the threonine at amino acid position 303, the serine at amino acid position at 398, the at serine amino acid position 435, the serine at amino acid position 436, the threonine at amino acid position 439, threonine at amino acid position 442, the threonine at amino acid position 446, the serine at amino acid position 451, the serine at amino acid position 619, the serine at amino acid position 622, the threonine at amino acid position 623, the serine at amino acid position 626, or the threonine at amino acid position 630, or any combination thereof. In embodiments, the glycosylation site is mutated from a serine or threonine to an alanine. For example, the aglycosylated polypeptide described herein has one or more of the following mutations: T78A, T241A, S343A, S450A, T599A, S616A, T691A, S21A, T24A, S25A, S28A, T38A, T42A, T303A, T398A, S435A, S436A, T439A, T442A, T446A, S451A, S619A, S622A, T623A, S626A, or T630A, or any combination thereof. Alternatively, one or more amino acids proximal to the glycosylation sites described above is mutated.

Assays to detect whether a polypeptide is modified by a glycan (e.g., whether the polypeptide is glycosylated or aglycosylated) are known in the art. The polypeptide can be purified or isolated and can be stained for detection and quantification of glycan moieties, or the polypeptide can be analyzed by mass spectrometry, and compared to a corresponding reference polypeptide. The reference polypeptide has the same primary sequence as the test polypeptide (of which the glycosylation state is to be determined), but is either glycosylated or aglycosylated.

The aglycosylated polypeptides described herein have increased cellobiase activity compared to a corresponding glycosylated polypeptide, e.g., glycosylated Cel3a polypeptide. For example, the aglycosylated polypeptide having cellobiase activity has at least 1%, 2%, 5%, 10%, 15%, 20%, 25%, 30%, 40%, 50%, 60%, 70%, 80%, 90%, 100%, or 200% cellobiase activity compared to the glyocyosylated polypeptide.

Nucleic Acids

The present invention also provides a nucleic acid sequence encoding a polypeptide having cellobiase activity of the present invention. In an embodiment, the nucleic acid sequence encodes a Cel3a enzyme or a functional fragment thereof with the amino acid sequence described herein.

In an embodiment, the nucleic acid sequence that encodes Cel3a is provided below:

```
(SEQ ID NO: 2)
ATGCGTTACCGAACAGCAGCTGCGCTGGCACTTGCCACTGGGCCCTTTGC
TAGGGCAGACAGTCACTCAACATCGGGGGCCTCGGCTGAGGCAGTTGTAC
CTCCTGCAGGGACTCCATGGGGAACCGCGTACGACAAGGCGAAGGCCGCA
TTGGCAAAGCTCAATCTCCAAGATAAGGTCGGCATCGTGAGCGGTGTCGG
CTGGAACGGCGGTCCTTGCGTTGGAAACACATCTCCGGCCTCCAAGATCA
GCTATCCATCGCTATGCCTTCAAGACGGACCCCTCGGTGTTCGATACTCG
ACAGGCAGCACAGCCTTTACGCCGGGCGTTCAAGCGGCCTCGACGTGGGA
TGTCAATTTGATCCGCGAACGTGGACAGTTCATCGGTGAGGAGGTGAAGG
CCTCGGGGATTCATGTCATACTTGGTCCTGTGGCTGGGCCGCTGGGAAAG
ACTCCGCAGGGCGGTCGCAACTGGGAGGGCTTCGGTGTCGATCCATATCT
CACGGGCATTGCCATGGGTCAAACCATCAACGGCATCCAGTCGGTAGGCG
TGCAGGCGACAGCGAAGCACTATATCCTCAACGAGCAGGAGCTCAATCGA
GAAACCATTTCGAGCAACCCAGATGACCGAACTCTCCATGAGCTGTATAC
TTGGCCATTTGCCGACGCGGTTCAGGCCAATGTCGCTTCTGTCATGTGCT
CGTACAACAAGGTCAATACCACCTGGGCCTGCGAGGATCAGTACACGCTG
CAGACTGTGCTGAAAGACCAGCTGGGGTTCCCAGGCTATGTCATGACGGA
CTGGAACGCACAGCACACGACTGTCCAAAGCGCGAATTCTGGGCTTGACA
TGTCAATGCCTGGCACAGACTTCAACGGTAACAATCGGCTCTGGGGTCCA
GCTCTCACCAATGCGGTAAATAGCAATCAGGTCCCCACGAGCAGAGTCGA
CGATATGGTGACTCGTATCCTCGCCGCATGGTACTTGACAGGCCAGGACC
AGGCAGGCTATCCGTCGTTCAACATCAGCAGAAATGTTCAAGGAAACCAC
AAGACCAATGTCAGGGCAATTGCCAGGGACGGCATCGTTCTGCTCAAGAA
TGACGCCAACATCCTGCCGCTCAAGAAGCCCGCTAGCATTGCCGTCGTTG
GATCTGCCGCAATCATTGGTAACCACGCCAGAAACTCGCCCTCGTGCAAC
GACAAAGGCTGCGACGACGGGGCCTTGGGCATGGGTTGGGGTTCCGGCGC
CGTCAACTATCCGTACTTCGTCGCGCCCTACGATGCCATCAATACCAGAG
CGTCTTCGCAGGGCACCCAGGTTACCTTGAGCAACACCGACAACACGTCC
TCAGGCGCATCTGCAGCAAGAGGAAAGGACGTCGCCATCGTCTTCATCAC
CGCCGACTCGGGTGAAGGCTACATCACCGTGGAGGGCAACGCGGGCGATC
GCAACAACCTGGATCCGTGGCACAACGGCAATGCCCTGGTCCAGGCGGTG
GCCGGTGCCAACAGCAACGTCATTGTTGTTGTCCACTCCGTTGGCGCCAT
```

```
CATTCTGGAGCAGATTCTTGCTCTTCCGCAGGTCAAGGCCGTTGTCTGGG
CGGGTCTTCCTTCTCAGGAGAGCGGCAATGCGCTCGTCGACGTGCTGTGG
GGAGATGTCAGCCCTTCTGGCAAGCTGGTGTACACCATTGCGAAGAGCCC
CAATGACTATAACACTCGCATCGTTTCCGGCGGCAGTGACAGCTTCAGCG
AGGGACTGTTCATCGACTATAAGCACTTCGACGACGCCAATATCACGCCG
CGGGTACGAGTTCGGCTATGGACTGTCTTACACCAAGTTCAACTACTCACG
CCTCTCCGTCTTGTCGACCGCCAAGTCTGGTCCTGCGACTGGGGCCGTTG
TGCCGGGAGGCCCGAGTGATCTGTTCCAGAATGTCGCGACAGTCACCGTT
GACATCGCAAACTCTGGCCAAGTGACTGGTGCCGAGGTAGCCCAGCTGTA
CATCACCTACCCATCTTCAGCACCCAGGACCCCTCCGAAGCAGCTGCGAG
GCTTTGCCAAGCTGAACCTCACGCCTGGTCAGAGCGGAACAGCAACGTTC
AACATCCGACGACGAGATCTCAGCTACTGGGACACGGCTTCGCAGAAATG
GGTGGTGCCGTCGGGGTCGTTTGGCATCAGCGTGGGAGCGAGCAGCCGGG
ATATCAGGCTGACGAGCACTCTGTCGGTAGCG
```

The nucleic acid sequence encoding the polypeptide with cellobiase activity described herein can be codon-optimized for increased expression in host cells. Codon optimization includes changing the nucleic acid sequence to take into consideration factors including codon usage bias, cryptic splicing sites, mRNA secondary structure, premature polyA sites, interaction of codon and anti-codon, and RNA instability motifs, to increase expression of the encoded polypeptide in the host. Various algorithms and commercial services for codon-optimization are known and available in the art.

The codon-optimized nucleic acid sequence that encodes Cel3a is provided below:

```
(SEQ ID NO: 3)
ATGCGTTATCGTACAGCCGCAGCCCTGGCACTGGCCACAGGTCCGTTCGC
ACGTGCCGATAGTCACAGTACCAGCGGTGCCAGCGCAGAAGCCGTGGTTC
CGCCGGCAGGCACACCGTGGGGCACAGCCTATGATAAAGCCAAAGCCGCC
CTGGCCAAGCTGAATCTGCAGGATAAAGTGGGCATCGTGAGTGGCGTGGG
CTGGAACGGTGGTCCGTGCGTTGGCAACACCAGCCCGGCAAGCAAGATCA
GCTATCCGAGCTTATGCCTGCAGGATGGTCCGCTGGGCGTGCGCTATAGC
ACCGGTAGTACCGCCTTTACACCTGGTGTGCAGGCCGCCAGTACCTGGGA
CGTTAACCTGATCCGCGAACGTGGCCAATTTATCGGCGAAGAAGTTAAAG
CCAGCGGCATTCATGTTATTCTGGGTCCGGTGGCCGGTCCTCTGGGTAAA
ACCCCGCAGGGCGGCCGTAATTGGGAAGGCTTCGGCGTTGATCCGTATTT
AACCGGCATCGCAATGGGCCAGACCATTAATGGCATCCAGAGCGTGGGTG
TTCAAGCCACCGCCAAACACTACATATTAAACGAACAGGAACTGAATCGT
GAAACCATCAGCAGCAATCCGGATGATCGCACCCTGCATGAGCTGTATAC
ATGGCCTTTTGCCGACGCAGTTCAGGCCAACGTGGCAAGTGTGATGTGTA
GCTATAACAAGGTGAACACCACCTGGGCCTGCGAAGACCAGTACACCCTG
CAGACCGTTTTAAAAGACCAACTGGGCTTCCCTGGTTACGTGATGACAGA
TTGGAATGCCCAGCACACAACCGTTCAGAGCGCAAACAGTGGCCTGGATA
```

-continued

```
TGAGCATGCCGGGCACCGACTTCAACGGCAATAATCGTCTGTGGGGTCCG
GCACTGACCAATGCCGTTAACAGCAACCAGGTGCCGACCAGTCGTGTGGA
CGATATGGTTACCCGTATTCTGGCCGCCTGGTACCTGACAGGTCAAGACC
AGGCCGGCTACCCGAGCTTCAACATCAGCCGCAACGTGCAGGGTAATCAC
AAGACCAACGTTCGCGCAATCGCACGCGATGGTATCGTGCTGTTAAAGAA
CGATGCCAACATTCTGCCGCTGAAAAAACCGGCCAGCATCGCCGTTGTTG
GTAGCGCAGCCATCATTGGCAACCACGCCCGTAACAGTCCGAGCTGCAAT
GATAAAGGCTGTGACGACGGTGCCCTGGGCATGGGTTGGGGTAGTGGTGC
CGTGAACTACCCGTATTTCGTGGCCCCGTACGACGCCATTAACACCCGTG
CAAGTAGCCAGGGTACCCAGGTTACCCTGAGCAACACCGACAACACAAGC
AGCGGTGCCAGTGCAGCACGTGGTAAGGATGTGGCCATCGTGTTCATCAC
CGCCGACAGCGGCGAAGGCTACATTACCGTGGAGGGTAATGCCGGTGATC
GCAATAATCTGGACCCGTGGCATAACGGCAACGCCCTGGTTCAGGCAGTG
GCAGGCGCAAATAGCAACGTGATCGTTGTGGTGCATAGCGTGGGTGCCAT
CATTCTGGAGCAGATCCTGGCCCTGCCGCAAGTTAAGGCAGTTGTGTGGG
CAGGTCTGCCGAGCCAAGAAAGTGGCAATGCCCTGGTGGACGTTCTGTGG
GGCGATGTTAGTCCGAGCGGCAAGCTGGTGTATACAATCGCCAAGAGCCC
GAACGACTATAACACCCGCATCGTTAGCGGCGGCAGTGATAGCTTCAGCG
AGGGCCTGTTTATCGACTACAAGCATTTCGATGATGCCAATATTACCCCG
CGCTACGAATTTGGTTATGGCCTGAGCTATACCAAGTTCAACTACAGCCG
CCTGAGCGTTTTAAGTACCGCCAAGAGTGGTCCGGCAACAGGTGCCGTGG
TTCCTGGTGGTCCGAGTGATCTGTTTCAGAATGTGGCCACCGTGACCGTG
GATATCGCCAACAGTGGTCAGGTTACCGGCGCCGAAGTGGCACAGCTGTA
CATCACCTATCCGAGCAGTGCACCGCGCACCCCGCCGAAACAGCTGCGTG
GCTTCGCCAAATTAAACCTGACCCCGGGCCAGAGCGGTACAGCAACCTTC
AATATTCGCCGCCGTGATCTGAGCTATTGGGACACCGCCAGCCAAAAATG
GGTGGTGCCGAGCGGCAGCTTTGGCATTAGTGTGGGTGCAAGTAGCCGCG
ACATTCGCTTAACAAGCACCCTGAGTGTTGCC
```

In an embodiment, the nucleic acid sequence encoding a Cel3a enzyme or functional variant thereof comprises at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 2. In an embodiment, the nucleic acid sequence encoding a Cel3a enzyme or functional variant thereof comprises at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO:2 or SEQ ID NO: 3.

Provided herein is a nucleic acid sequence encoding an aglycosylated polypeptide, e.g., Cel3a polypeptide, as described above, in which one or more glycoslyation sites present in the polypeptide has been mutated such that a glycan can no longer be attached or linked to the glycosylation site. In another embodiment, the nucleic acid sequence described herein encoding an aglycosylated polypeptide, e.g., a Cel3a polypeptide, as described above, in which one or more mutations proximal to one or more glycosylation sites present in the polypeptide has been mutated such that a glycan can no longer be attached or linked to the glycosylation site, as previously described. In an embodiment, the nucleic acid sequence encodes a polypeptide comprising one or more mutations at one or more of the following glycosylation sites of Cel3a, or SEQ ID NO: 1: the threonine at amino acid position 78, the threonine at amino acid position 241, the serine at amino acid position 343, the serine at amino acid position 450, the threonine at amino acid position 599, the serine at amino acid position 616, the threonine at amino acid position 691, the serine at amino acid position 21, the threonine at amino acid position 24, the serine at amino acid position 25, the serine at amino acid position 28, the threonine at amino acid position 38, the threonine at amino acid position 42, the threonine at amino acid position 303, the serine at amino acid position at 398, the at serine amino acid position 435, the serine at amino acid position 436, the threonine at amino acid position 439, threonine at amino acid position 442, the threonine at amino acid position 446, the serine at amino acid position 451, the serine at amino acid position 619, the serine at amino acid position 622, the threonine at amino acid position 623, the serine at amino acid position 626, or the threonine at amino acid position 630, or any combination thereof. In embodiments, the glycosylation site is mutated from a serine or threonine to an alanine. For example, the nucleic acid sequence of the invention encodes an aglycosylated polypeptide comprising one or more of the following mutations: T78A, T241A, S343A, S450A, T599A, S616A, T691A, S21A, T24A, S25A, S28A, T38A, T42A, T303A, T398A, S435A, S436A, T439A, T442A, T446A, S451A, S619A, S622A, T623A, S626A, or T630A, or any combination thereof. The ordinarily skilled artisan could readily modify the nucleic acid sequence of wild-type Cel3a (SEQ ID NO: 2) to encode a polypeptide with one or more glycosylation site mutation by using methods known in the art, such as site-directed mutagenesis.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other amplification procedures such as ligase chain reaction (LCR), ligated activated transcription (LAT) and nucleotide sequence-based amplification (NASBA) may be used. The nucleic acid sequence may be cloned from a strain of *Trichoderma reesei*, e.g., wild-type *T. reesei*, or *T. reesei* RUTC30, or another or related organism and thus, for example, may be an allelic or species variant of the polypeptide encoding region of the nucleic acid sequence.

The nucleic acid sequence may be obtained by standard cloning procedures used in genetic engineering to relocate the nucleic acid sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

Expression Vectors and Host Cells

The present invention also provides nucleic acid constructs comprising a nucleic acid sequence encoding the polypeptide having cellobiase activity described herein operably linked to one or more control sequences that direct the expression, secretion, and/or isolation of the expressed polypeptide.

As used herein, an "expression vector" is a nucleic acid construct for introducing and expressing a nucleic acid sequence of interest into a host cell. In some embodiments, the vector comprises a suitable control sequence operably linked to and capable of effecting the expression of the polypeptide encoded in the nucleic acid sequence of interest. The control sequence may be an appropriate promoter sequence, recognized by a host cell for expression of the nucleic acid sequence. In an embodiment, the nucleic acid sequence of interest is a nucleic acid sequence encoding a polypeptide having cellobiase activity as described herein.

A promoter in the expression vector of the invention can include promoters obtained from genes encoding extracellular or intracellular polypeptides either homologous or heterologous to the host cell, mutant promoters, truncated promoters, and hybrid promoters.

Examples of suitable promoters for directing transcription of the nucleic acid constructs of the present invention in a bacterial host cell are the promoters obtained from the *E. coli* lac operon, *E. coli* tac promoter (hybrid promoter, DeBoer et al, PNAS, 1983, 80:21-25), *E. coli* rec A, *E. coli* araBAD, *E. coli* tetA, and prokaryotic beta-lactamase. Other examples of suitable promoters include viral promoters, such as promoters from bacteriophages, including a T7 promoter, a T5 promoter, a T3 promoter, an M13 promoter, and a SP6 promoter. In some embodiments, more than one promoter controls the expression of the nucleic acid sequence of interest, e.g., an *E. coli* lac promoter and a T7 promoter. Further promoters that may be suitable for use in the present invention are described in "Useful proteins from recombinant bacteria" in Scientific American, 1980, 242: 74-94, and Sambrook et al., Molecular Cloning: A Laboratory Manual, 1989. In some preferred embodiments, the promoter is inducible, where the addition of a molecule stimulates the transcription and expression of the downstream reading frame.

Examples of suitable promoters for directing transcription of the nucleic acid constructs of the present invention in a eukaryotic host cell, e.g., in a fungal or yeast cell are promoters obtained from the genes of *Trichoderma Reesei*, methanol-inducible alcohol oxidase (AOX promoter), *Aspergillus nidulans* tryptophan biosynthesis (trpC promoter), *Aspergillus niger* var. *awamori* flucoamylase (glaA), *Saccharomyces cerevisiae* galactokinase (GAL1), or *Kluyveromyces lactis* Plac4-PBI promoter.

A control sequence present in the expression vector of the present invention may also be a signal sequence that codes for an amino acid sequence linked to the amino terminus of a polypeptide and directs the encoded polypeptide into the cell's secretory pathway, e.g., a secretion signal sequence. The signal sequence may be an endogenous signal sequence, e.g., where the signal sequence is present at the N-terminus of the wild-type polypeptide when endogenously expressed by the organism from which the polypeptide of interest originates from. The signal sequence may be a foreign, or heterologous, signal peptide, in which the signal sequence is from a different organism or a different polypeptide than that of the polypeptide of interest being expressed. Any signal sequence which directs the expressed polypeptide into the secretory pathway of a host cell may be used in the present invention. Typically, signal sequences are composed of between 6 and 136 basic and/or hycrophobic amino acids.

Examples of signal sequences suitable for the present invention include the signal sequence from *Saccharomyces cerevisiae* alpha-factor.

Fusion tags may also be used in the expression vector of the present invention to facilitate the detection and purification of the expressed polypeptide. Examples of suitable fusion tags include His-tag (e.g., 3×His, 6×His (SEQ ID NO: 6), or 8×His (SEQ ID NO: 7)), GST-tag, HSV-tag, S-tag, T7 tag. Other suitable fusion tags include myc tag, hemagglutinin (HA) tag, and fluorescent protein tags (e.g., green fluorescent protein). The fusion tag is typically operably linked to the N or C terminus of the polypeptide to be expressed. In some embodiments, there may be a linker region between the fusion tag sequence and the N-terminus or C-terminus of the polypeptide to be expressed. In an embodiment, the linker region comprises a sequence between 1 to 20 amino acids, that does not affect or alter the expression or function of the expressed polypeptide.

Utilization of the fusion tags described herein allows detection of the expressed protein, e.g., by western blot by using antibodies that specifically recognize the tag. The tags also allows for purification of the expressed polypeptide from the host cell, e.g., by affinity chromatography. For example, an expressed polypeptide fused to a His-tag can be purified by using nickel affinity chromatography. The His tag has affinity for the Nickel ions, and a nickel column will retain the his-tagged polypeptide, while allowing all other proteins and cell debris to flow through the column. Elution of the His-tagged polypeptide using an elution buffer, e.g., containing imidazole, releases the His-tagged polypeptide from the column, resulting in substantially purified polypeptide.

The expression vector of the invention may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. For example, the selectable marker gene may confer resistance to ampicillin, chloramphenicol, tetracycline, kanamycin, hygromycin, phleomycin, geneticin, or G418, or may complement a deficiency of the host microbe in one of the trp, arg, leu, pyr4, pyr, ura3, ura5, his, or ade genes or may confer the ability to grow on acetamide as a sole nitrogen source.

The expression vector of the invention may further comprise other nucleic acid sequences, e.g., additional control sequences, as is commonly known to those of skill in the art, for example, transcriptional terminators, synthetic sequences to link the various other nucleic acid sequences together, origins of replication, ribosome binding sites, a multiple cloning site (or polylinker site), a polyadenylation signal and the like. The ribosomal binding site suitable for the expression vector depends on the host cell used, for example, for expression in a prokaryotic host cell, a prokaryotic RBS, e.g., a T7 phage RBS can be used. A multiple cloning site, or polylinker site, contains one or more restriction enzyme sites that are preferably not present in the remaining sequence of the expression vector. The restriction enzyme sites are utilized for the insertion of a nucleic acid sequence encoding a polypeptide having cellobiase activity or other desired control sequences. The practice of the present invention is not limited by the presence of any one or more of these other nucleic acid sequences, e.g., other control sequences.

Examples of suitable expression vectors for use in the present invention include vectors for expression in prokaryotes, e.g., bacterial expression vectors. A bacterial expression vector suitable for use in the present invention in the pET vector (Novagen), which contains the following: a viral T7 promoter which is specific to only T7 RNA polymerase (not bacterial RNA polymerase) and also does not occur anywhere in the prokaryotic genome, a lac operator comprising a lac promoter and coding sequence for the lac repressor protein (lad gene), a polylinker, an f1 origin of replication (so that a single-stranded plasmid can be produced when co-infected with M13 helper phage), an ampicillin resistance gene, and a ColE1 origin of replication (Blaber, 1998). Both the promoter and the lac operator are located 5', or upstream, of the polylinker in which the nucleic acid sequence encoding a polypeptide described herein is inserted. The lac operator confers inducible expression of the nucleic acid sequence encoding a polypeptide having cellobiase activity. Addition of IPTG (Isopropyl β-D-1-thiogalactopyranoside), a lactose metabolite, triggers transcription of the lac operon and induces protein expression of the nucleic acid sequence under control of the lac operator. Use of this system requires the addition of T7 RNA polymerase to the host cell for vector expression. The T7 RNA polymerase can be introduced via a second expression vector, or a host cell strain that is genetically engineered to express T7 RNA polymerase can be used.

An exemplary expression vector for use with the invention is a pET vector, commercially available from Novagen. The pET expression system is described in U.S. Pat. Nos. 4,952,496; 5,693,489; and 5,869,320. In one embodiment, the pET vector is a pET-DUET vector, e.g., pET-Duet1, commercially available from Novagen. Other vectors suitable for use in the present invention include vectors containing His-tag sequences, such as those described in U.S. Pat. Nos. 5,310,663 and 5,284,933; and European Patent No. 282042.

The present invention also relates to a host cell comprising the nucleic acid sequence or expression vector of the invention, which are used in the recombinant production of the polypeptides having cellobiase activity.

An expression vector comprising a nucleic acid sequence of the present invention is introduced into a host cell so that the vector is maintained (e.g., by chromosomal integration or as a self-replicating extra-chromosomal vector) such that the polypeptide is expressed.

The host cell may be a prokaryote or a eukaryote. The host cell may be a bacteria, such as an *E. coli* strain, e.g., K12 strains NovaBlue, NovaBlue T1R, JM109, and DH5α. Preferably, the bacteria cell has the capability to fold, or partially fold, exogenously expressed proteins, such as *E. coli* Origami strains, e.g., Origami B, Origami B (DE3), Origami 2, and Origami 2(DE3) strains. In some embodiments, it may be preferred to use a host cell that is deficient for glycosylation, or has an impaired glycosylation pathway such that proteins expressed by the host cell are not significantly glycosylated.

The host cell may be a yeast or a filamentous fungus, particularly those classified as Ascomycota. Genera of yeasts useful as host microbes for the expression of modified TrCel3A beta-glucosidases of the present invention include *Saccharomyces*, *Pichia*, *Hansenula*, *Kluyveromyces*, *Yarrowia*, and *Arxula*. Genera of fungi useful as microbes for the expression of the polypeptides of the present invention include *Trichoderma*, *Hypocrea*, *Aspergillus*, *Fusarium*, *Humicola*, *Neurospora*, *Chrysosporium*, *Myceliophthora*, *Thielavia*, *Sporotrichum* and *Penicillium*. For example, the host cell may be *Pichia pastoris*. For example, the host cell may be an industrial strain of *Trichoderma reesei*, or a mutant thereof, e.g., *T. reesei* RUTC30. Typically, the host cell is one which does not express a parental cellobiase or Cel3a.

The selection of the particular host cell, e.g., bacterial cell or a fungal cell, depends on the expression vector (e.g., the control sequences) and/or the method utilized for producing an aglycosylated polypeptide of the invention, as described in further detail below.

The expression vector of the invention may be introduced into the host cell by any number of methods known by one skilled in the art of microbial transformation, including but not limited to, transformation, treatment of cells with $CaCl_2$, electroporation, biolistic bombardment, lipofection, and PEG-mediated fusion of protoplasts (e.g. White et al., WO 2005/093072, which is incorporated herein by reference). After selecting the recombinant host cells containing the expression vector (e.g., by selection utilizing the selectable marker of the expression vector), the recombinant host cells may be cultured under conditions that induce the expression of the polypeptide having cellobiase activity of the invention.

Methods for Producing Aglycosylated Polypeptides

The present invention further provides methods for producing an aglycosylated polypeptide having cellobiase activity, as described herein. The method comprises culturing the recombinant host cell expressing the polypeptide of the present invention under conditions suitable for the expression of the polypeptide. The method may also comprise recovering the aglycosylated polypeptide from the recombinant host cell.

Methods for recovering polypeptides expressed from prokaryote and eukaryote cells are known in the art. In embodiments, the method for recovering the polypeptide comprises lysing the cells, e.g., by mechanical, chemical, or enzymatic means. For example, cells can be physically broken apart, e.g., by sonication, milling (shaking with beads), or shear forces. Cell membranes can be treated such that they are permeabilized such that the contents of the cells are released, such as treatment with detergents, e.g., Triton, NP-40, or SDS. Cells with cell walls, e.g., bacterial cells, can be permeabilized using enzymes, such as a lysozyme or lysonase. Any combination of the mechanical, chemical, and enzymatic techniques described above are also suitable for recovering expressed polypeptides of interest from the host cell in the context of this invention. For example, when expressing an aglycosylated polypeptide having cellobiase activity described herein in a bacterial cell, e.g., an *E. coli* cell, the cell is typically lysed by centrifuging and pelleting the cell culture, and resuspending in a lysis buffer containing lysozyme. To ensure complete lysis, the resuspended cells are subjected to one of the following methods: sonication, milling, or homogenization.

In one embodiment, the expressed aglycosylated polypeptides having cellobiase activity described herein are not lysed before addition to the biomass for the saccharification reaction. In some instances, the methods for lysing host cells can result in protein denaturation and/or decreased enzyme activity, which leads to increased cost of downstream processing. Thus, the present invention also provides methods for directly adding the host cells expressing an aglycosylated polypeptide having cellobiase activity described herein to the biomass prior to the saccharification step.

In an embodiment, the host cell, e.g., the *E. coli* cell, expressing the aglycosylated polypeptide having cellobiase activity described herein is isolated, e.g., by centrifugation, and added to the saccharification reaction, e.g., the saccharification reactor containing biomass. The cells are lysed by a combination of shear from the biomass, the impellers, and the increased temperature. In an embodiment, the culture of host cell, e.g., the *E. coli* cell, expressing the aglycosylated polypeptide having cellobiase activity described herein is added directly from the fermentation tank directly to the saccharification tank and eliminating the need to pellet cells by centrifugation.

Using a Host Cell Deficient for Glycosylation

In embodiments, the expression vector comprises a nucleic acid sequence encoding a polypeptide having cellobiase activity described herein operably linked to a fusion tag is introduced to and expressed in a cell that does not significantly glycosylate proteins expressed in the cell, e.g., a bacterial host cell. The recombinant host cell is cultured under conditions for expression of the polypeptide, resulting in the production of an aglycosylated polypeptide having cellobiase activity. The aglycosylated polypeptide can be purified or isolated from the host cell using affinity chromatography methods for the fusion tag as described herein.

For example, in this embodiment, the expression vector contains a lac operator and a T7 promoter upstream of the nucleic acid sequence encoding a polypeptide having cellobiase activity, and the host cell has the capacity to express T7 RNA polymerase. Expression of the polypeptide having cellobiase activity is induced by addition of IPTG. Preferably, the host cell is an *E. coli* cell, preferably an *E. coli* Origami cell. In this embodiment, the fusion tag is a His-tag, and the purification of the expressed aglycosylated polypeptide comprises nickel affinity chromatography.

Using a Host Cell with the Capacity for Glycosylation

In another embodiment, an expression vector comprising a nucleic acid sequence encoding a polypeptide comprising one or more glycosylation site mutations such that the polypeptide is not glyscosylated, as described herein, is expressed in a host cell, wherein the host cell is capable of glycosylating proteins expressed within the cell, e.g., a yeast or fungal host cell. Alternatively, the host cell is not capable of glycosylating proteins expressed within the cell, e.g., a bacterial host cell. In this embodiment, the polypeptide is operably linked to a fusion tag. The aglycosylated polypeptide can be purified or isolated from the bacterial host cell using affinity chromatography methods for the fusion tag as described herein.

In yet another embodiment, an expression vector comprising a nucleic acid sequence encoding a polypeptide having cellobiase activity described herein is expressed in a host cell, wherein the host cell is capable of glycosylating proteins expressed within the cell. The cells are cultured under conditions sufficient for expression and glycosylation of the polypeptide. In this embodiment, the polypeptide is operably linked to a fusion tag. The glycosylated polypeptide can be purified or isolated from the bacterial host cell using affinity chromatography methods for the fusion tag as described herein. After purification from the host cells and other endogenous host enzymes, e.g., glycosylation enzymes, the glycans of the isolated glycosylated polypeptide can be removed by incubation with deglycosylating enzymes. Deglycosylating enzymes include PNGase F, PNGase A, EndoH (endoglycosidase H), EndoS (endoglycosidase S), EndoD (endoglycosidase D), EndoF (endoglycosidase F), EndoF1 (endoglycosidase F1), or EndoF2 (endoglycosidase F2). Protein deglycosylation mixes containing enzymes sufficient for the complete removal of glycans are commercially available, e.g., from New England Biolabs. The isolated polypeptide is incubated with one or more deglycosylating enzyme under conditions sufficient for the removal of all of the glycans from the polypeptide. Other methods are known in the art for removing glycans from a polypeptide, e.g., β-elimination with mild alkali or mild hydrazinolysis. Assessment of the glycosylation state of the polypeptide can be determined using methods for staining and visualization of glycans known in the art, or mass spectrometry.

In yet another embodiment, an expression vector comprising a nucleic acid sequence encoding a polypeptide having cellobiase activity described herein is expressed in a host cell, wherein the host cell is capable of glycosylating proteins expressed within the cell. The cells are cultured under conditions sufficient for expression of the polypeptide, but in the presence of glycosylation inhibitors. The glycosylation inhibitors are present at a concentration and for a sufficient time such that the expressed polypeptides are not glycosylated. In this embodiment, the polypeptide is operably linked to a fusion tag. The resulting aglycosylated polypeptide can be purified or isolated from the bacterial host cell using affinity chromatography methods for the fusion tag as described herein.

Examples of suitable glycosylation inhibitors for use in this embodiment include tunicamycin, Benzyl-GalNAc (Benzyl 2-acetamido-2-deoxy-α-D-galactopyranoside), 2-Fluoro-2-deoxy-D-glucose, and 5'CDP (5' cytidylate diphosphate). In some embodiments, a combination of glycosylation inhibitors is used. Preferably, the concentration of glycosylation inhibitors used in this embodiment is sufficient to inhibit glycosylation of the polypeptide, but do not cause cytotoxicity or inhibition of protein expression of the host cell.

Methods of Producing Products Using Aglycosylated Polypeptides

The present invention provides methods and compositions for converting or processing a biomass into products, using an aglycosylated polypeptide having cellobiase activity, as described herein. Methods for converting a biomass to products, such as sugar products, are known in the art, for example, as described in US Patent Application 2014/0011258, the contents of which are incorporated by reference in its entirety. Briefly, a biomass is optimally pretreated, e.g., to reduce the recalcitrance, and saccharified by a saccharification process that involves incubating the treated biomass with biomass-degrading, or cellulolytic, enzymes to produce sugars (e.g., glucose and/or xylose). The sugar products can then be further processed to produce a final product, e.g., by fermentation or distillation. Final products include alcohols (e.g., ethanol, isobutanol, or n-butanol), sugar alcohols (e.g., erythritol, xylitol, or sorbitol), or organic acids (e.g., lactic acid, pyurvic acid, succinic acid).

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, cellobiose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutane, pentane, n-hexane, biodiesel, bio-gasoline and mixtures thereof), co-products, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols and polyols (e.g., glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Biomass

The biomass to be processed using the methods described herein is a starchy material and/or a cellulosic material comprising cellulose, e.g., a lignocellulosic material. The biomass may also comprise hemicellulose and/or lignin. The biomass can comprise one or more of an agricultural product or waste, a paper product or waste, a forestry product, or a general waste, or any combination thereof. An agricultural product or waste comprises material that can be cultivated, harvested, or processed for use or consumption, e.g., by humans or animals, or any intermediate, byproduct, or waste that is generated from the cultivation, harvest, or processing methods. Agricultural products or waste include, but are not limited to, sugar cane, jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof. A paper product or waste comprises material that is used to make a paper product, any paper product, or any intermediate, byproduct or waste that is generated from making or breaking down the paper product. Paper products or waste include, but are not limited to, paper, pigmented papers, loaded papers, coated papers, corrugated paper, filled papers, magazines, printed matter, printer paper, polycoated paper, cardstock, cardboard, paperboard, or paper pulp, or a combination thereof. A forestry product or waste comprises material that is produced by cultivating, harvesting, or processing of wood, or any intermediate, byproduct, or waste that is generated from the cultivation, harvest, or processing of the wood. Forestry products or waste include, but are not limited to, aspen wood, wood from any genus or species of tree, particle board, wood chips, or sawdust, or a combination thereof. A general waste includes, but is not limited to, manure, sewage, or offal, or a combination thereof.

In an embodiment, the biomass comprises agriculture waste, such as corn cobs, e.g., corn stover. In another embodiment, the biomass comprises grasses.

In one embodiment, the biomass is treated prior to contact with the compositions described herein. For example, the biomass is treated to reduce the recalcitrance of the biomass, to reduce its bulk density, and/or increase its surface area. Suitable biomass treatment process may include, but are not limited to: bombardment with electrons, sonication, oxidation, pyrolysis, steam explosion, chemical treatment, mechanical treatment, and freeze grinding. Preferably, the treatment method is bombardment with electrons.

In some embodiments, electron bombardment is performed until the biomass receives a total dose of at least 0.5 Mrad, e.g. at least 5, 10, 20, 30, or at least 40 Mrad. In some embodiments, the treatment is performed until the biomass receives a dose a of from about 0.5 Mrad to about 150 Mrad, about 1 Mrad to about 100 Mrad, about 5 Mrad to about 75 Mrad, about 2 Mrad to about 75 Mrad, about 10 Mrad to about 50 Mrad, e.g., about 5 Mrad to about 50 Mrad, about 20 Mrad to about 40 Mrad, about 10 Mrad to about 35 Mrad, or from about 20 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 9 Mrad/pass can in some cases cause thermal degradation of the feedstock material.

The biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the biomass to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The biomass can be hydrolyzed using an enzyme, e.g., a biomass degrading enzyme, by combining the materials and the enzyme in a solvent, e.g., in an aqueous solution. The enzymes can be made/induced according to the methods described herein.

Specifically, the biomass degrading enzyme can be supplied by organisms, e.g., a microorganism, that are capable of breaking down biomass (such as the cellulose and/or the lignin portions of the biomass), or that contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Saccharification

The reduced-recalcitrance biomass is treated with the biomass-degrading enzymes discussed above, generally by combining the reduced-recalcitrance biomass and the biomass-degrading enzymes in a fluid medium, e.g., an aqueous solution. In some cases, the feedstock is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

Provided herein are mixtures of enzymes that are capable of degrading the biomass, e.g., an enzyme mixture of biomass-degrading enzymes, for use in the saccharification process described herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

In a preferred embodiment, the saccharification reaction occurs at a pH optimal for the enzymatic reactions to occur, e.g., at the pH optimal for the activity of the biomass-degrading enzymes. Preferably, the pH of the saccharification reaction is at pH 4-4.5. In a preferred embodiment, the saccharification reaction occurs at a temperature optimal for the enzymatic reactions to occur, e.g., at the temperature optimal for the activity of the biomass-degrading enzymes. Preferably, the temperature of the saccharification reaction is at 42° C.-52° C.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In the processes described herein, for example after saccharification, sugars e.g., glucose and xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Enzyme Mixtures for Saccharification

The present invention provides an enzyme mixture comprising a glycosylated polypeptide comprising at least 50%, 55%, 60%, 65%, 70%, 75%, 80%, 85%, 90%, 91%, 92%, 93%, 94%, 95%, 96%, 97%, 98%, or 99% identity to SEQ ID NO: 1, and an aglycosylated polypeptide comprising at least 50%, 55%, 60%, 65%, 70%, 75%, 80%, 85%, 90%, 91%, 92%, 93%, 94%, 95%, 96%, 97%, 98%, or 99% identity to SEQ ID NO: 1, wherein both the glycosylated polypeptide and the aglyscosylated polypeptide have cellobiase activity. The aglycosylated polypeptide having cellobiase activity is any of the aglycosylated polypeptides described herein, e.g., produced using the methods described herein. The glycosylated polypeptide comprising at least 50%, 55%, 60%, 65%, 70%, 75%, 80%, 85%, 90%, 91%, 92%, 93%, 94%, 95%, 96%, 97%, 98%, or 99% identity to SEQ ID NO: 1 can be isolated or obtained from a microorganism that endogenously expresses the polypeptide.

In an embodiment, the glysocylated polypeptide and the aglycosylated polypeptide are both the Cel3A enzyme from wild-type T. reesei, e.g., comprising SEQ ID NO: 1.

In embodiments, the enzyme mixture further comprises at least one additional enzyme derived from a microorganism, wherein the additional enzyme has biomass or cellulose-based material-degrading activity, e.g., the additional enzyme is a cellulolytic enzyme, e.g., a cellulase. For example, the additional enzyme is a ligninase, an endoglucanase, a cellobiohydrolase, a xylanase, and a cellobiase. In an embodiment, the mixture further comprises one or more ligninase, one or more endogluconase, one or more cellobiohydrolase, and one or more xylanase. In embodiments, the additional biomass-degrading enzyme is glycosylated. In embodiments, the enzyme mixture further comprises at least 2, at least 3, at least 4, at least 5, at least 6, at least 7, at least 8, at least 9, or at least 10 additional biomass-degrading enzymes described herein. For example, the enzyme mixture further comprises at least 1, at least 2, at least 3, at least 4, at least 5, at least 6, at least 7, at least 8, at least 9, at least 10, at least 11, at least 12, at least 13, at least 14, at least 15 or all of the enzymes listed in Table 1.

For example, the enzyme mixture further comprises a mixture of additional biomass-degrading enzymes produced by a microorganism, e.g., a fungal cell, such as wild-type *T. reesei*, or a mutant thereof, e.g., *T. Reesei* RUTC30. In an embodiment, the additional biomass-degrading enzymes are isolated from the microorganisms. In an embodiment, the mixture comprises one or more of the following biomass-degrading enzymes: B2AF03, CIP1, CIP2, Cel1a, Cel3a, Cel5a, Cel6a, Cel1a, Cel7b, Cel12a, Cel45a, Cel74a, paMan5a, paMan26a, or Swollenin, or any combination thereof. The additional biomass-degrading enzymes, e.g., listed above, can be endogenously expressed and isolated from the microorganism, e.g., fungal cell, from which the enzyme originates from (listed below in Table 1). Alternatively, the additional biomass-degrading enzymes, e.g., listed above, can be heterologously expressed using similar methods of expression in a host cell described herein, and isolated from the host cells. In an embodiment, the heterologously expressed additional biomass-degrading enzymes are tagged with a His tag at the C or N terminus of the enzyme and are isolated using nickel affinity chromatography techniques known in the art. For example, the additional biomass-degrading enzymes can be selected from Table 1 below.

TABLE 1

Examples of Additional Biomass-Degrading Enzymes

| Protein | MW, kDa | no AA's | th. pI | no. Cysteines | Organism |
|---|---|---|---|---|---|
| B2AF03-C'His | 88.6 | 813 | 6.3 | 10 | *Podospora anserina* |
| CIP1-C'His | 32.5 | 311 | 5.6 | 8 | *Trichoderma reesei* |
| CIP2-C'His | 48.0 | 457 | 7.0 | 12 | *Trichoderma reesei* |
| Cel1a-C'His | 53.6 | 478 | 5.8 | 5 | *Trichoderma reesei* |
| Cel3a-C'His | 78.0 | 739 | 6.3 | 6 | *Trichoderma reesei* |
| Cel3a-N'His | 78.0 | 739 | 6.3 | 6 | *Trichoderma reesei* |
| Cel5a-N'His | 43.7 | 411 | 5.7 | 12 | *Trichoderma reesei* |
| Cel6a-C'His | 48.8 | 461 | 6.0 | 12 | *Trichoderma reesei* |
| Cel7a-C'His | 53.8 | 511 | 4.8 | 24 | *Trichoderma reesei* |
| Cel7b-C'His | 47.6 | 451 | 5.3 | 22 | *Trichoderma reesei* |
| Cel12a-C'His | 25.1 | 232 | 6.9 | 2 | *Trichoderma reesei* |
| Cel45a-C'His | 24.4 | 239 | 5.4 | 16 | *Trichoderma reesei* |
| Cel74a-C'His | 86.7 | 832 | 5.7 | 4 | *Trichoderma reesei* |
| paMan5a-C'His | 41.0 | 370 | 7.0 | 6 | *Podospora anserina* |
| paMan26a-C'His | 51.4 | 463 | 5.2 | 1 | *Podospora anserina* |
| Swollenin-N'His | 51.5 | 491 | 5.3 | 28 | *Trichoderma reesei* |

The amino acid sequences for the biomass-degrading enzymes listed in Table 1 are provided below.

B2AF03 (*Podospora anserina*)
(SEQ ID NO: 9)

MKSSVFWGASLTSAVVRAIDLPFQFYPNCVDDLLSTNQVCNTTLSPPERAAALVAALTPEE

KLQNIVSKSLGAPRIGLPAYNWWSEALHGVAYAPGTQFWQGDGPFNSSTSFPMPLLMAATFDDELLEKI

AEVIGIEGRAFGNAGFSGLDYWTPNVNPFKDPRWGRGSETPGEDVLLVKRYAAAMIKGLEGPVPEKERR

VVATCKHYAANDFEDWNGATRHNFNAKISLQDMAEYYFMPFQQCVRDSRVGSIMCAYNAVNGVPSCASP

YLLQTILREHWNWTEHNNYITSDCEAVLDVSLNHKYAATNAEGTAISFEAGMDTSCEYEGSSDIPGAWS

QGLLKESTVDRALLRLYEGIVRAGYFDGKQSLYSSLGWADVNKPSAQKLSLQAAVDGTVLLKNDGTLPL

SDLLDKSRPKKVAMIGFWSDAKDKLRGGYSGTAAYLHTPAYAASQLGIPFSTASGPILHSDLASNQSWT

DNAMAAAKDADYILYFGGIDTSAAGETKDRYDLDWPGAQLSLINLLTTLSKPLIVLQMGDQLDNTPLLS

NPKINAILWANWPGQDGGTAVMELVTGLKSPAGRLPVTQYPSNFTELVPMTDMALRPSAGNSQLGRTYR

WYKTPVQAFGFGLHYTTFSPKFGKKFPAVIDVDEVLEGCDDKYLDTCPLPDLPVVVENRGNRTSDYVAL

AFVSAPGVGPGPWPIKTLGAFTRLRGVKGGEKREGGLKWNLGNLARHDEEGNTVVYPGKYEVSLDEPPK

ARLRFEIVRGGKGKGKVKGKGKAAQKGGVVLDRWPKPPKGQEPPAIERV

CIP1 (*Trichoderma reesei*)
(SEQ ID NO: 10)

MVRRTALLALGALSTLSMAQISDDFESGWDQTKWPISAPDCNQGGTVSLDTTVAHSGSNSM

KVVGGPNGYCGHIFFGTTQVPTGDVYVRAWIRLQTALGSNHVTFIIMPDTAQGGKHLRIGGQSQVLDYN

RESDDATLPDLSPNGIASTVTLPTGAFQCFEYHLGTDGTIETWLNGSLIPGMTVGPGVDNPNDAGWTRA

SYIPEITGVNFGWEAYSGDVNTVWFDDISIASTRVGCGPGSPGGPGSSTTGRSSTSGPTSTSRPSTTIP

PPTSRTTTATGPTQTHYGQCGGIGYSGPTVCASGTTCQVLNPYYSQCL

CIP2 (*Trichoderma reesei*)
(SEQ ID NO: 11)

MASRFFALLLLAIPIQAQSPVWGQCGGIGWSGPTTCVGGATCVSYNPYYSQCIPSTQASSS

IASTTLVTSFTTTTATRTSASTPPASSTGAGGATCSALPGSITLRSNAKLNDLFTMFNGDKVTTKDKFS

CRQAEMSELIQRYELGTLPGRPSTLTASFSGNTLTINCGEAGKSISFTVTITYPSSGTAPYPAIIGYGG

GSLPAPAGVAMINFNNDNIAAQVNTGSRGQGKFYDLYGSSHSAGAMTAWAWGVSRVIDALELVPGARID

-continued

TTKIGVTGCSRNGKGAMVAGAFEKRIVLTLPQESGAGGSACWRISDYLKSQGANIQTASEIIGEDPWFS

TTFNSYVNQVPVLPFDHHSLAALIAPRGLFVIDNNIDWLGPQSCFGCMTAAHMAWQALGVSDHMGYSQI

GAHAHCAFPSNQQSQLTAFVQKFLLGQSTNTAIFQSDFSANQSQWIDWTTPTLS

Cel1a (*Trichoderma reesei*)
(SEQ ID NO: 12)
MLPKDFQWGFATAAYQIEGAVDQDGRGPSIWDTFCAQPGKIADGSSGVTACDSYNRTAEDI

ALLKSLGAKSYRFSISWSRIIPEGGRGDAVNQAGIDHYVKFVDDLLDAGITPFITLFHWDLPEGLHQRY

GGLLNRTEFPLDFENYARVMFRALPKVRNWITFNEPLCSAIPGYGSGTFAPGRQSTSEPWTVGHNILVA

HGRAVKAYRDDFKPASGDGQIGIVLNGDFTYPWDAADPADKEAAERRLEFFTAWFADPIYLGDYPASMR

KQLGDRLPTFTPEERALVHGSNDFYGMNHYTSNYIRHRSSPASADDTVGNVDVLFTNKQGNCIGPETQS

PWLRPCAAGFRDFLVWISKRYGYPPIYVTENGTSIKGESDLPKEKILEDDFRVKYYNEYIRAMVTAVEL

DGVNVKGYFAWSLMDNFEWADGYVTRFGVTYVDYENGQKRFPKKSAKSLKPLFDELIAAA

Cel3a (*Trichoderma reesei*)
(SEQ ID NO: 13)
MRYRTAAALALATGPFARADSHSTSGASAEAVVPPAGTPWGTAYDKAKAALAKLNLQDKVG

IVSGVGWNGGPCVGNTSPASKISYPSLCLQDGPLGVRYSTGSTAFTPGVQAASTWDVNLIRERGQFIGE

EVKASGIHVILGPVAGPLGKTPQGGRNWEGFGVDPYLTGIAMGQTINGIQSVGVQATAKHYILNEQELN

RETISSNPDDRTLHELYTWPFADAVQANVASVMCSYNKVNTTWACEDQYTLQTVLKDQLGFPGYVMTDW

NAQHTTVQSANSGLDMSMPGTDFNGNNRLWGPALTNAVNSNQVPTSRVDDMVTRILAAWYLTGQDQAGY

PSFNISRNVQGNHKTNVRAIARDGIVLLKNDANILPLKKPASIAVVGSAAIIGNHARNSPSCNDKGCDD

GALGMGWGSGAVNYPYFVAPYDAINTRASSQGTQVTLSNTDNTSSGASAARGKDVAIVFITADSGEGYI

TVEGNAGDRNNLDPWHNGNALVQAVAGANSNVIVVVHSVGAIILEQILALPQVKAVVWAGLPSQESGNA

LVDVLWGDVSPSGKLVYTIAKSPNDYNTRIVSGGSDSFSEGLFIDYKHFDDANITPRYEFGYGLSYTKF

NYSRLSVLSTAKSGPATGAVVPGGPSDLFQNVATVTVDIANSGQVTGAEVAQLYITYPSSAPRTPPKQL

RGFAKLNLTPGQSGTATFNIRRRDLSYWDTASQKWVVPSGSFGISVGASSRDIRLTSTLSVA

Cel5a (*Trichoderma reesei*)
(SEQ ID NO: 14)
MNKSVAPLLLAASILYGGAAAQQTVWGQCGGIGWSGPTNCAPGSACSTLNPYYAQCIPGAT

TITTSTRPPSGPTTTTRATSTSSSTPPTSSGVRFAGVNIAGFDFGCTTDGTCVTSKVYPPLKNFTGSNN

YPDGIGQMQHFVNDDGMTIFRLPVGWQYLVNNNLGGNLDSTSISKYDQLVQGCLSLGAYCIVDIHNYAR

WNGGIIGQGGPTNAQFTSLWSQLASKYASQSRVWFGIMNEPHDVNINTWAATVQEVVTAIRNAGATSQF

ISLPGNDWQSAGAFISDGSAAALSQVTNPDGSTTNLIFDVHKYLDSDNSGTHAECTTNNIDGAFSPLAT

WLRQNNRQAILTETGGGNVQSCIQDMCQQIQYLNQNSDVYLGYVGWGAGSFDSTYVLTETPTGSGNSWT

DTSLVSSCLARK

Cel6a (*Trichoderma reesei*)
(SEQ ID NO: 15)
MIVGILTTLATLATLAASVPLEERQACSSVWGQCGGQNWSGPTCCASGSTCVYSNDYYSQC

LPGAASSSSTRAASTTSRVSPTTSRSSSATPPPGSTTTRVPPVGSGTATYSGNPFVGVTPWANAYYAS

EVSSLAIPSLTGAMATAAAAVAKVPSFMWLDTLDKTPLMEQTLADIRTANKNGGNYAGQFVVYDLPDRD

CAALASNGEYSIADGGVAKYKNYIDTIRQIVVEYSDIRTLLVIEPDSLANLVTNLGTPKCANAQSAYLE

CINYAVTQLNLPNVAMYLDAGHAGWLGWPANQDPAAQLFANVYKNASSPRALRGLATNVANYNGWNITS

PPSYTQGNAVYNEKLYIHAIGPLLANHGWSNAFFITDQGRSGKQPTGQQQWGDWCNVIGTGFGIRPSAN

TGDSLLDSFVWVKPGGECDGTSDSSAPRFDSHCALPDALQPAPQAGAWFQAYFVQLLTNANPSFL

-continued

Cel7a (*Trichoderma reesei*)
(SEQ ID NO: 16)
MYRKLAVISAFLATARAQSACTLQSETHPPLTWQKCSSGGTCTQQTGSVVIDANWRWTHAT

NSSTNCYDGNTWSSTLCPDNETCAKNCCLDGAAYASTYGVTTSGNSLSIGFVTQSAQKNVGARLYLMAS

DTTYQEFTLLGNEFSFDVDVSQLPCGLNGALYFVSMDADGGVSKYPTNTAGAKYGTGYCDSQCPRDLKF

INGQANVEGWEPSSNNANTGIGGHGSCCSEMDIWEANSISEALTPHPCTTVGQEICEGDGCGGTYSDNR

YGGTCDPDGCDWNPYRLGNTSFYGPGSSFTLDTTKKLTVVTQFETSGAINRYYVQNGVTFQQPNAELGS

YSGNELNDDYCTAEEAEFGGSSFSDKGGLTQFKKATSGGMVLVMSLWDDYYANMLWLDSTYPTNETSST

PGAVRGSCSTSSGVPAQVESQSPNAKVTFSNIKFGPIGSTGNPSGGNPPGGNPPGTTTTRRPATTTGSS

PGPTQSHYGQCGGIGYSGPTVCASGTTCQVLNPYYSQCL

Cel7b (*Trichoderma reesei*)
(SEQ ID NO: 17)
MAPSVTLPLTTAILAIARLVAAQQPGTSTPEVHPKLTTYKCTKSGGCVAQDTSVVLDWNYR

WMHDANYNSCTVNGGVNTTLCPDEATCGKNCFIEGVDYAASGVTTSGSSLTMNQYMPSSSGGYSSVSPR

LYLLDSDGEYVMLKLNGQELSFDVDLSALPCGENGSLYLSQMDENGGANQYNTAGANYGSGYCDAQCPV

QTWRNGTLNTSHQGFCCNEMDILEGNSRANALTPHSCTATACDSAGCGFNPYGSGYKSYYGPGDTVDTS

KTFTIITQFNTDNGSPSGNLVSITRKYQQNGVDIPSAQPGGDTISSCPSASAYGGLATMGKALSSGMVL

VFSIWNDNSQYMNWLDSGNAGPCSSTEGNPSNILANNPNTHVVFSNIRWGDIGSTTNSTAPPPPPASST

TFSTTRRSSTTSSSPSCTQTHWGQCGGIGYSGCKTCTSGTTCQYSNDYYSQCL

Cel12a (*Trichoderma reesei*)
(SEQ ID NO: 18)
MKFLQVLPALIPAALAQTSCDQWATFTGNGYTVSNNLWGASAGSGFGCVTAVSLSGGASWH

ADWQWSGGQNNVKSYQNSQIAIPQKRTVNSISSMPTTASWSYSGSNIRANVAYDLFTAANPNHVTYSGD

YELMIWLGKYGDIGPIGSSQGTVNVGGQSWTLYYGYNGAMQVYSFVAQTNTTNYSGDVKNFFNYLRDNK

GYNAAGQYVLSYQFGTEPFTGSGTLNVASWTASIN

Cel45a (*Trichoderma reesei*)
(SEQ ID NO: 19)
MKATLVLGSLIVGAVSAYKATTTRYYDGQEGACGCGSSSGAFPWQLGIGNGVYTAAGSQAL

FDTAGASWCGAGCGKCYQLTSTGQAPCSSCGTGGAAGQSIIVMVTNLCPNNGNAQWCPVVGGTNQYGYS

YHFDIMAQNEIFGDNVVVDFEPIACPGQAASDWGTCLCVGQQETDPTPVLGNDTGSTPPGSSPPATSSS

PPSGGGQQTLYGQCGGAGWTGPTTCQAPGTCKVQNQWYSQCLP

Cel74a (*Trichoderma reesei*)
(SEQ ID NO: 20)
MKVSRVLALVLGAVIPAHAAFSWKNVKLGGGGGFVPGIIFHPKTKGVAYARTDIGGLYRLN

ADDSWTAVTDGIADNAGWHNWGIDAVALDPQDDQKVYAAVGMYTNSWDPSNGAIIRSSDRGATWSFTNL

PFKVGGNMPGRGAGERLAVDPANSNIIYFGARSGNGLWKSTDGGVTFSKVSSFTATGTYIPDPSDSNGY

NSDKQGLMWVTFDSTSSTTGGATSRIFVGTADNITASVYVSTNAGSTWSAVPGQPGKYFPHKAKLQPAE

KALYLTYSDGTGPYDGTLGSVWRYDIAGGTWKDITPVSGSDLYFGFGGLGLDLQKPGTLVVASLNSWWP

DAQLFRSTDSGTTWSPIWAWASYPTETYYYSISTPKAPWIKNNFIDVTSESPSDGLIKRLGWMIESLEI

DPTDSNHWLYGTGMTIFGGHDLTNWDTRHNVSIQSLADGIEEFSVQDLASAPGGSELLAAVGDDNGFTF

ASRNDLGTSPQTVWATPTWATSTSVDYAGNSVKSVVRVGNTAGTQQVAISSDGGATWSIDYAADTSMNG

GTVAYSADGDTILWSTASSGVQRSQFQGSFASVSSLPAGAVIASDKKTNSVFYAGSGSTFYVSKDTGSS

FTRGPKLGSAGTIRDIAAHPTTAGTLYVSTDVGIFRSTDSGTTFGQVSTALTNTYQIALGVGSGSNWNL

-continued

YAFGTGPSGARLYASGDSGASWTDIQGSQGFGSIDSTKVAGSGSTAGQVYVGTNGRGVFYAQGTVGGGT

GGTSSSTKQSSSSTSSASSSTTLRSSVVSTTRASTVTSSRTSSAAGPTGSGVAGHYAQCGGIGWTGPTQ

CVAPYVCQKQNDYYYQCV paMan5a (Podospora anserina)
(SEQ ID NO: 21)
MKGLFAFGLGLLSLVNALPQAQGGGAAASAKVSGTRFVIDGKTGYFAGTNSYWIGFLTNNR

DVDTTLDHIASSGLKILRVWGFNDVNNQPSGNTVWFQRLASSGSQINTGPNGLQRLDYLVRSAETRGIK

LIIALVNYWDDFGGMKAYVNAFGGTKESWYTNARAQEQYKRYIQAVVSRYVNSPAIFAWELANEPRCKG

CNTNVIFNWATQISDYIRSLDKDHLITLGDEGFGLPGQTTYPYQYGEGTDFVKNLQIKNLDFGTFHMYP

GHWGVPTSFGPGWIKDHAAACRAAGKPCLLEEYGYESDRCNVQKGWQQASRELSRDGMSGDLFWQWGDQ

LSTGQTHNDGFTIYYGSSLATCLVTDHVRAINALPA paMan26a (Podospora anserina)
(SEQ ID NO: 22)
MVKLLDIGLFALALASSAVAKPCKPRDGPVTYEAEDAILTGTTVDTAQVGYTGRGYVTGFD

EGSDKITFQISSATTKLYDLSIRYAAIYGDKRTNVVLNNGAVSEVFFPAGDSFTSVAAGQVLLNAGQNT

IDIVNNWGWYLIDSITLTPSAPRPPHDINPNLNNPNADTNAKKLYSYLRSVYGNKIISGQQELHHAEWI

RQQTGKTPALVAVDLMDYSPSRVERGTTSHAVEDAIAHHNAGGIVSVLWHWNAPVGLYDTEENKWWSGF

YTRATDFDIAATLANPQGANYTLLIRDIDAIAVQLKRLEAAGVPVLWRPLHEAEGGWFWWGAKGPEPAK

QLWDILYERLTVHHGLDNLIWVWNSILEDWYPGDDTVDILSADVYAQGNGPMSTQYNELIALGRDKKMI

AAAEVGAAPLPGLLQAYQANWLWFAVWGDDFINNPSWNTVAVLNEIYNSDYVLTLDEIQGWRS

Swollenin (Trichoderma reesei)
(SEQ ID NO: 23)
MAGKLILVALASLVSLSIQQNCAALFGQCGGIGWSGTTCCVAGAQCSFVNDWYSQCLASTGGNPPNGTT

SSSLVSRTSSASSSVGSSSPGGNSPTGSASTYTTTDTATVAPHSQSPYPSIAASSCGSWTLVDNVCCPS

YCANDDTSESCSGCGTCTTPPSADCKSGTMYPEVHHVSSNESWHYSRSTHFGLTSGGACGFGLYGLCTK

GSVTASWTDPMLGATCDAFCTAYPLLCKDPTGTTLRGNFAAPNGDYYTQFWSSLPGALDNYLSCGECIE

LIQTKPDGTDYAVGEAGYTDPITLEIVDSCPCSANSKWCCGPGADHCGEIDFKYGCPLPADSIHLDLSD

IAMGRLQGNGSLTNGVIPTRYRRVQCPKVGNAYIWLRNGGGPYYFALTAVNTNGPGSVTKIEIKGADTD

NWVALVHDPNYTSSRPQERYGSWVIPQGSGPFNLPVGIRLTSPTGEQIVNEQAIKTFTPPATGDPNFYY

IDIGVQFSQN

The ratio between the aglycosylated polypeptide described herein to the other biomass-degrading enzymes in the mixture can be, for example, at least 1:1; 1:2; 1:4; 1:8; 1:16; 1:32; 1:50; 1:75; 1:100, 1:150; 1:200; 1:300, 1:400 or 1:500. In an embodiment, the ratio of aglycosylated polypeptide described herein to the other enzymes in the mixture is 1:32. The ratio between the aglycosylated polypeptide described herein to the glycosylated polypeptide is, for example, at least 1:1; 1:2; 1:4; 1:8; 1:16; 1:32; 1:50; 1:75; 1:100, 1:150; 1:200; 1:300, 1:400, or 1:500.

Other examples of suitable biomass-degrading enzymes for use in the enzyme mixture of the present invention include the enzymes from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum,* and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Biomass-degrading enzymes may also be obtained from *Chrysosporium*, preferably a strain of *Chrysosporium lucknowense*. Additional strains that can be used include, but are not limited to, *Trichoderma* (particularly *T. viride, T. reesei,* and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

In embodiments, the microorganism is induced to produce the biomass-degrading enzymes described herein under conditions suitable for increasing production of biomass-degrading enzymes compared to an uninduced microorganism. For example, an induction biomass sample comprising biomass as described herein is incubated with the microorganism to increase production of the biomass-degrading enzymes. Further description of the induction process can be found in US 2014/0011258, the contents of which are hereby incorporated by reference in its entirety.

The biomass-degrading enzymes produced and/or secreted by the aforementioned microorganisms can be isolated and added to the enzyme mixture of the present invention. Alternatively, in one embodiment, the aforementioned microorganisms or host cells expressing the biomass-degrading enzymes described herein and above are not lysed before addition to the saccharification reaction.

In an embodiment, the enzyme mixture comprises the host cell expressing an aglycosylated polypeptide having cellobiase activity as described herein, and one or more additional biomass-degrading enzymes described herein. In an embodiment, the enzyme mixture comprises a host cell expressing an aglycosylated polypeptide having cellobiase activity as described herein, and one or more host cells expressing one or more additional biomass-degrading enzymes described herein. For example, Use of the enzyme mixture described herein comprising an aglycosylated polypeptide having cellobiase activity results in increased yield of sugar products from saccharification compared to the yield of sugar products from saccharification using the standard mixture of biomass-degrading enzymes (e.g., RUTC30 cocktail, e.g., without addition of an aglycosylated polypeptide having cellobiase activity). The yield of sugar products increases at least 5%, at least 10%, at least 15%, at least 20%, at least 25%, at least 30%, at least 35%, at least 40%, at least 45%, at least 50%, at least 60%, at least 70%, at least 80%, at least 90%, at least 100% when an aglycosylated polypeptide having cellobiase activity is added to the saccharification process.

Further Processing

Further processing steps may be performed on the sugars produced by saccharification to produce alternative products. For example, the sugars can be hydrogenated, fermented, or treated with other chemicals to produce other products.

Glucose can be hydrogenated to sorbitol. Xylose can be hydrogenated to xylitol. Hydrogenation can be accomplished by use of a catalyst (e.g., Pt/gamma-$Al_2O_3$, Ru/C, Raney Nickel, or other catalysts know in the art) in combination with $H_2$ under high pressure (e.g., 10 to 12000 psi). The sorbitol and/or xylitol products can be isolated and purified using methods known in the art.

Sugar products from saccharification can also be fermented to produce alcohols, sugar alcohols, such as erythritol, or organic acids, e.g., lactic, glutamic or citric acids or amino acids.

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic conditions can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

"Fermentation" includes the methods and products that are disclosed in U.S. Prov. App. No. 61/579,559, filed Dec. 22, 2012, and U.S. Prov. App. No. 61/579,576, filed Dec. 22, 2012, the contents of both of which are incorporated by reference herein in their entirety.

Mobile fermenters can be utilized, as described in International App. No. PCT/US2007/074028 (which was filed Jul. 20, 2007, was published in English as WO 2008/011598 and designated the United States), the contents of which is incorporated herein in its entirety. Similarly, the saccharification equipment can be mobile. Further, saccharification and/or fermentation may be performed in part or entirely during transit.

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an algae. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. saccharobutylicum, C. Puniceum, C. beijernckii,* and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnolias, Ustilaginomycetes* sp., *Pseudozyma tsukubaensis,* yeast species of genera *Zygosaccharomyces, Debaryomyces, Hansenula* and *Pichia,* and fungi of the dematioid genus *Torula.*

For instance, *Clostridium* spp. can be used to produce ethanol, butanol, butyric acid, acetic acid, and acetone. *Lactobacillus* spp. can be used to produce lactic acid.

Many such microbial strains are publicly available, either commercially or through depositories such as the ATCC (American Type Culture Collection, Manassas, Va., USA), the NRRL (Agricultural Research Sevice Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALK) (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Many microorganisms that can be used to saccharify biomass material and produce sugars can also be used to ferment and convert those sugars to useful products.

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Other types of chemical transformation of the products from the processes described herein can be used, for example, production of organic sugar derived products such as (e.g., furfural and furfural-derived products). Chemical transformations of sugar derived products are described in U.S. Prov. App. No. 61/667,481, filed Jul. 3, 2012, the disclosure of which is incorporated herein by reference in its entirety.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Cloning of Cel3a-C'His into an Expression Vector

The mature sequence for Cel3a (amino acids 20-744) was synthesized and codon-optimized for *E. coli* expression by Genewiz. The Cel3a-C'His referred to in the following examples refers to the codon-optimized mature sequence for Cel3a (aas 20-744) with an 8×His (SEQ ID NO: 7) tag at the C-terminus. The below primers were used to clone the Cel3a-C'His into pET-Duet (Novagen, Catalog No. 71146):

```
Forward
                                         (SEQ ID NO: 4)
5'-CATGCCATGGGCGATAGTCACAGTACCAGC Reverse
                                         (SEQ ID NO: 5)
3'-CCCAAGCTTTCATTAGTGATGATGATGATGATGATGGCTGCCG

CTGCCGGCAACACTCAGGGTGC
```

(NcoI and HindIII sites are underlined; start and stop codons are in bold; the polyhistidine (8-His (SEQ ID NO: 7)) tag; and glycine-serine (GSGS) linker (SEQ ID NO: 8) are italicized.)

The Amplification reaction was performed using PfuUltra II Fusion HS Polymerase (Agilent, Catalog No. 600672).

The amplified DNA was cloned by restriction digestion using NcoI restriction enzyme (New England Biolabs, R3193) and HindIII restriction enzyme (New England Biolabs, R3104) under conditions suggested by the manufacturer. The digested amplified DNA was ligated into the NcoI-HindIII sites in the pETDuet vector using T4 DNA ligase (New England Biolabs, M0202), followed by transformation of *E. coli* cloning host Top10 One Shot (Invitrogen). Plasmid purification was carried out using Qiagen's plasmid purification kit.

Example 2: Expression and Purification of Cel3a-C'His

The Cel3A-C'His constructs were transformed into the *E. coli* expression host Origami B (DE3) (EMD Millipore, Catalog No. 70837) and streaked on plates containing LB medium and 100 µg/ml ampicillin (Fisher Scientific, Catalog No. BP1760), 15 µg/ml kanamysin (Fisher Scientific, Catalog No. BP906) and 12.5 µg/ml tetracycline (Fisher Scientified, Catalog No. BP912). Colonies carrying the recombinant DNA were picked from plates for the inoculation of 2 ml starter cultures, and grown overnight at 37° C., then subsequently used to inoculate 100 ml of LB media containing the appropriate antibiotics. Cultures were grown at 37° C. until OD600 reached 0.8.

To induce protein expression, 500 µM IPTG (Isopropyl-b-D-thiogalactopyranoside; Fisher Scientific, Catalog No. BP1755) was added. The expression culture was further grown for another 4 hours at 37° C. The cells were harvested by centrifugation at 4000 g at room temperature (RT) for 20 minutes using the Sorvall St16 rotor TX400; and the pellet was stored at −80° C.

For protein extraction, the cell pellet was thawed on ice and resuspended in 2 ml of native lysis buffer containing 50 mM Tris-HCl pH 7.5, 0.1% Triton X-100, 5 mM imidazole (Fisher Scientific, Catalog No. 03196), and 1 mg/ml lysozyme (Fisher Scientific, Catalog No. BP535), then incubated on ice for 20 minutes. To digest the DNA in the sample, 2 μl of lysonase (EMD Millipore, Catalog No. 71230) was added and incubated for another 10 minutes. The sample was then spun in a microcentrifuge at maximum speed for 10 minutes at 4° C. The clarified lysate was transferred to a fresh tube containing 100 μl of pre-equilibrated Profinity (Biorad) Ni-charged IMAC resin slurry (Biorad, Catalog No. 732-4614). The native binding buffer consisted of 50 mM Tris HCl pH 7.5, 150 mM NaCl, 0.1% Triton X-100, and 5 μM imidazole. The protein was batch-bound for 1 hour at RT, and then washed with native buffer containing 25 μM imidazole. The protein was eluted in 300 ml of native buffer containing 200 μM imidazole. Purified Cel3a protein from the expression and purification process described above is shown in FIG. 1.

Example 3: Expression of Cel3a-C'His in Bioreactors

In this example, the expression and purification of Cel3a is scaled up to 3 liter and 5 liter bioreactors. The skilled artisan could readily use the process described herein to scale the production further, for example, to 3 L and 7 L bioreactors.

For each bioreactor run, the pET Duet-1 Cel3a-C'His construct is transformed into *E. Coli* Origami B (DE3) host cell line, and streaked on plates containing LB medium and 100 μg/ml ampicillin (Fisher Scientific, Catalog No. BP1760), 15 μg/ml kanamysin (Fisher Scientific, Catalog No. BP906) and 12.5 μg/ml tetracycline (Fisher Scientific, Catalog No. BP912).

On Day 1, colonies carrying the recombinant DNA were picked from plates for the inoculation of 200 ml starter cultures, and grown overnight at 37° C. The bioreactors were prepared, e.g., 1.5 L of LB media was added to each 3 L reactor, and 4 L of LB media was added to each 5 L reactor, with the appropriate antibiotics. Each reactor has a pH probe, a dissolved oxygen (DO) probe, and a condenser.

On Day 2, the OD of the overnight inoculums was measured by a spectrophotometer at 600 nM. The spectrophotometer can be blanked by using LB media. The bioreactors were set to 37° C., 300 rpm, and 2.5 vvm. Once the bioreactors reach 37° C., the appropriate mls of overnight inoculums was added to each 1.5 L and to each 4 L culture for a target starting OD value of 0.05. The OD of the reactors were measured occasionally by sampling out of the top with ethanol and a sterile pipet. As the OD approaches 0.8, samples were taken more frequently.

When the OD of the reactors reached 0.7-0.8 (approximately 2-4 hours after inoculation), the temperature of the bioreactors was reduced to 20° C., and the cultures were induced with IPTG for Cel3a-C'His protein expression. 750 ml of IPTG was added to each 1.5 L reactor and 1.5 ml of IPTG was added to each 5 L reactor. The reactors were run overnight.

On Day 3, in the morning, the cells were harvested into clean 2 L centrifuge bottles and spun at 4200 rpm for 45 minutes. The supernatant was discarded, and the pellet was saved and the weight of the pellet was recorded. Using PBS buffer, the pellet was transferred to 50 mL conical centrifuge tubes. The 50 mL tubes were spun at 4500 rpm for 45 minutes in the Sorvall St-16 tabletop centrifuge. Supernatant was discarded and the pellet was frozen at −20° C. until ready for purification, or processed immediately for purification.

Example 4: Protein Extraction from Cells

Lysis Buffer with EDTA was prepared, containing the following: 50 mM Tris-HCl pH 7.5, 0.1% Triton X-100, 1% Glycerol, 5 mM imidazole, 1 mg/mL Lysozyme, and 1 mM EDTA in de-ionized water. The cell pellet was resuspended in 5 mL volume of Lysis Buffer with EDTA. 10 μl of Lysonase (DNAse) was added to the sample. Samples were then incubated for 1 hour at room temperature.

Then, samples were sonicated on ice for three 1 minute intervals (e.g., for 3 minutes total, Sorvall sonicator at setting 17).

At this point, 1000 μl aliquots were e reserved from each fraction of the extraction process to analyze the yield and activity of the Cel3a-C'His protein from the extraction and purification process. An aliquot was taken from sonicated sample (sample A) to represent the total protein isolated. The sample was then centrifuged at 13000 rpm for 5 minutes, and the supernatant was removed. An aliquot was taken from the supernatant (sample D), representing the soluble fraction. The remaining pellet was resuspended in 1000 μl of Lysis Buffer+EDTA, and then centrifuged at 13000 rpm for 5 minutes. The supernatant was removed, and an aliquot was taken from the supernatant (sample E), representing the soluble wash fraction. The remaining pellet was reserved (sample C), representing the insoluble fraction. All samples were stored in the refrigerator (e.g., 4° C.) until analysis.

A cellobiase activity assay was performed using the total protein aliquot (sample A), for example, as described in Example 6.

The samples A, C, D, and E were also analyzed by SDS-PAGE and western blotting. Samples were diluted to 2.00 OD to normalize. 17.5 μl of LDS sample buffer (375 μl LDS buffer and 150 μl of NuPAGE reducing agent were mixed to prepare 525 μl of LDS sample buffer) was added to 32.5 μl of each sample. Samples were boiled for 5 minutes and 20 μl of each sample was loaded into each gel well. A standard (molecular weight ladder) was also loaded into a gel well.

Example 5: Mass Spectrometry Analysis of Purified Cel3a-N'His

Cel3a with a His-tag at the N-terminus (Cel3a-N'His) was cloned, expressed in *E. coli*, and harvested using methods similar to those described above in Examples 1-4. Cel3a-N'His was cloned into pET-Duet1 vector. The expressed Cel3a-N'His was purified with an affinity column containing Profinity Ni-charge IMAC resin slurry and eluted using elution buffer containing 200 mM imidazole in the lysis buffer.

The purified Cel3a-N'His was dialyzed in buffer containing 50 mM Tris-HCl and 0.5M EDTA. The dialyzed protein was then submitted for liquid chromatography-mass spectrometry (LCMS) intact mass analysis.

Sample concentration was determined, e.g., by Bradford assay and by Nanodrop assay. Sample concentration was at about 4 mg/mL. A 10× and 100× dilution sample was prepared for LCMS, with 0.1% formic acid in de-ionized water to provide 0.4 mg/mL and 0.04 mg/mL samples.

Figure 2:
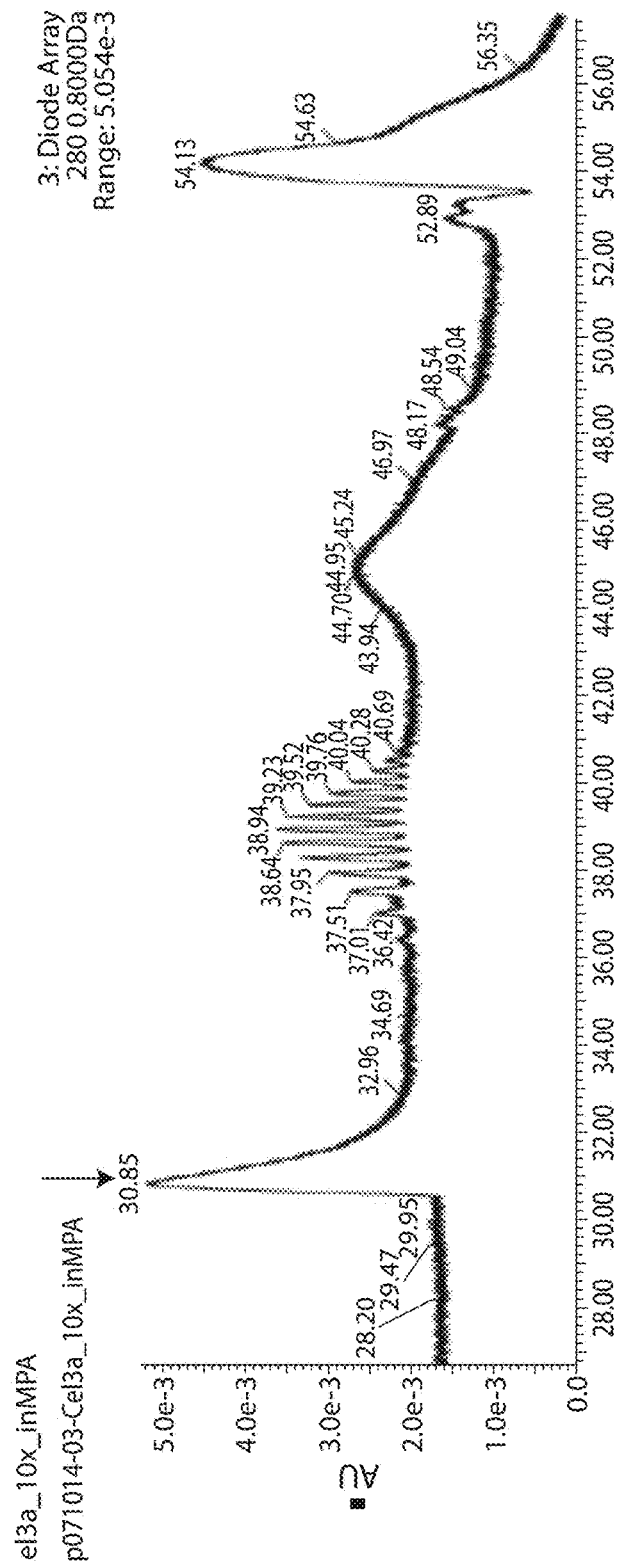
FIG. 2 is a chromatographic profile of the Cel3a-N'His sample, showing the detection of Cel3a-N'His at 31 minutes.
Figure 2:
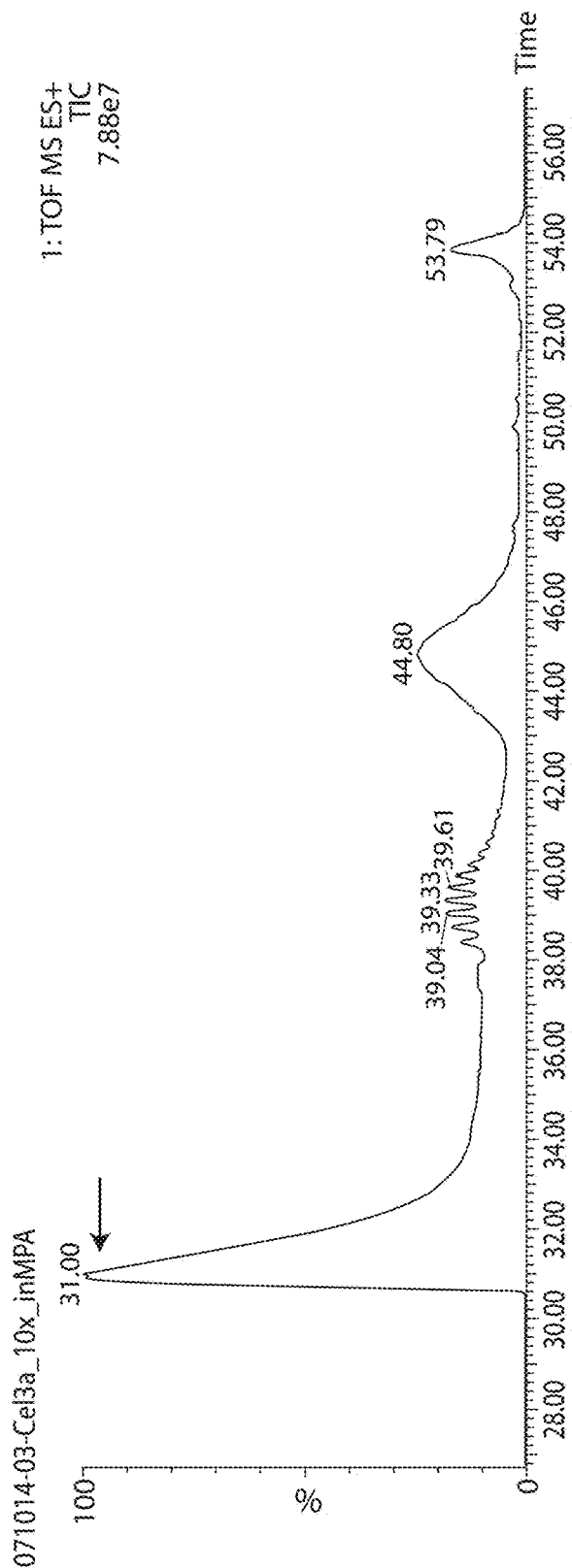

LC conditions were as follows:
Acquity UPLC H-Class Bio System: BEH300 C4 column, 1.7 μm, 2.1×150 mm (p/n: 186004497)
Column Temp: 45° C.
MPA: 0.1% FA in Water
MPB: 0.1% FA in ACN
Mass Spectrometer conditions were as follows:
Source Temp: 125° C.
Desolvation Temp: 450° C.
Cone Voltage: 40V
Calibration: CsI (500-5000 Da)
Lockmass: CsI The chromatographic profile of the sample is shown in FIG. 2. The profile shows three areas of interest: a large peak at 31 minutes, a cluster of peaks between 38 and 40 minutes, and a smaller peak at about 45 minutes. Manual deconvolution of the mass spectrum of peak at about 45 minutes and the peak cluster at about 39 minutes shows that the main peaks are not part of a charge state envelope, but rather a polymer series (with 44 amu as the repeating unit), and were thus attributed to possibly being from the Triton-X used in the lysis buffer.

Figure 3:
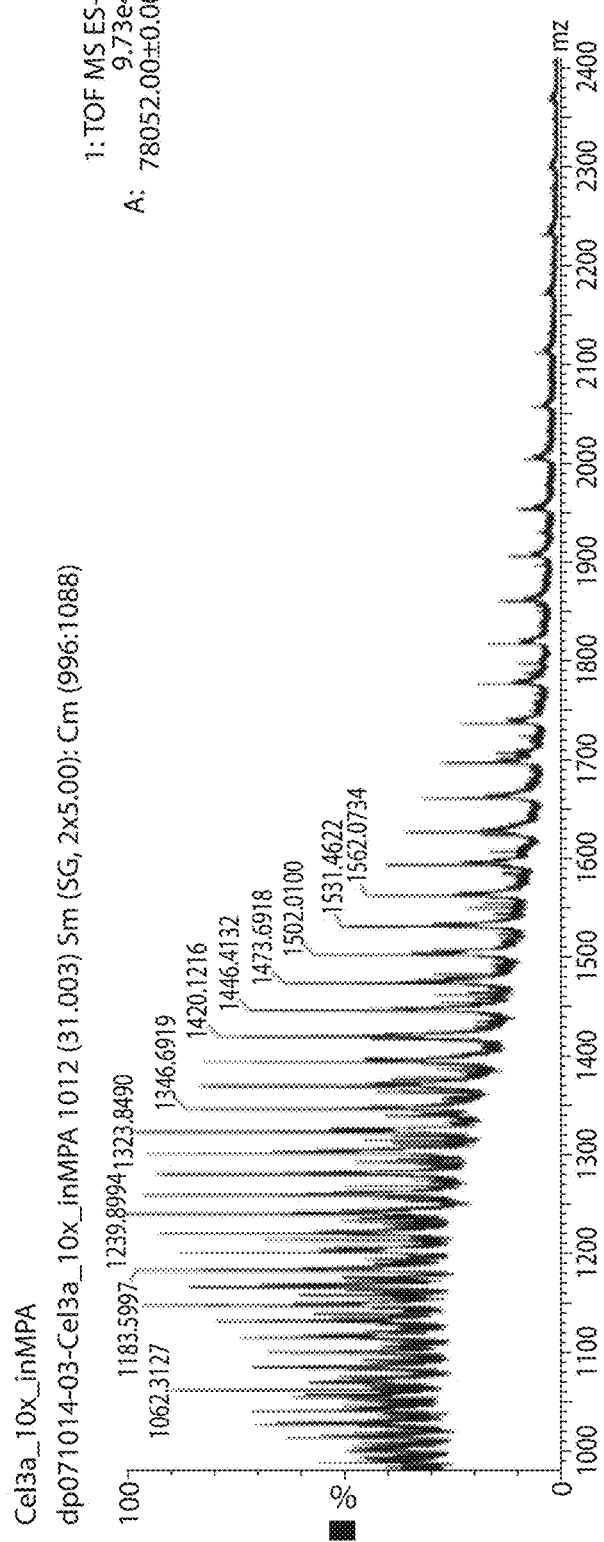
FIG. 3 is a profile showing no evidence of glycosylation in the mass spectral region for the peak in the chromatographic profile of the Cel3a-N'His at 31 minutes.
Figure 3:
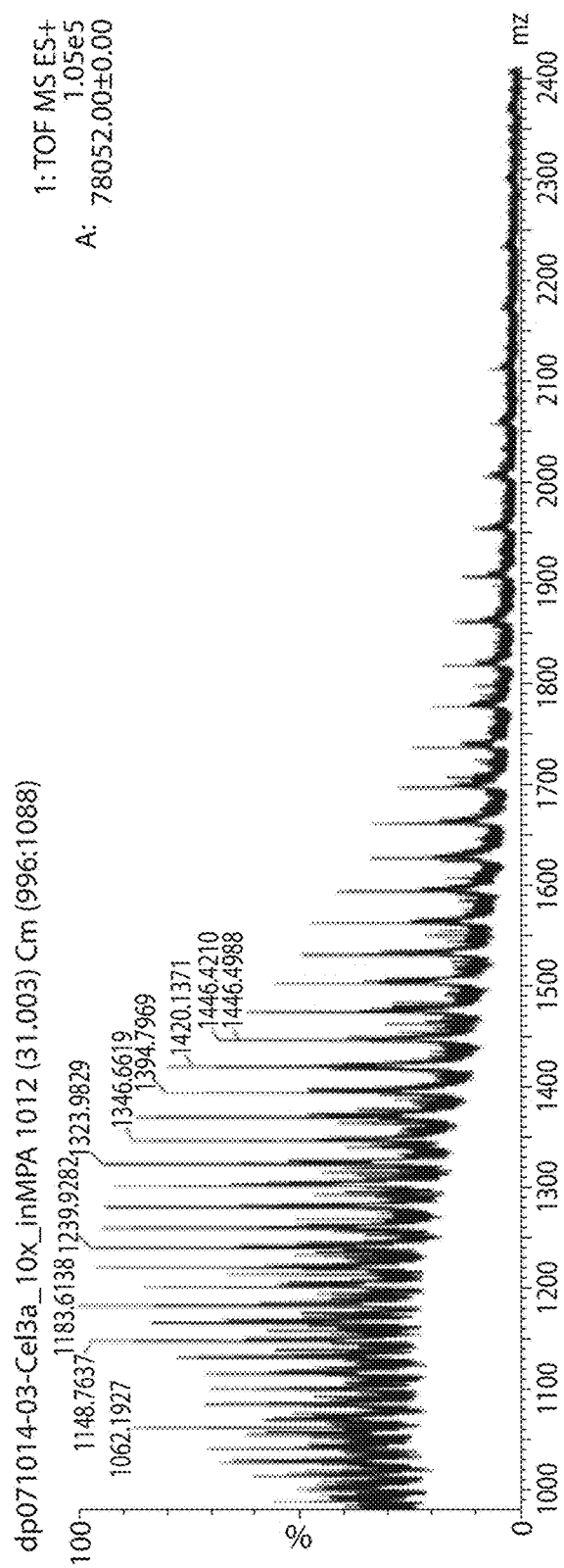
Figure 4:
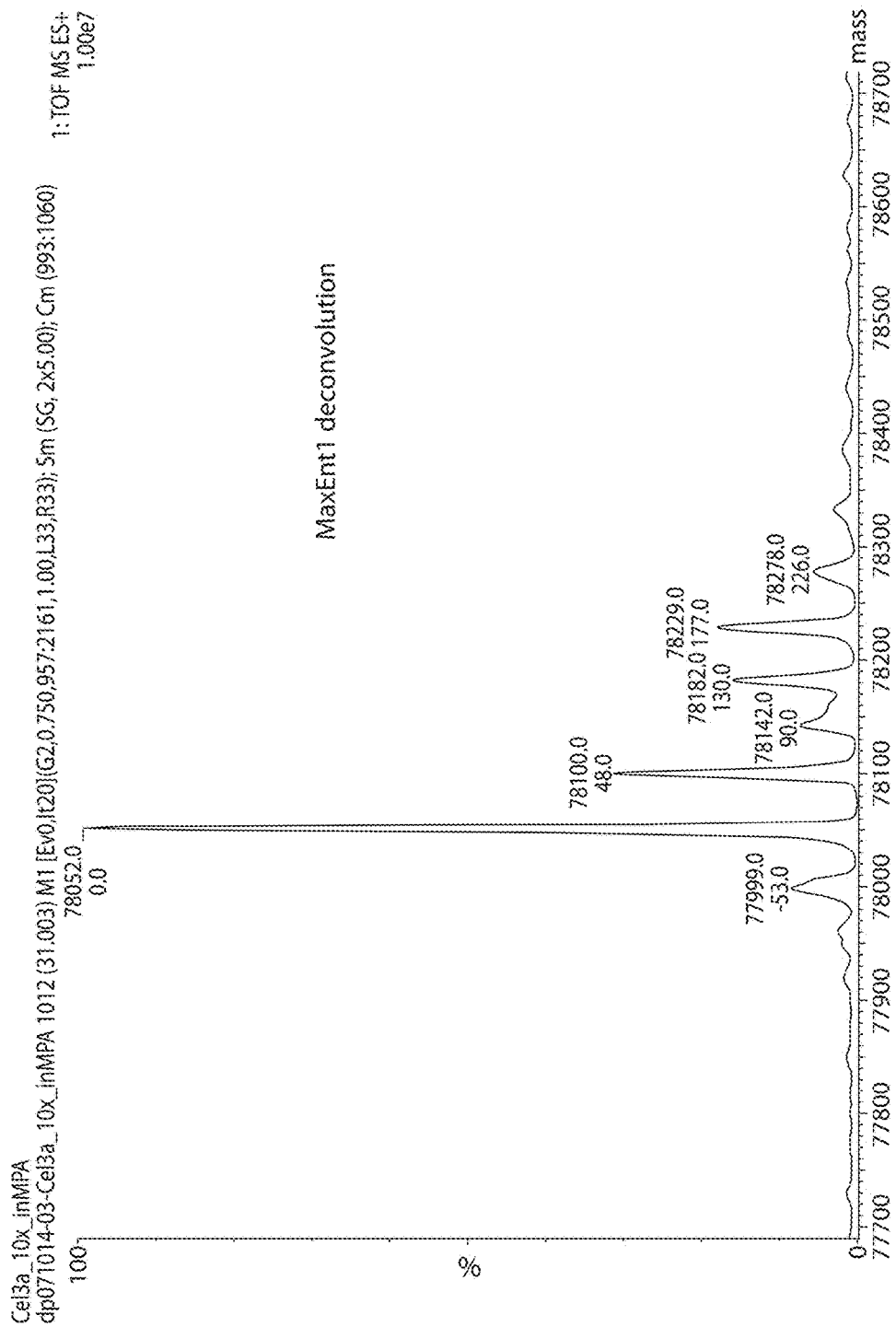
FIG. 4 is a profile showing the deconvolution of the charge state envelope, identifying the molecular weight of the major component (aglycosylated Cel3a-N'His) and the minor components (modified Cel3a-N'His).

Analysis of the mass spectral region for the peak detected at 31 minutes indicates a protein charge state envelope, and importantly, with no evidence of glycosylation (FIG. 3). Expansion of the charge state envelope indicates the presence of 2-3 minor proteins slightly larger than the major component. Deconvolution of the charge state envelope indicated that the major component had a molecular weight of 78,052 (FIG. 4), which corresponds to the expected molecular weight of Cel3a-N'His. The minor components had the following molecular weights: 78,100, 78,182, and 78,229 (FIG. 4), therefore indicating minor modifications to the Cel3a-N'His protein.

Among the charge states for the main component were several signals corresponding to smaller peptide fragments. These are distinguished by the more widely spaced isotope peaks. Some of the fragments identified have molecular weights of 8,491, 9,261, and 11,629. These fragments may be generated in the MS source, or may originate from the sample.

The results from this experiment demonstrate that an aglycosylated cellobiase, Cel3a-N'His was cloned, expressed, and isolated using the methods encompassed by the present invention.

Example 6: Cellobiase Activity Assay

His-tagged Cel3a (e.g., Cel3a with a His-tag at the N or C-terminus) were purified using IMAC techniques. The amount (titer) of purified His-tagged Cel3a was determined using Bradford assay and/or the nanodrop. For nanodrop quantification, the molar extinction coefficient was estimated by inserting the amino acid sequence of the target form of Cel3a into the ExPASy ProtParam online tool.

Figure 5:
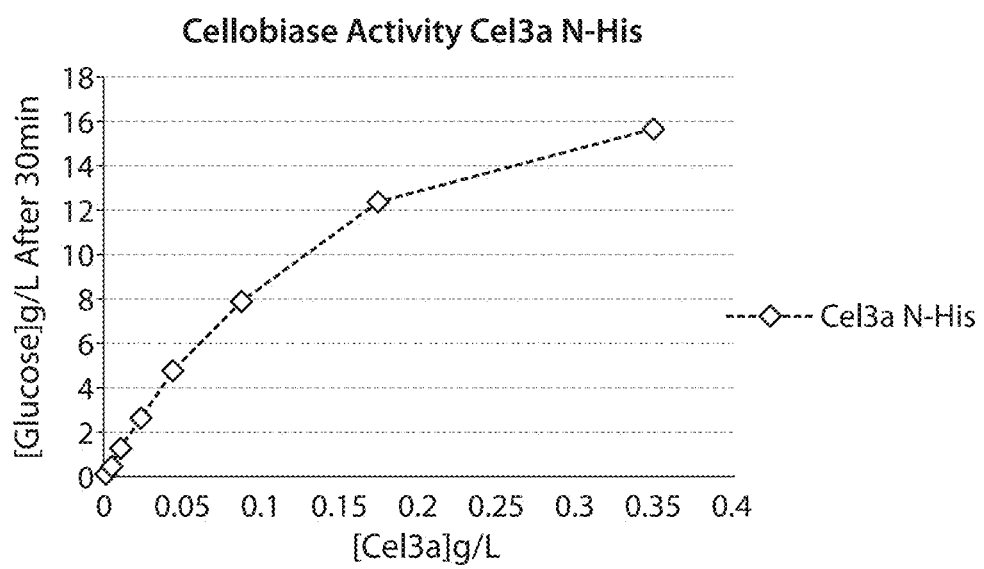
FIG. 5 is a graph showing the cellobiase activity, as determined by cellobiase assay, of a purified Cel3a-N'His.

For the activity assay, two fold serial dilutions of samples containing Cel3a-N'His were performed in a 96 well plate format. Dilutions were incubated with a D-(+)-Cellobiose (Fluka) substrate solution in 50 mM sodium citrate monobasic buffer at pH 5.0, at 48° C. for 30 minutes. After 30 minutes, the samples were heated to 100° C. for 10 minutes to stop the reaction. Samples were analysed for glucose and cellobiose using the YSI Biochemistry analyser (YSI Life Sciences) and/or HPLC methods. The protein activity of the purified Cel3a-N'His was recorded as percent conversion of cellobiose to glucose per 30 minutes (FIG. 5).

Figure 6:
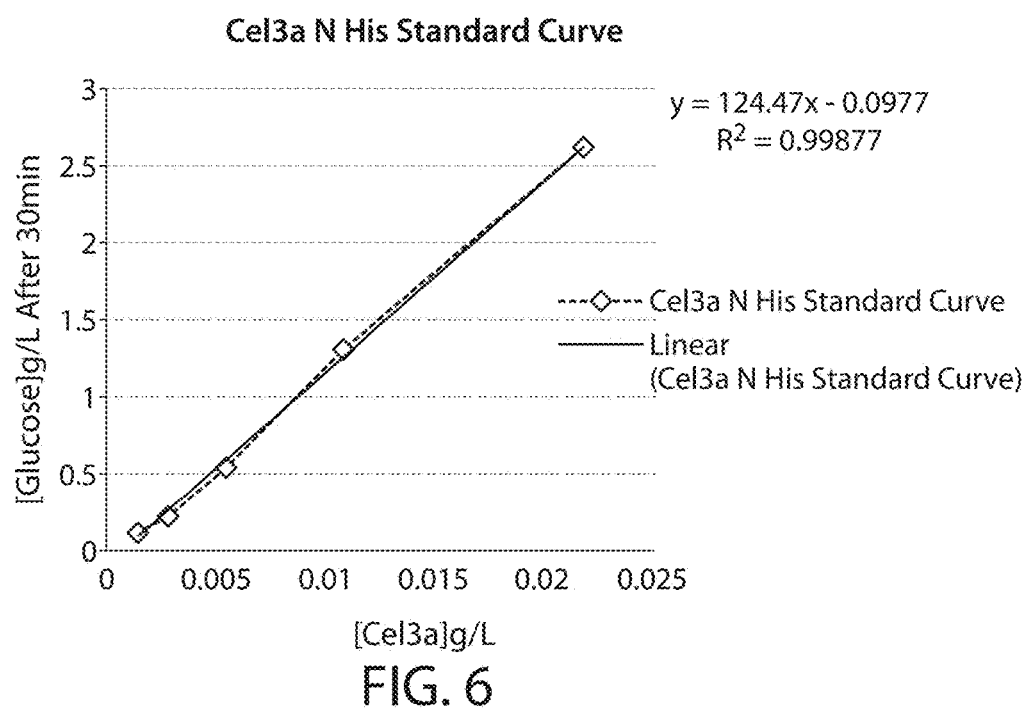

For samples where the amount of Cel3a cannot be assayed by using a Bradford assay and/or the nanodrop, e.g., crude lysate sample, the activity assay can be used to determine the titer of Cel3a. A standard curve of cellobiase activity of a sample of purified Cel3a-N'His with a known concentration is generated. Two-fold serial dilutions of Cel3a-N'His with a known concentration were prepared in one row of a 96 well plate, e.g., 12 two-fold serial dilutions. The other rows contained two-fold serial dilutions of other remaining samples whose titer is to be determined, e.g., the crude lysate sample. The dilutions were incubated with a D-(+)-Cellobiose (Fluka) substrate solution in 50 mM sodium citrate monobasic buffer at pH 5.0, at 48° C. for 30 minutes. After 30 minutes, the samples were heated to 100° C. for 10 minutes to stop the reaction. Samples were analysed for glucose and cellobiose using the YSI Biochemistry analyser (YSI Life Sciences) and/or HPLC methods. Using Cel3a-N'His samples of known concentration, a standard curve is generated using the data points within the linear range of the assay (FIG. 6). The cellobiase activity detected from the samples with unknown Cel3a titer can be compared to the standard curve to determine the titer of Cel3a in the sample.

Units of activity are only relative if calculated using values within the linear range of the assay. The linear range of the assay is defined as using glucose values that are less than 30% of the original soluble substrate load. In addition, glucose values lower than 0.05 g/L are omitted due to instrumentation reporting levels. One unit of cellobiase activity is defined as the amount of glucose per the amount of Cel3a per 30 minutes: [Glucose]g/L/[Cel3a]g/L/30 min.

Figure 7:
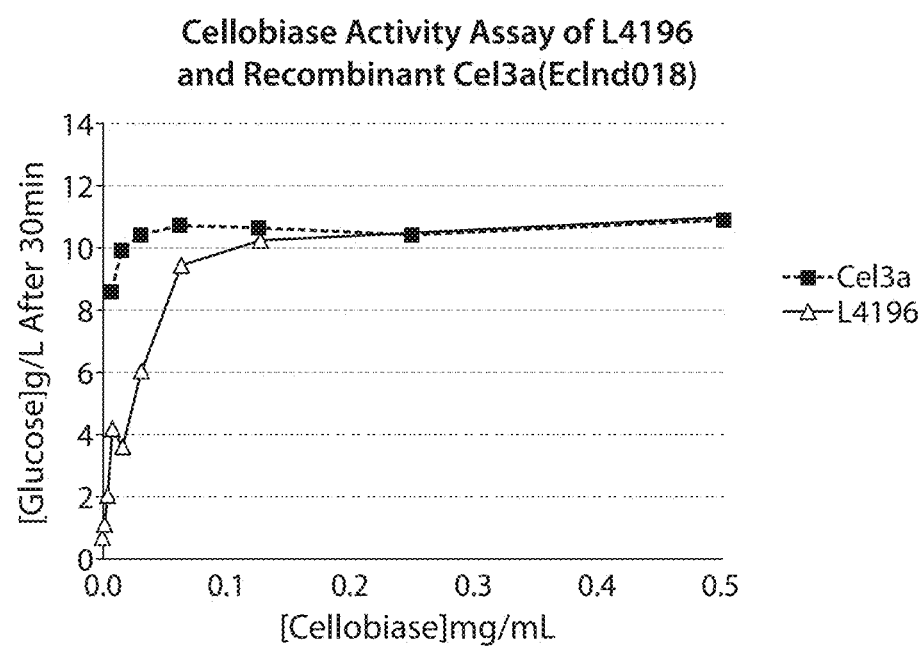
FIG. 7 is a graph showing that specific activity of recombinant Cel3a compared to endogenous cellobiase from *T. Reesei* (L4196).

A comparison of the activity between aglycosylated Cel3a purified from E. coli and endogenous (glycosylated) cellobiase Cel3a from T. reesei was performed, using the cellobiase activity described herein. The results are shown in FIG. 7, which show that the recombinant Cel3a (aglycosylated Cel3a purified from E. coli; labeled Cel3a in FIG. 7) demonstrated higher specific activity for converting cellobiose to glucose compared to the endogenous Cel3a (labeled L4196 in FIG. 7). Specifically, at concentrations lower than 0.2 mg/mL of cellobiase, the recombinant Cel3a was able to produce a larger amount of glucose after 30 minutes than the endogenous Cel3a.

Figure 8:
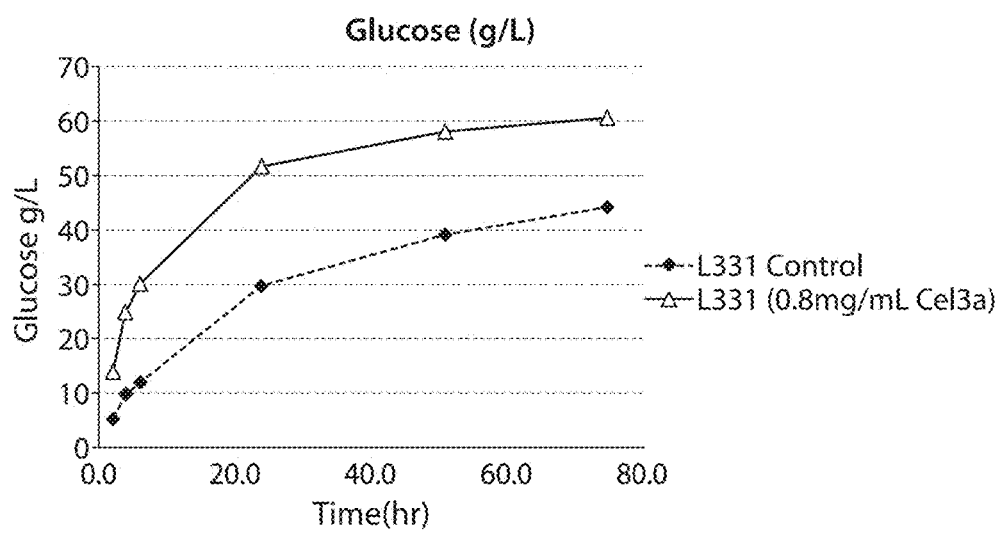
FIG. 8 is a graph showing the yield of glucose product from a saccharification reaction performed with a standard enzyme mix compared to the standard enzyme mix (L331 control) with the addition of aglycosylated cellobiase Cel3a (L331 (0.8 mg/ml Cel3a).

Example 7: Addition of Aglycosylated Cellobiase Increases Product from Saccharification Process In this example, the glucose yield was compared between two saccharification reactions. In one saccharification reaction, an enzyme mixture comprising the enzymes described in Table 1 was added to a biomass. In a second saccharification reaction, 0.8 mg/ml of aglycosylated Cel3a purified from E. coli was added to the enzyme mixture comprising the enzymes described in Table 1, and was added to a biomass. The saccharification reactions were run under the conditions as described herein, with samples taken at multiple timepoints between 0 and 80 minutes of the reaction. The resulting glucose was measured and quantified using methods in the art, such as by YSI instrument or HPLC, and plotted over time, as shown in FIG. 8. These results show that addition of aglycosylated Cel3a increased the yield of sugar product, e.g., glucose, in a saccharification reaction.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. An aglycosylated polypeptide having cellobiase activity comprising the amino acid sequence of SEQ ID NO: 1.

2. The aglycosylated polypeptide of claim 1, wherein the aglycosylated polypeptide:
   (i) has increased cellobiase activity as compared to a glycosylated Cel3A enzyme comprising the amino acid sequence of SEQ ID NO: 1;
   (ii) has increased substrate recognition, a more active substrate recognition site, or reduced steric hindrance as compared to a glycosylated Cel3A enzyme comprising the amino acid sequence of SEQ ID NO: 1; and/or
   (iii) hydrolyzes a carbohydrate into one or more monosaccharides.

3. The aglycosylated polypeptide of claim 1, wherein the cellobiase activity comprises hydrolysis of a beta 1,4 glycosidic linkage of cellobiose.

4. An enzyme mixture comprising a glycosylated polypeptide comprising the amino acid sequence of SEQ ID NO: 1, and an aglycosylated polypeptide comprising the amino acid sequence of SEQ ID NO: 1, wherein both of the glycosylated polypeptide and the aglycosylated polypeptide have cellobiase activity.

5. The enzyme mixture of claim 4, further comprising at least one additional enzyme derived from a microorganism, wherein the additional enzyme has a biomass-degrading activity of a cellulose based material, wherein the additional enzyme is selected from a ligninase, an endoglucanase, a cellobiohydrolase, xylanase, and a cellobiase.

6. The enzyme mixture of claim 4, wherein the ratio between the aglycosylated polypeptide to the remaining enzymes or to the glycosylated polypeptide in the mixture is at least 1:32.

7. The enzyme mixture of claim 4, wherein the ratio between the aglycosylated polypeptide to the remaining enzymes or to the glycosylated polypeptide in the mixture is at least 1:2.

8. The enzyme mixture of claim 4, wherein the ratio between the aglycosylated polypeptide to the remaining enzymes or to the glycosylated polypeptide in the mixture is at least 1:16.

9. The enzyme mixture of claim 4, wherein the ratio between the aglycosylated polypeptide to the remaining enzymes or to the glycosylated polypeptide in the mixture is at least 1:50.

10. An enzyme mixture comprising a glycosylated polypeptide comprising the amino acid sequence of SEQ ID NO: 1 and an aglycosylated polypeptide comprising the amino acid sequence of SEQ ID NO: 1, wherein the mixture further comprises a biomass degrading enzyme chosen from a ligninase, an endoglucanase, a cellobiohydrolase, xylanase, and a cellobiase.

11. The enzyme mixture of claim 10, wherein the biomass degrading enzyme is chosen from B2AF03, CIP1, CIP2, Cel1a, Cel3a, Cel5a, Cel6a, Cel7a, Cel7b, Cel12a, Cel145a, Cel74a, paMan5a, paMan26a, and Swollenin.

12. The enzyme mixture of claim 10, wherein the ratio between the aglycosylated polypeptide to the remaining enzymes or to the glycosylated polypeptide in the mixture is at least 1:2.

13. The enzyme mixture of claim 10, wherein the ratio between the aglycosylated polypeptide to the remaining enzymes or to the glycosylated polypeptide in the mixture is at least 1:16.

14. The enzyme mixture of claim 10, wherein the ratio between the aglycosylated polypeptide to the remaining enzymes or to the glycosylated polypeptide in the mixture is at least 1:32.

15. The enzyme mixture of claim 10, wherein the ratio between the aglycosylated polypeptide to the remaining enzymes or to the glycosylated polypeptide in the mixture is at least 1:50.

16. The enzyme mixture of claim 10, wherein the glycosylated polypeptide and the aglycosylated polypeptide both comprise a Cel3A enzyme from wild-type T. reesei.

* * * * *